(12) United States Patent
Jansen et al.

(10) Patent No.: US 7,417,157 B2
(45) Date of Patent: Aug. 26, 2008

(54) HEXAHYDRODIBENZOFURAN DERIVATIVES

(75) Inventors: Axel Jansen, Darmstadt (DE); Andreas Taugerbeck, Darmstadt (DE); Melanie Klasen-Memmer, Heuchelheim (DE)

(73) Assignee: Merck Patent Gesellschaft mit Beschrankter Haftung, Darmstadt (DE)

( * ) Notice: Subject to any disclaimer, the term of this patent is extended or adjusted under 35 U.S.C. 154(b) by 0 days.

(21) Appl. No.: 11/790,214

(22) Filed: Apr. 24, 2007

(65) Prior Publication Data

US 2007/0247585 A1   Oct. 25, 2007

(30) Foreign Application Priority Data

Apr. 25, 2006   (DE) .................. 10 2006 019 045

(51) Int. Cl.
*C07D 307/91* (2006.01)
(52) U.S. Cl. .............. 549/460; 349/184; 549/461
(58) Field of Classification Search ........... 549/460, 549/461; 349/184
See application file for complete search history.

(56) References Cited

U.S. PATENT DOCUMENTS

| | | | |
|---|---|---|---|
| 5,231,198 A * | 7/1993 | Powers et al. ............ | 549/461 |
| 7,018,685 B2 | 3/2006 | Schmidt et al. | |
| 2005/0258397 A1 | 11/2005 | Schmidt et al. | |
| 2005/0258399 A1 | 11/2005 | Schmidt et al. | |

FOREIGN PATENT DOCUMENTS

| | | |
|---|---|---|
| DE | 10 2004 020 479 A1 | 11/2005 |
| DE | 10 2004 021 691 A1 | 11/2005 |
| WO | WO 02/055463 A1 | 1/2002 |
| WO | WO 02/055463 A1 | 7/2002 |

OTHER PUBLICATIONS

V. Grant et al., "Iridium(III)-catalyzed tandem claisen rearrangement-Intramolecular hydroaryloxylation of aryl allyl ethers to form dihydrobenzofurans", Tetrahedron Letters, vol. 46 (2005) pp. 1237-1239.

* cited by examiner

*Primary Examiner*—Bernard Dentz
*Assistant Examiner*—David E Gallis
(74) *Attorney, Agent, or Firm*—Millen, White, Zelano Branigan, P.C.

(57) ABSTRACT

Disclosed are hexahydrodibenzofuran compounds of formula I,

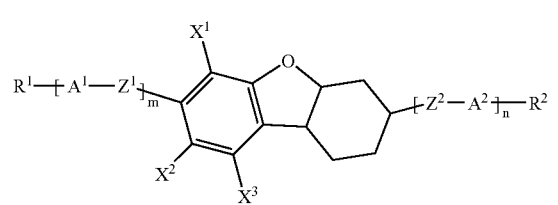

the preparation thereof, the use thereof as components in liquid-crystalline media, and to electro-optical display elements which contain the liquid-crystalline media according to the invention.

14 Claims, No Drawings

HEXAHYDRODIBENZOFURAN DERIVATIVES

The present invention relates to hexahydrodibenzofuran derivatives, to the preparation thereof, to liquid-crystalline media comprising these derivatives, and to electro-optical display elements containing these liquid-crystalline media. In particular, the invention relates to hexahydrodibenzofuran derivatives of negative dielectric anisotropy.

Liquid crystals have found widespread use since the first commercially usable liquid-crystalline compounds were found about 30 years ago. Known areas of application are, in particular, displays for watches and pocket calculators, and large display panels as used in railway stations, airports and sports arenas. Further areas of application are displays of portable computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elasto-mechanical anisotropies. Depending on whether the molecules are oriented with their longitudinal axes perpendicular or parallel to the two plates of a capacitor, the latter has a different capacitance; in other words, the dielectric constant $\epsilon$ of the liquid-crystalline medium has different values for the two orientations. Substances whose dielectric constant is larger when the longitudinal axes of the molecules are oriented perpendicular to the capacitor plates than when they are oriented parallel are referred to as di-electrically positive. In other words, if the dielectric constant $\epsilon_{\parallel}$ parallel to the longitudinal axes of the molecules is larger than the dielectric constant $\epsilon_{\perp}$ perpendicular to the longitudinal axes of the molecules, the dielectric anisotropy $\Delta\epsilon=\epsilon_{\parallel}-\epsilon_{\perp}$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. In the most widespread TN ("twisted nematic") cells, a liquid-crystalline layer with a thickness of only from about 5 to 10 μm is arranged between two plane-parallel glass plates, onto each of which an electrically conductive, transparent layer of tin oxide or indium tin oxide (ITO) has been vapour-deposited as electrode. A likewise transparent alignment layer, usually consisting of a plastic (for example polyimides), is located between these films and the liquid-crystalline layer. This alignment layer serves to bring the longitudinal axes of the adjacent liquid-crystalline molecules into a preferential direction through surface forces in such a way that, in the voltage-free state, they lie uniformly with the same orientation, flat or with the same small tilt angle, on the inside of the display surface. Two polarisation films which only enable linear-polarised light to enter and escape are applied to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\epsilon$ is negative. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

Development in the area of liquid-crystalline materials is still far from complete. In order to improve the properties of liquid-crystalline display elements, attempts are constantly being made to develop novel compounds which enable optimisation of such displays.

WO 02/055463 A1 discloses, inter alia, 3-monosubstituted and 3,7-disubstituted 4,6-difluorodibenzofurans and -thiophenes, without giving precise details of the physical or electro-optical properties.

It is therefore an object of the present invention to provide compounds having advantageous properties for use in liquid-crystalline media. In particular, they should have negative dielectric anisotropy, which makes them particularly suitable for use in liquid-crystalline media for VA displays. Irrespective of the dielectric anisotropy corresponding to the display type, compounds are desired which have a favourable combination of the applicational parameters. Of these parameters, which are to be optimised simultaneously, particular mention should be made of a high clearing point, a low rotational viscosity, an optical anisotropy in the use range, and the properties which serve to achieve mixtures having the desired liquid-crystalline phases over a broad temperature range.

This object is achieved in accordance with the invention by compounds of the general formula I

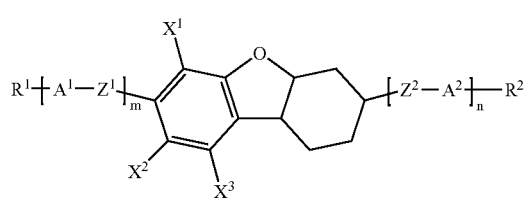

in which m and n each, independently of one another, are 0, 1 or 2, $X^1$, $X^2$ and $X^3$ each, independently of one another, denote H, halogen, CN or $CF_3$, preferably H, F, Cl, CN or $CF_3$, $A^1$ and $A^2$ each, independently of one another, denote 1,4-phenylene, in which =CH— may be replaced once or twice by =N— and which may be unsubstituted or mono- to tetrasubstituted, independently of one another, by —CN, —F, —Cl, —Br, —I, unsubstituted or mono- or polyfluorine- and/or -chlorine-substituted $C_1$-$C_6$-alkanyl, unsubstituted or mono- or polyfluorine-and/or -chlorine-substituted $C_1$-$C_6$-alkoxy, 1,4-cyclohexylene, 1,4-cyclohexenylene or 1,4-cyclohexadienylene, in which —$CH_2$— may be replaced once or twice, independently of one another, by —O— or —S— in such a way that heteroatoms are not linked directly, and which may be unsubstituted or mono- or polysubstituted by —F and/or —Cl, bicyclo[1.1.1]pentane-1,3-diyl, bicyclo[2.2.2]octane-1,4-diyl, spiro[3.3]heptane-2,6-diyl, tetrahydropyran-2,5-diyl or 1,3-dioxane-2,5-diyl, $Z^1$ and $Z^2$ each, independently of one another, denote a single bond, —$CF_2O$—, —$OCF_2$—, —$CH_2CH_2$—, —$CF_2CF_2$—, —$CF_2CH_2$—, —$CH_2CF_2$—, —CHF—CHF—, —(CO)O—, —O(CO)—, —$CH_2O$—, —$OCH_2$—, —CF=CH—, —CH=CF—, —CF=CF—, —CH=CH— or —C≡C—;

$R^1$ and $R^2$, independently of one another, denote hydrogen, an alkanyl, alkoxy, alkenyl or alkynyl radical having 1 to 15 or 2 to 15 C atoms respectively which is unsubstituted, monosubstituted by —CN or —$CF_3$ or mono- or polysubstituted by —F, —Cl, —Br and/or —I, where one or more $CH_2$ groups in these radicals may also each, independently of one another, be replaced by —O—, —S—, —$SO_2$—, —CO—, —(CO)O—, —O(CO)— or —O(CO)O— in such a way that heteroatoms are not linked directly, —F, —Cl, —Br, —I, —CN, —SCN, —NCS or —$SF_5$;

where $A^1$, $A^2$, $Z^1$, $Z^2$ may each have identical or different meanings if m or n respectively is greater than 1, and where in the case where simultaneously n=0, m=0 and $X^1$, $X^2$ and $X^3$ are not equal to F, $R^1$ and $R^2$ then do not simultaneously denote H.

The compounds have predominantly negative Δε and are therefore particularly suitable for use in VA-TFT displays. The compounds according to the invention preferably have a Δε of <-2 and particularly preferably a Δε of <-4. They exhibit very good compatibility with the usual substances used in liquid-crystal mixtures for displays.

Furthermore, the compounds of the formula I according to the invention have values for the optical anisotropy Δn which are particularly suitable for use in VA-TFT displays. The compounds according to the invention preferably have a Δn of greater than 0.05 and less than 0.40.

The other physical, physicochemical or electro-optical parameters of the compounds according to the invention are also advantageous for use of the compounds in liquid-crystalline media. The compounds or liquid-crystalline media comprising these compounds have, in particular, a sufficient breadth of the nematic phase and good low-temperature and long-term stability as well as sufficiently high clearing points. The rotational viscosities of the compounds are advantageously low, particularly for m+n=0.

It is furthermore preferred for one or two of the radicals $X^1$, $X^2$ and $X^3$ to denote Cl or F, in particular fluorine. It is particularly preferred for $X^2$ and $X^3$ to denote H and $X^1$ not to denote hydrogen. Alternatively, $X^1$ is preferably H and at least one of the substituents $X^2$ and $X^3$ is not hydrogen. $X^1$, $X^2$ and $X^3$ are particularly preferably, independently of one another, H or F. In a particularly preferred embodiment, $X^1$ is therefore fluorine and $X^2$ and $X^3$ are hydrogen. Alternatively, it is particularly preferred for $X^1$ to be H, $X^2$ to be F and $X^3$ to be H or F.

In the case where the radical $R^1$ denotes a fluorine atom or fluorinated alkyl, in particular if m simultaneously denotes 0, the formula I then also encompasses compounds which may have an overall positive dielectric anisotropy. Such compounds are then suitable for dielectrically positive liquid-crystal mixtures which are used in displays, such as, for example, of the TN-TFT or IPS ('in-plane switching') type. The requirements of the other physical parameters, such as, for example, the viscosity, are substantially congruent over most applications. The said compounds are thus equally suitable for these purposes since they have favourable values for the parameters, such as rotational viscosity, Δn, etc., and are suitable for the preparation of liquid-crystalline mixtures.

$A^1$ and $A^2$ are preferably and independently of one another an optionally substituted 1,4-phenylene, an optionally substituted 1,4-cyclohexylene, in which —$CH_2$— may be replaced once or twice by —O—, or an optionally substituted 1,4-cyclohexenylene. If n or m is 2, the rings $A^1$ and $A^2$ may adopt identical or different meanings.

$A^1$ and $A^2$ are particularly preferably, independently of one another,

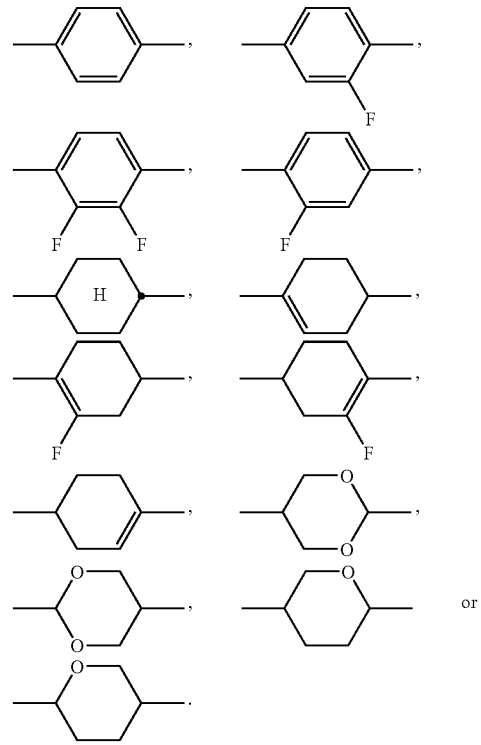

$A^1$ and $A^2$ are very particularly preferably 1,4-cyclohexylene rings and/or optionally fluorine-substituted 1,4-phenylene rings.

$Z^1$ and $Z^2$ are preferably, independently of one another, a single bond, —$CH_2O$—, —$OCH_2$—, —$CF_2O$—, —$OCF_2$—, —$CF_2CF_2$—, —CH=CH—, —CF=CH—, —CH=CF— or —CF=CF—, particularly preferably, independently of one another, a single bond, —$CF_2O$—, —$OCF_2$—, —$CF_2CF_2$—, —CH=CH—, —CF=CH—, —CH=CF—, —$CH_2O$—, —$OCH_2$— or —CF=CF—. $Z^1$ and $Z^2$ are very particularly preferably, independently of one another, a single bond, —$CF_2O$—, —$OCF_2$—, —$CH_2O$—, —$OCH_2$— or —CF=CF—, in particular a single bond.

If $R^1$ and $R^2$ in the formula I each, independently of one another, represent an alkanyl radical and/or an alkoxy radical (alkyloxy radical) having 1 to 15 C atoms, these are straight-chain or branched. Each of these radicals is preferably straight-chain, has 1, 2, 3, 4, 5, 6 or 7 C atoms and is accordingly preferably methyl, ethyl, propyl, butyl, pentyl, hexyl, heptyl, methoxy, ethoxy, propoxy, butoxy, pentoxy, hexyloxy or heptyloxy.

$R^1$ and $R^2$ in the formula I may each, independently of one another, also be an oxaalkyl radical, i.e. an alkanyl radical in which at least one of the non-terminal $CH_2$ groups has been replaced by —O—, preferably straight-chain 2-oxapropyl (=methoxymethyl), 2- (=ethoxymethyl) or 3-oxabutyl (=methoxyethyl), 2-, 3- or 4-oxapentyl, 2-, 3-, 4- or 5-oxahexyl, or 2-, 3-, 4-, 5- or 6-oxaheptyl. In a corresponding manner, $R^1$ and $R^2$ in the formula I may also, independently of one another, be thioalkanyl or sulfonealkanyl radicals, i.e. alkanyl radicals in which one $CH_2$ group has been replaced by —S— or —$SO_2$—.

$R^1$ and $R^2$ in the formula I may furthermore each, independently of one another, be an alkenyl radical having 2 to 15 C atoms which is straight-chain or branched and has at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl. If the two C atoms of the C—C double bond are substituted, the alkenyl radical can be in the form of the E and/or Z isomer (trans/cis). In general, the respective E isomers are preferred.

In the same way as for an alkanyl radical, at least one of the $CH_2$ groups in an alkenyl radical may also have been replaced by oxygen, sulfur or —$SO_2$—. In the case of replacement by —O—, an alkenyloxy radical (having a terminal oxygen) or an oxaalkenyl radical (having a non-terminal oxygen) is then present.

$R^1$ and $R^2$ in the formula I may also, independently of one another, be an alkynyl radical having 2 to 15 C atoms which is straight-chain or branched and has at least one C—C triple bond.

$R^1$ and $R^2$ in the formula I may each, independently of one another, be an alkanyl radical having 1 to 15 C atoms in which one $CH_2$ group has been replaced by —O— and one has been replaced by —CO—, where these are preferably adjacent. This thus contains an acyloxy group —CO—O— or an oxycarbonyl group —O—CO—. This radical is preferably straight-chain and has 2 to 6 C atoms. The following of these radicals are preferred here: acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonyl-methyl, propoxycarbonylmethyl, butoxycarbonylmethyl, 2-(methoxycarbonyl)-ethyl, 2-(ethoxycarbonyl)ethyl, 2-(propoxycarbonyl)ethyl, 3-(methoxy-carbonyl)propyl, 3-(ethoxycarbonyl)propyl and 4-(methoxycarbonyl)butyl. Furthermore, an alkanyl radical can also have an —O—CO—O— unit. Replacement of a $CH_2$ group by only one —CO— group (carbonyl function) is also possible.

$R^1$ and $R^2$ in the formula I may each, independently of one another, be an alkenyl radical having 2 to 15 C atoms in which a $CH_2$ group, preferably in the vicinity of an unsubstituted or substituted —C=C— unit, has been replaced by —CO—, —CO—O—, —O—CO— or —O—CO—O—, where this radical may be straight-chain or branched. The radical is preferably straight-chain and has 4 to 13 C atoms. Particular preference is given here to acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9acryloyloxynonyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl and 8-methacryloyloxyoctyl. Correspondingly, a $CH_2$ group in the vicinity of a substituted —C≡C-unit in an alkynyl radical may also be replaced by —CO—, —CO—O—, —O—CO— or —O—CO—O—.

$R^1$ and $R^2$ in the formula I may each, independently of one another, be an alkanyl radical or alkoxy radical having 1 to 15 C atoms or an alkenyl radical or alkynyl radical having 2 to 15 C atoms, each of which is monosubstituted by —CN or —$CF_3$, where these are preferably straight-chain. The substitution by —CN or —$CF_3$ is possible in any desired position.

$R^1$ and $R^2$ in the formula I may each, independently of one another, be an alkanyl radical in which two or more $CH_2$ groups have been replaced by —O— and/or —CO—O—, where this may be straight-chain or branched. It is preferably branched and has 3 to 12 C atoms.

$R^1$ and $R^2$ in the formula I may each, independently of one another, be an alkanyl radical or alkoxy radical having 1 to 15 C atoms or an alkenyl radical or alkynyl radical having 2 to 15 C atoms, each of which is mono- or polysubstituted by F, Cl, Br and/or 1, where these radicals are preferably straight-chain and halogen is preferably —F and/or —Cl. In the case of poly-substitution, halogen is preferably —F. The resultant radicals also include perfluorinated radicals, such as —$CF_3$. In the case of monosubstitution, the fluorine or chlorine substituent can be in any desired position, but is preferably in the ω-position.

$R^1$ and $R^2$ in the formula I may also each, independently of one another, be —F, —Cl, —Br, —I, —CN, —SCN, —NCS or —$SF_5$. In this case, the dielectric anisotropy increases towards more positive values. For very particularly strongly negative dielectric anisotropies, these substituents should not be selected. However, they are preferred for high $\Delta\epsilon$.

$R^1$ and $R^2$ in the general formula I are particularly preferably, independently of one another, hydrogen or an alkanyl radical, alkoxy radical or alkenyl radical having 1 to 7 or 2 to 7 C atoms respectively, where each of these radicals is preferably unsubstituted or monosubstituted or polysubstituted by halogen.

$R^1$ and $R^2$ are very particularly preferably, independently of one another, hydrogen or an alkanyl radical, alkoxy radical or alkenyl radical having 1 to 7 or 2 to 7 C atoms respectively, where each of these radicals is preferably unsubstituted.

In the case where m=0, $R^1$ preferably denotes an alkyl or alkoxy group, H or F, particularly preferably an alkoxy group having 1-6 C atoms.

For the said substituents $R^1$ and $R^2$, the restriction mentioned at the outset applies in the case where m and n are 0 and $X^1$, $X^2$ and $X^3$ are not equal to F. Furthermore, particularly in the case where m and n are 0, $R^1$ and $R^2$ preferably do not simultaneously denote H.

In connection with the present invention, halogen denotes fluorine, chlorine, bromine or iodine, in particular fluorine or chlorine.

In connection with the present invention, the term "alkyl"—unless defined otherwise elsewhere in this description or in the claims—denotes a straightchain or branched aliphatic hydrocarbon radical having 1 to 15 (i.e. 1, 2, 3, 4, 5, 6, 7, 8, 9, 10, 11, 12, 13, 14 or 15) carbon atoms. This radical is unsubstituted or monosubstituted or polysubstituted by fluorine, chlorine, bromine, iodine, carboxyl, nitro, —NH$_2$, —N(alkanyl)$_2$ and/or cyano, where the polysubstitution can take place with identical or different substituents. If this alkyl radical is a saturated radical, it is also referred to as "alkanyl". Furthermore, the term "alkyl" also encompasses hydrocarbon radicals which are unsubstituted or correspondingly mono- or polysubstituted by identical or different substituents, in particular by —F, —Cl, —Br, —I and/or —CN or —CF$_3$, and in which one or more CH$_2$ groups may be replaced by —O— ("alkoxy", "oxaalkyl"), —S— ("thioalkyl"), —SO$_2$—, —CH=CH— ("alkenyl"), —C≡C— ("alkynyl"), —CO—O—, —O—CO— or —O—CO—O— in such a way that hetero atoms (O or S) in the chain are not linked directly to one another.

Preferred compounds of the general formula I have a total of zero, one, two or three units -Z$^1$-A$^1$-and/or -Z$^2$-A$^2$-, i.e. m+n=0, 1, 2 or 3 where m and n are each 0, 1, 2 or 3. If two or three units -Z$^1$-A$^1$- and/or -Z$^2$-A$^2$- are present, they may be bonded to only one side of the molecule (i.e. m=2 or 3 and n=0 or n=2 or 3 and m=0) or also to both sides of the molecule. Preferably, m or n is 0. Particularly preferably, m+n=0, 1 or 2 and very particularly 0 or 1.

Preferred compounds of the formula I for which m+n=0 are represented by the following formula:

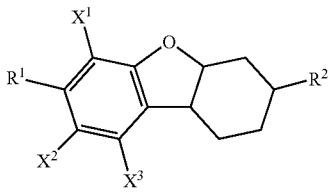

Ia in which

R$^1$, R$^1$, X$^1$, X$^2$ and X$^3$ have the same and the same preferred meanings as defined above for the formula I.

In the case where R$^1$ is hydrogen, at least one group from X$^1$, X$^2$ and X$^3$ is preferably a fluorine substituent, in particular X$^1$.

Preferred compounds of the formula I for which m+n=1 are represented by the following formulae:

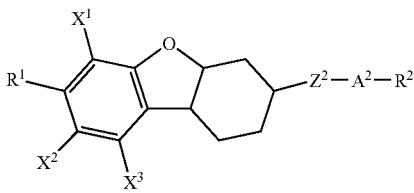

Ib

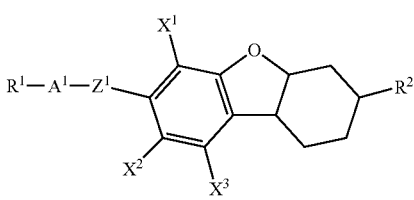

Ic in which

R$^1$, R$^2$, A$^1$, A$^2$, X$^1$, X$^2$, X$^3$, Z$^2$ and Z$^2$ have the same and the same preferred meanings as defined above for the formula I.

Preferred compounds of the formula I for which m+n=2 are represented by the following formulae:

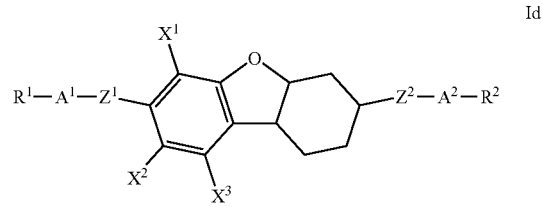

Id

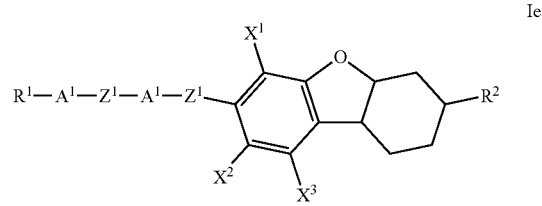

Ie

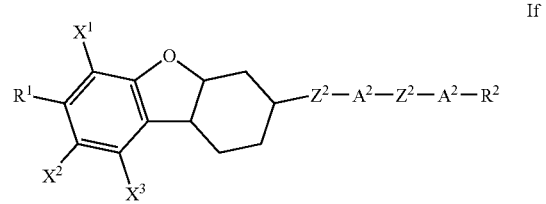

If in which

R$^1$, R$^2$, A$^1$, A$^2$, X$^1$, X$^2$, X$^3$, Z$^1$ and Z$^2$ have the same and the same preferred meanings as defined above for the formula I.

If A$^1$, A$^2$, Z$^1$ or Z$^2$ occurs twice in the formulae Ie and If, it may in each case have identical or different meanings.

Preferred compounds of the formula I for which m+n=3 are represented by the following formulae:

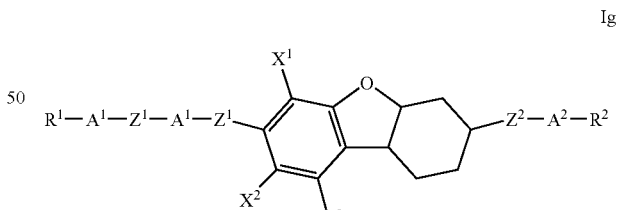

Ig

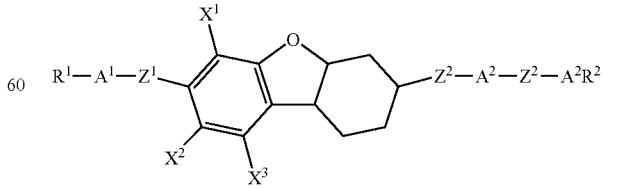

Ih

-continued

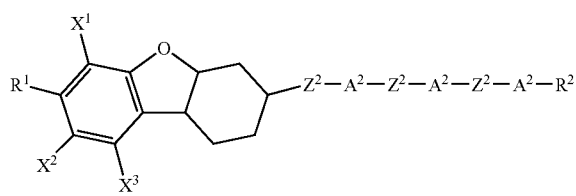
Ii

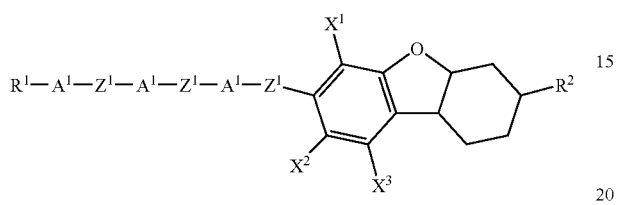
Ij in which $R^1, R^2, A^1, A^2, X^1, X^2, X^3, Z^1, Z^2$ and Y have the same and the same preferred meanings as defined above for the formula I.

If $A^1, A^2, Z^1$ or $Z^2$ occurs more than once in the formulae Ig to Ij, it may in each case have identical or different meanings.

Particular preference is given to compounds of the formulae Ia, Ib, Ic, Id, Ie and If, in particular of the formulae Ia, Ib and Ic, according to the invention.

Very particularly preferred compounds of the formula Ia are the following:

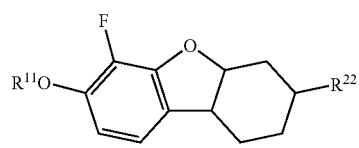
Ia-1

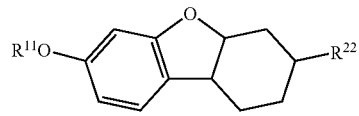
Ia-2

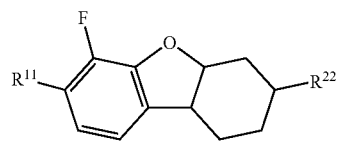
Ia-3

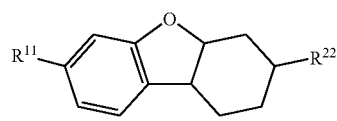
Ia-4

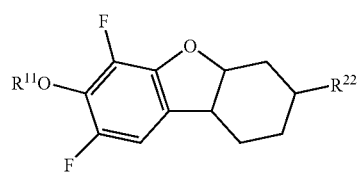
Ia-5

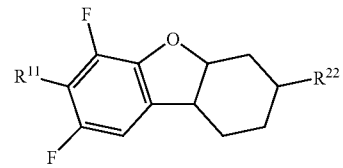
Ia-6

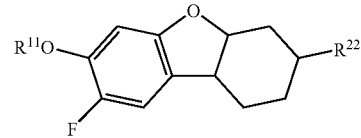
Ia-7

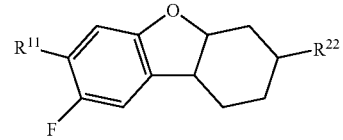
Ia-8

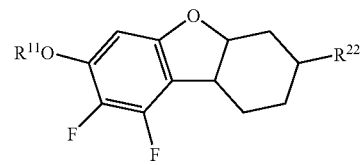
Ia-9

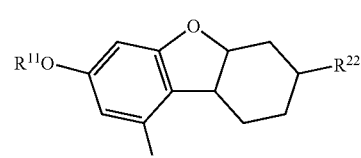
Ia-10

Ia-11

Ia-12 in which $R^{11}$ and $R^{22}$ denote an alkyl radical having up to 8 C atoms.

In the case where $R^{11}$ is bonded directly to the ring, $R^{11}$ may preferably also denote F, as in the compounds of the following formulae:

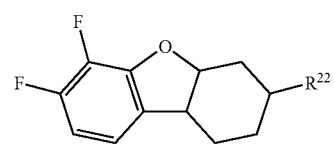
Ia-13

Ia-14
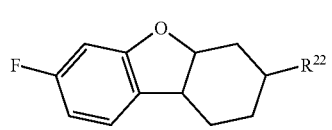
Ia-15
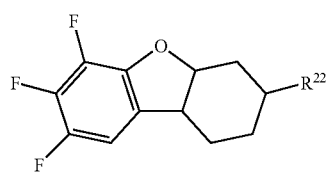
Ia-16
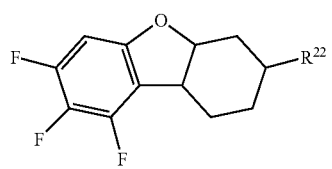
Ia-17
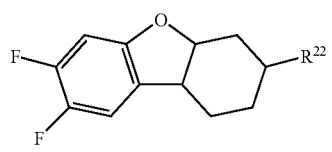
Ia-18
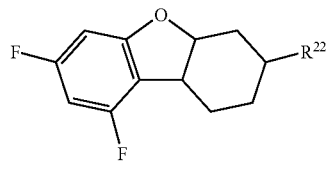
Of the compounds of the formulae Ia-1 to Ia-12, further preference is given to those of the formulae Ia-1 to Ia-4, in particular compounds of the formulae Ia-1 and Ia-3.
Of the preferred compounds of the formula Ib according to the invention, particular preference is given to the following:
Ib-1
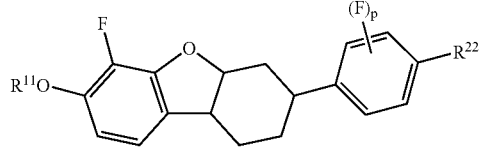
Ib-2
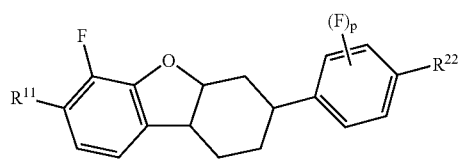
Ib-3
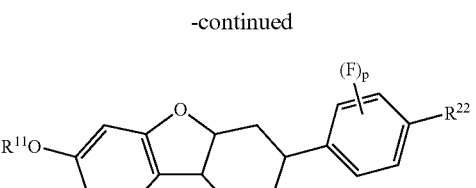
Ib-4
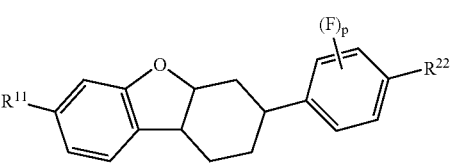
Ib-5
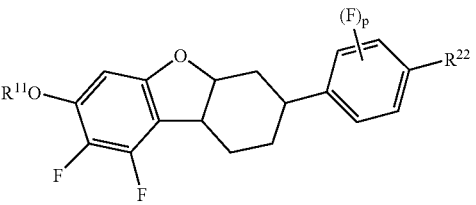
Ib-6
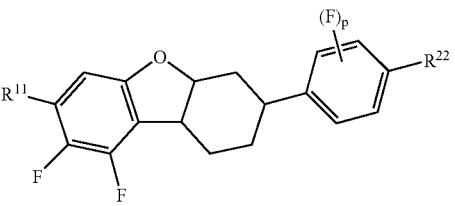
Ib-7
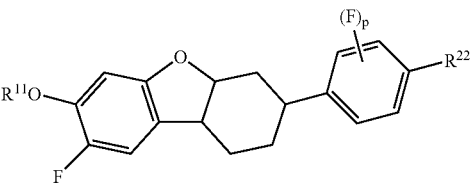
Ib-8
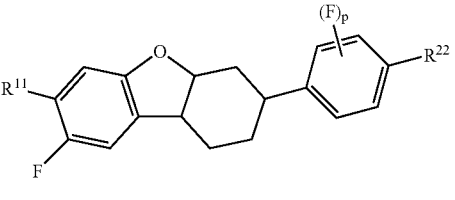
Ib-9
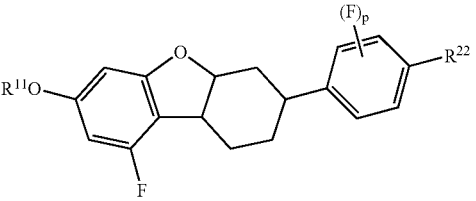
Ib-10
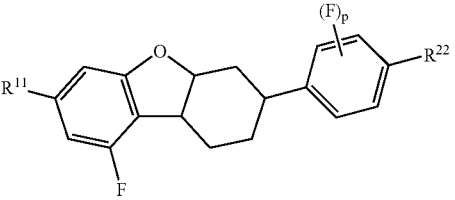

-continued
Ib-11
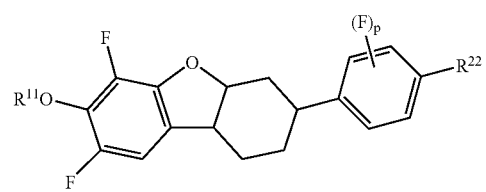
Ib-12
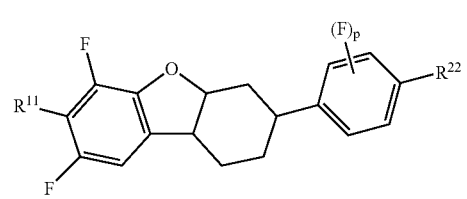
Ib-13
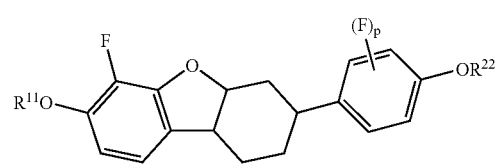
Ib-14
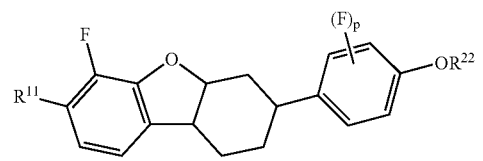
Ib-15
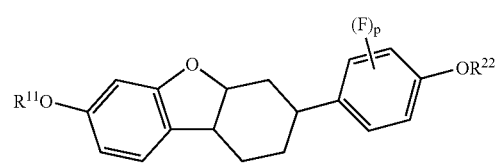
Ib-16
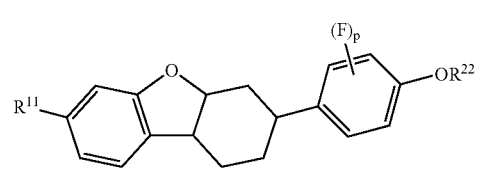
Ib-17
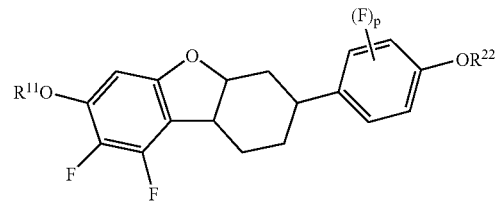
-continued
Ib-18
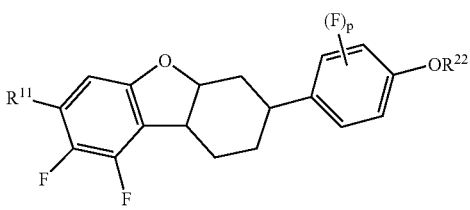
Ib-19
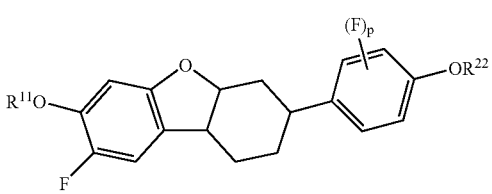
Ib-20
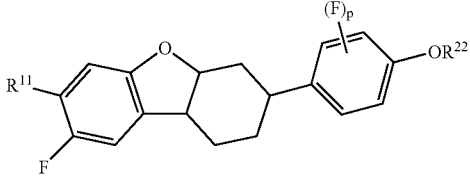
Ib-21
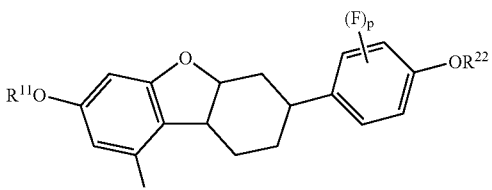
Ib-22
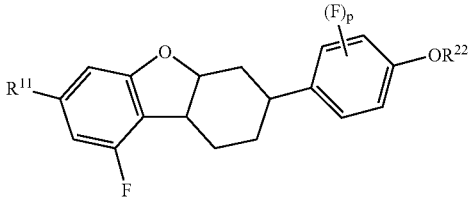
Ib-23
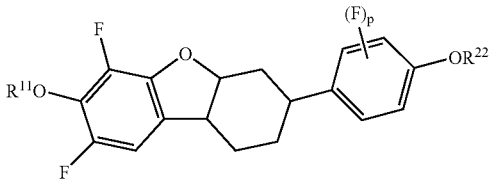
Ib-24
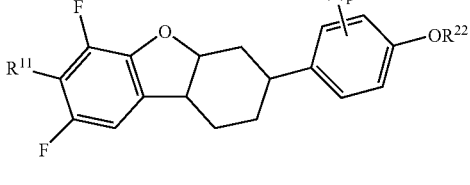
Ib-25
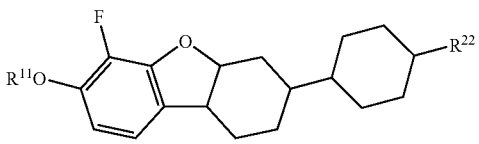

-continued
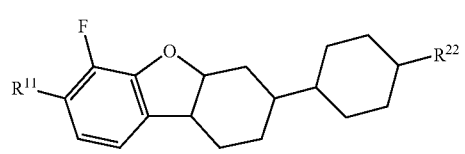
Ib-26
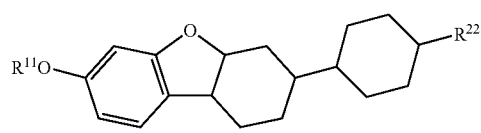
Ib-27
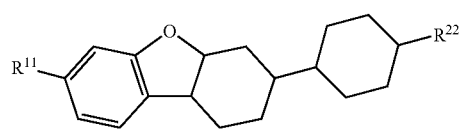
Ib-28
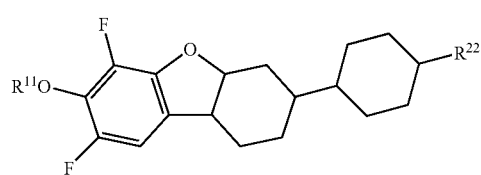
Ib-29
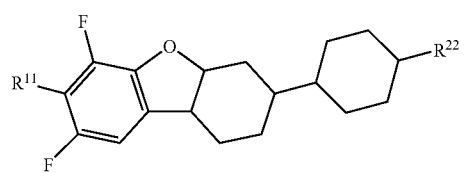
Ib-30
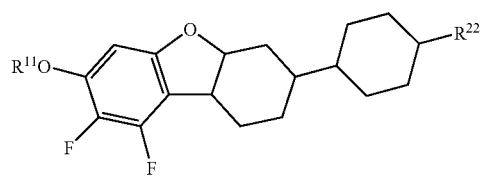
Ib-31
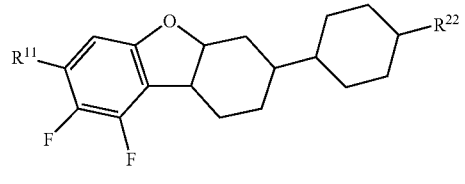
Ib-32
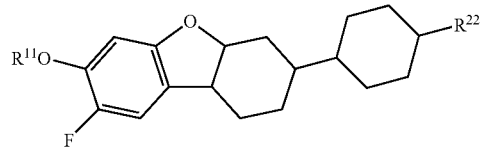
Ib-33
-continued
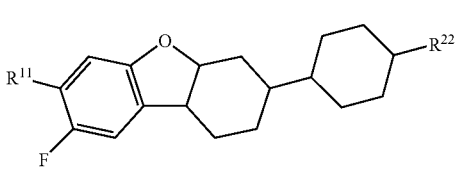
Ib-34
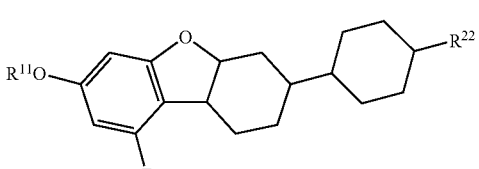
Ib-35
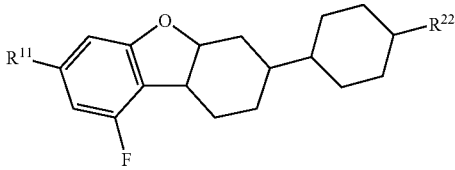
Ib-36
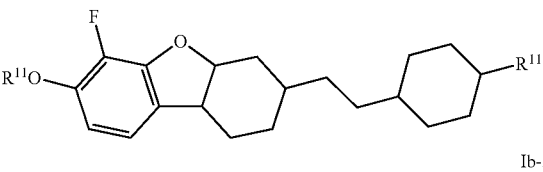
Ib-37
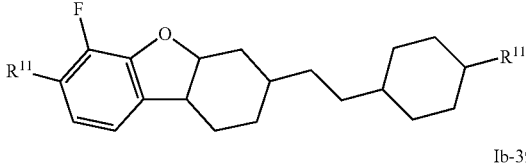
Ib-38
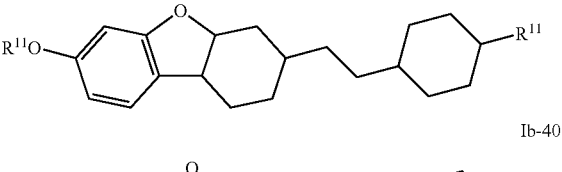
Ib-39
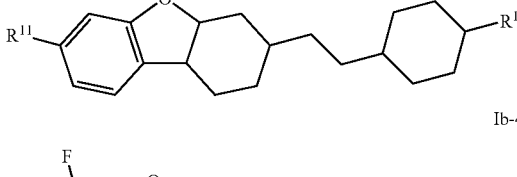
Ib-40
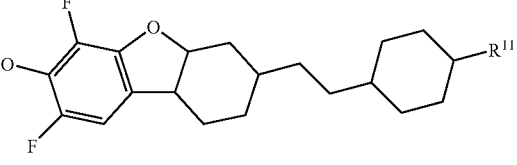
Ib-41
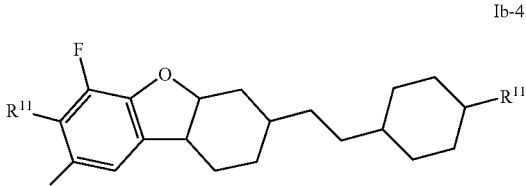
Ib-42

-continued
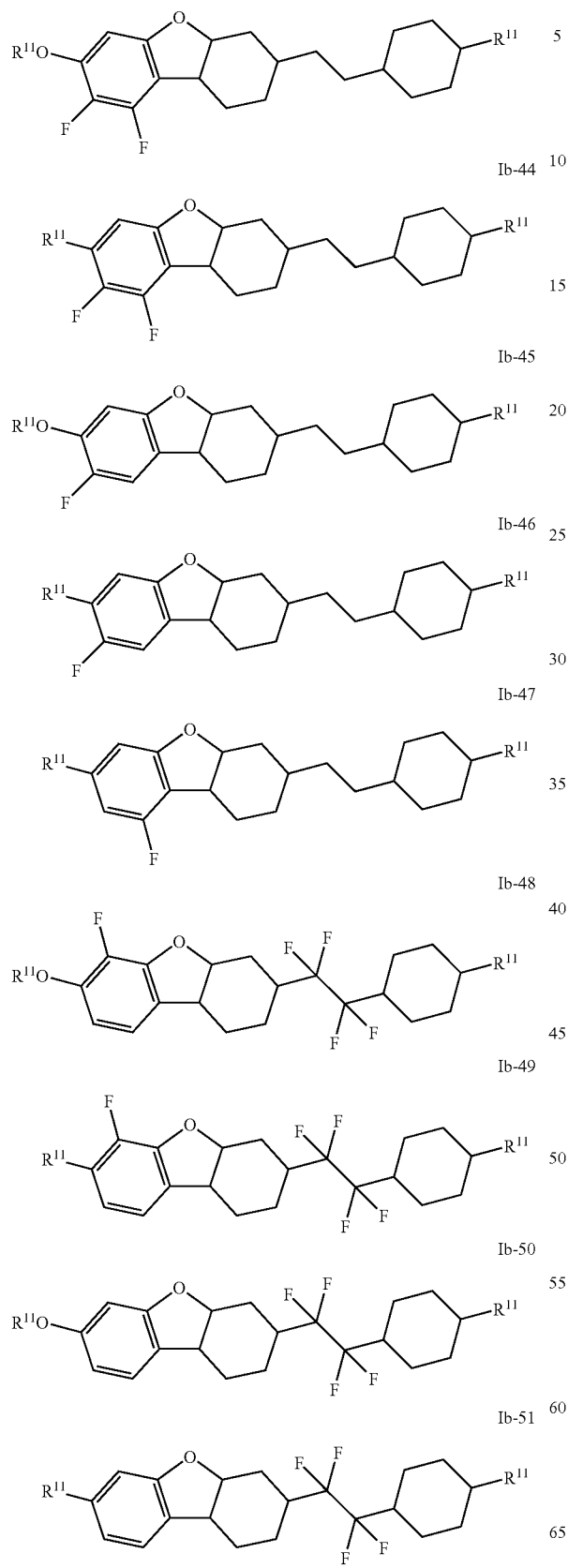
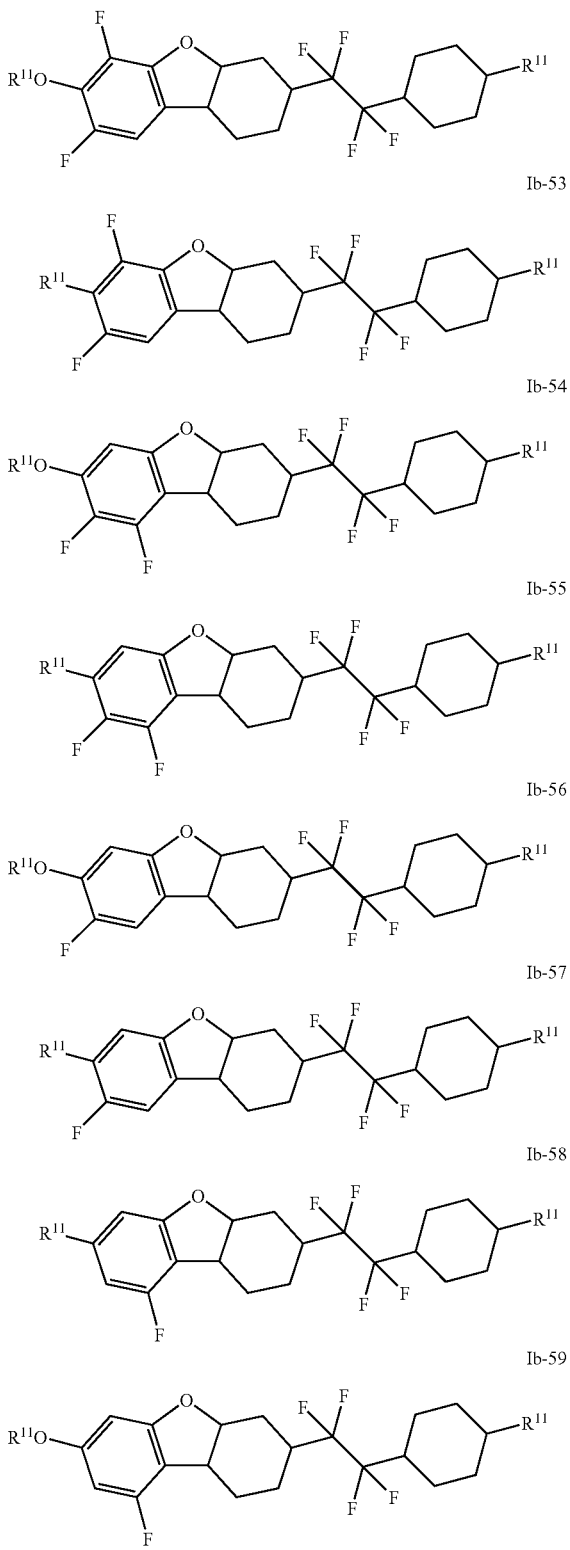
in which
p in each case, independently of one another, is 0 to 4, preferably 0, 1 or 2, and $R^{11}$ and $R^{22}$ have the same meanings as defined above.

Of the compounds 1b, particular preference is given to those containing a cyclohexyl ring.

Above and below, the moiety

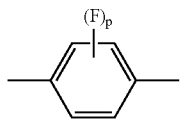

in the sub-formulae preferably denotes a moiety of the formula

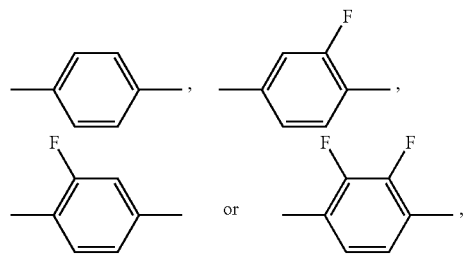

If p in the formulae occurs more than once, it may in each case have identical or different meanings.

Of the preferred compounds of the formula Ic according to the invention, particular preference is given to the following:

Ic-1
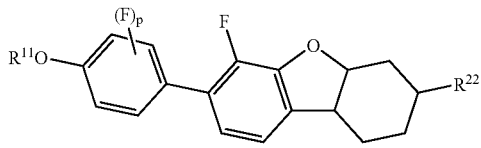

Ic-2
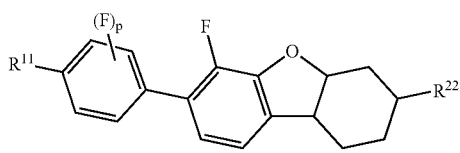

Ic-3
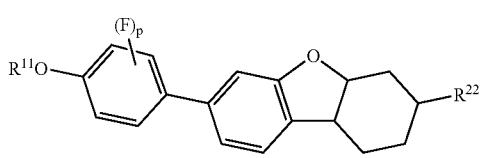

Ic-4
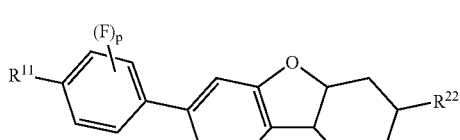

Ic-5
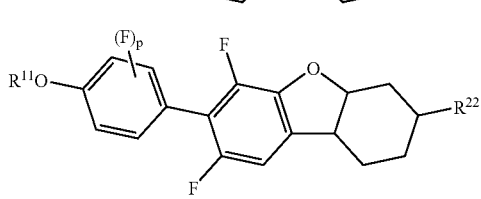

-continued

Ic-6
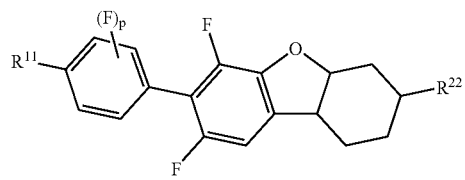

Ic-7
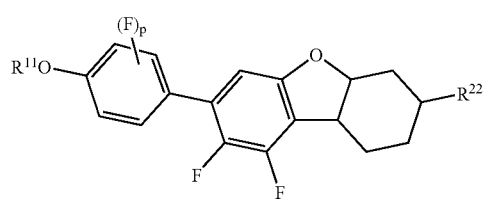

Ic-8
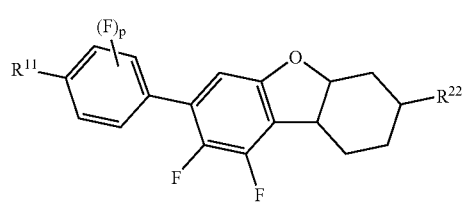

Ic-9
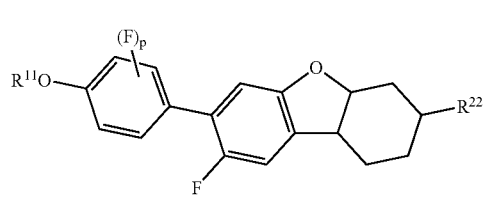

Ic-10
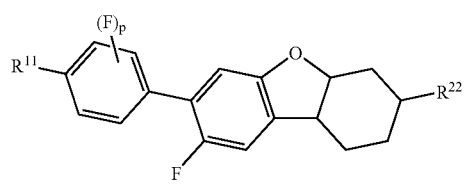

Ic-11
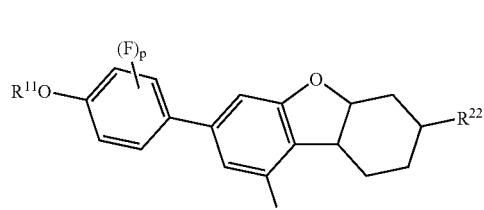

Ic-12
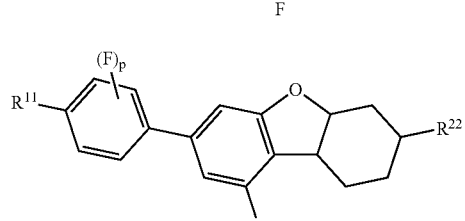

Ic-13
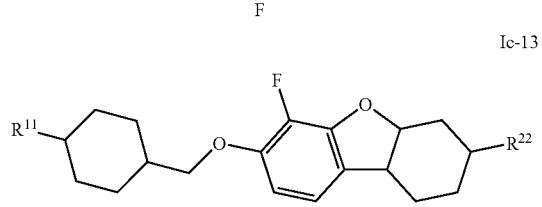

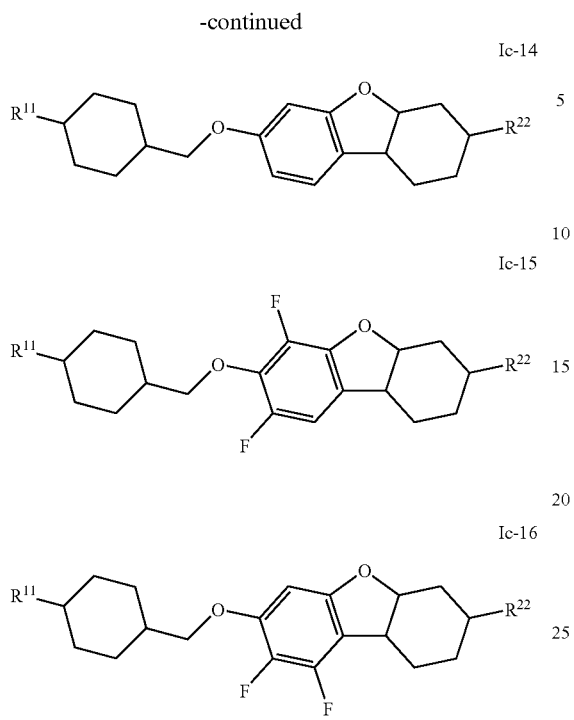
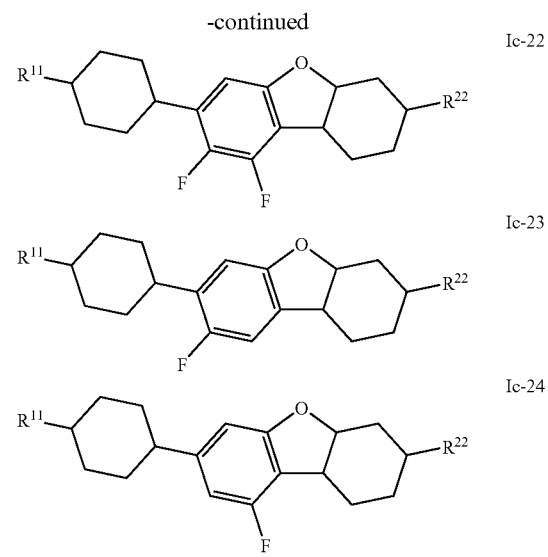
in which
R[11], R[22] and p have the same meanings as defined above.
Of the compounds of the formulae Ic1-Ic24, compounds of the formulae containing an unsubstituted or substituted 1,4-phenylene ring and the compound 1c-13 are most preferred.
Of the preferred compounds of the formula Id according to the invention, particular preference is given to the following:
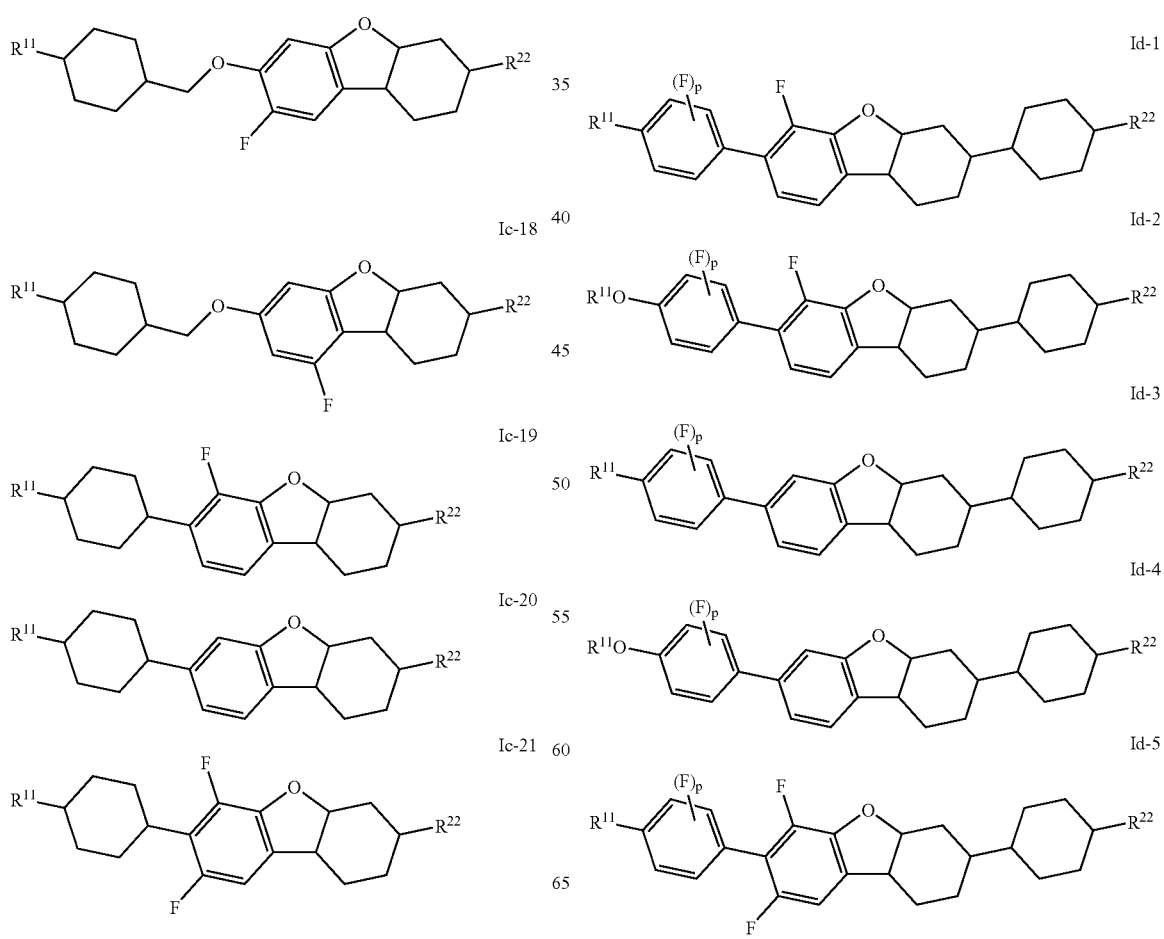

-continued
Id-6
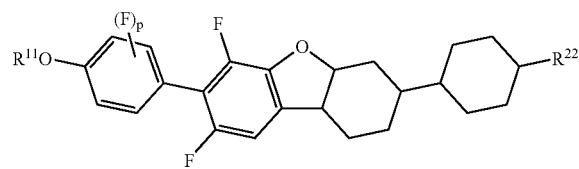
Id-7
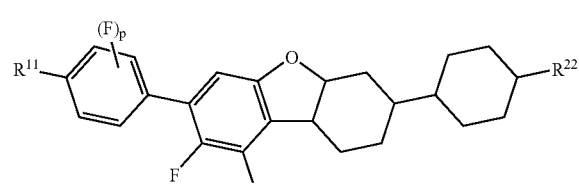
Id-8
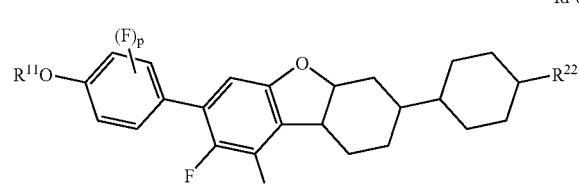
Id-9
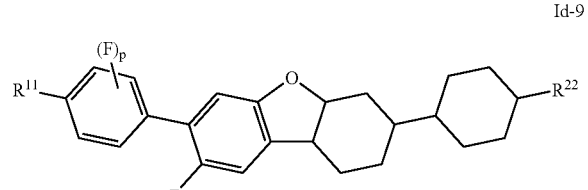
Id-10
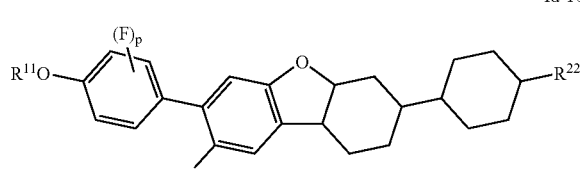
Id-11
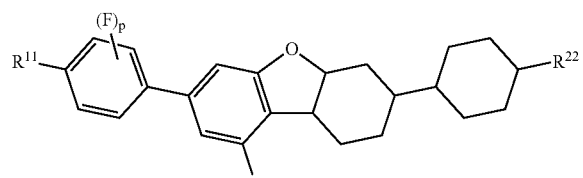
Id-12
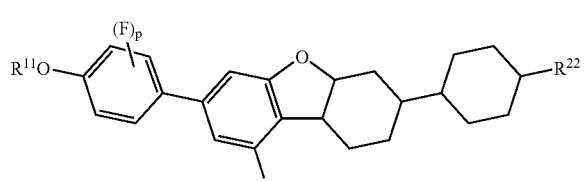
Id-13
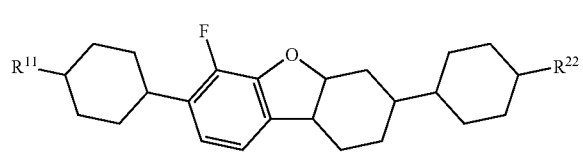
-continued
Id-14
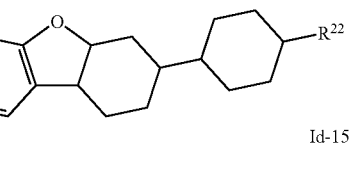
Id-15
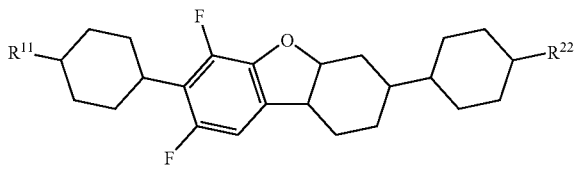
Id-16
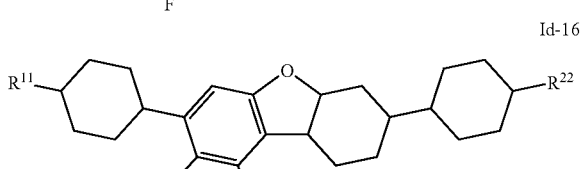
Id-17
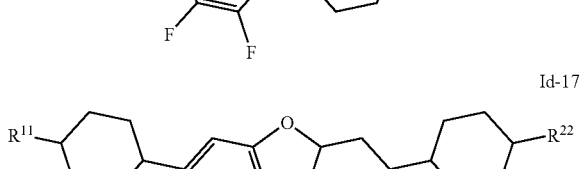
Id-18
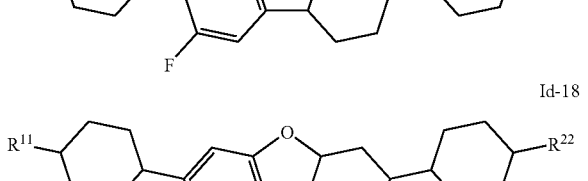
Id-19
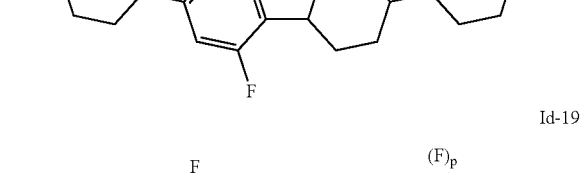
Id-20
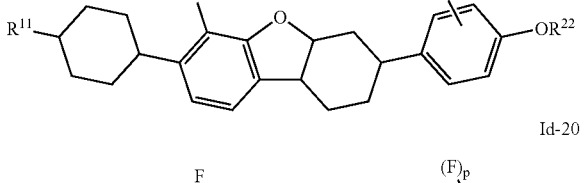
Id-21
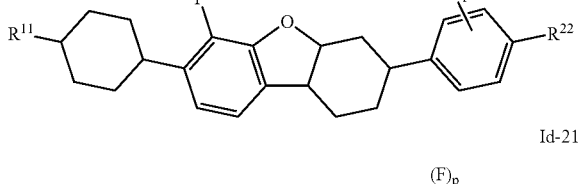
Id-22
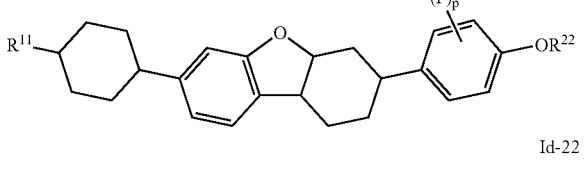

-continued
Id-23
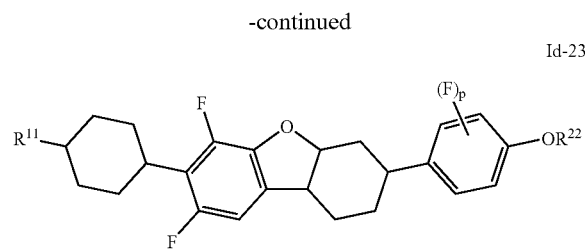
Id-24
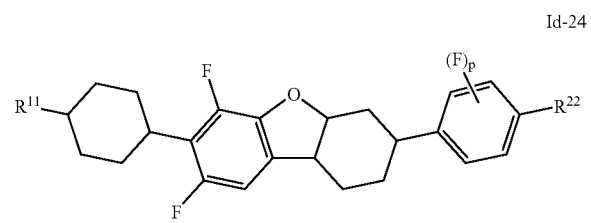
Id-25
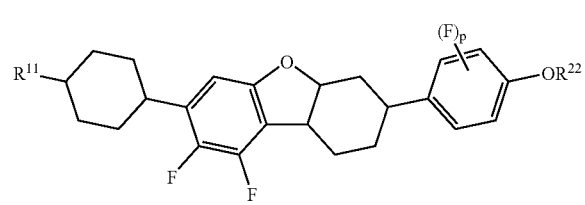
Id-26
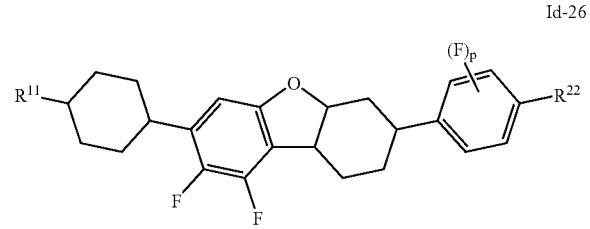
Id-27
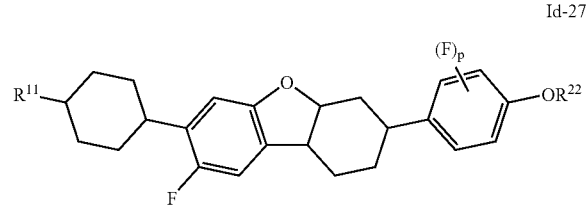
Id-28
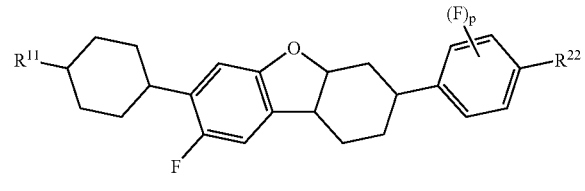
-continued
Id-29
Id-30
Id-31
Id-32
Id-33
Id-34
Id-35
Id-36
Id-37
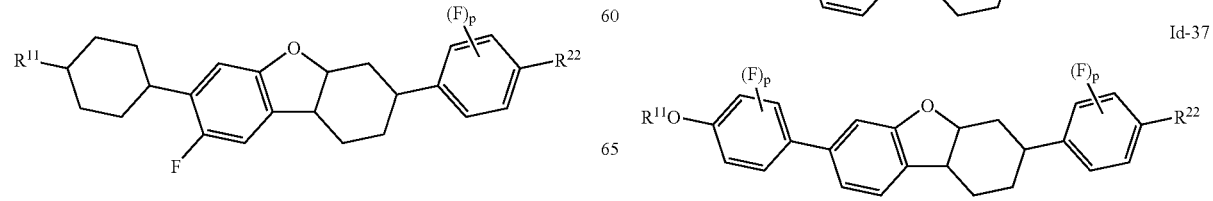

-continued
Id-38
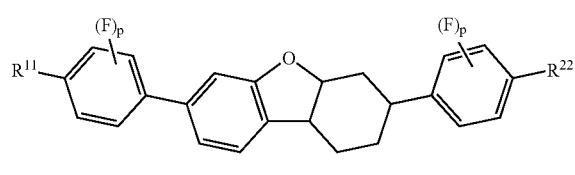
Id-39
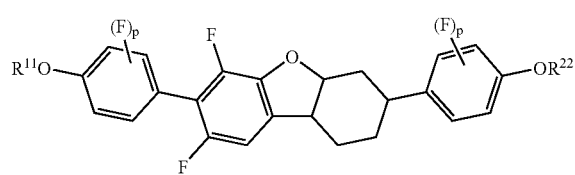
Id-40
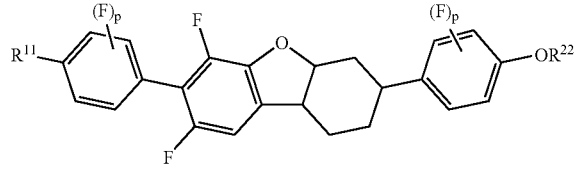
Id-41
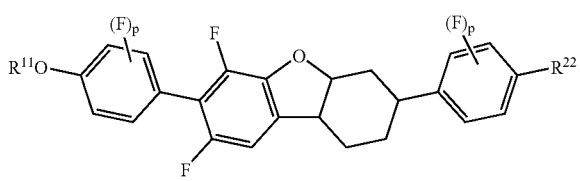
Id-42
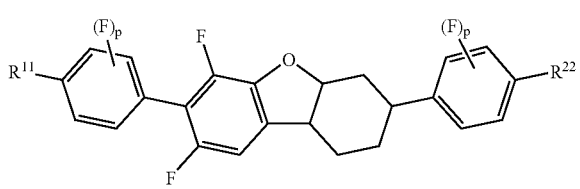
Id-43
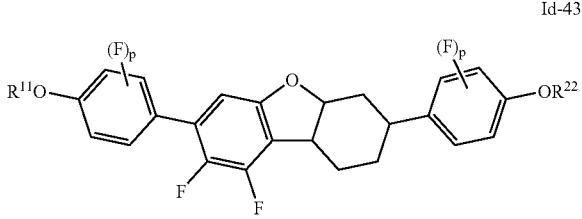
-continued
Id-44
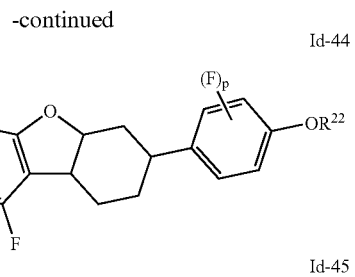
Id-45
Id-46
Id-47
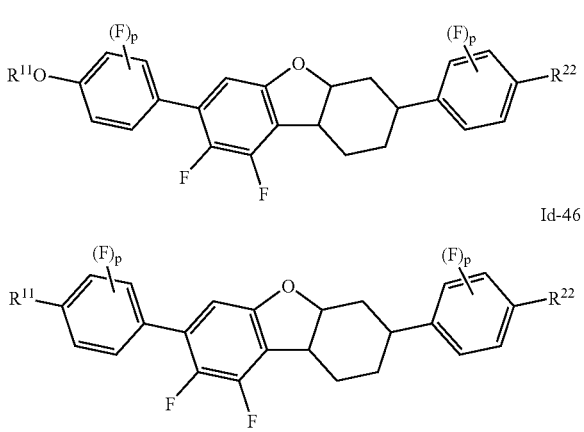
Id-48
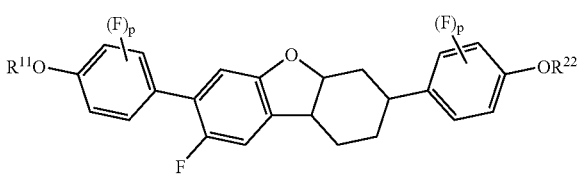
Id-49
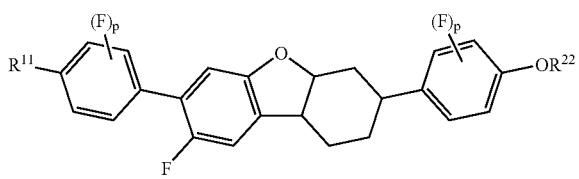
Id-50
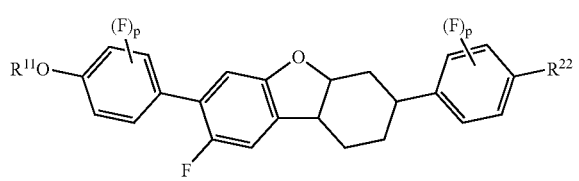
Id-51
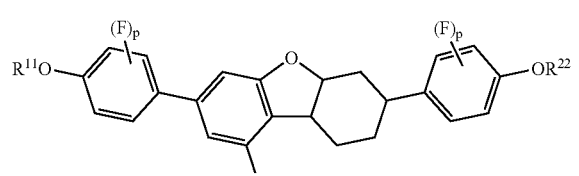

-continued
Id-52
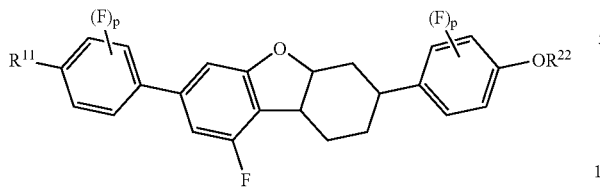
Id-60
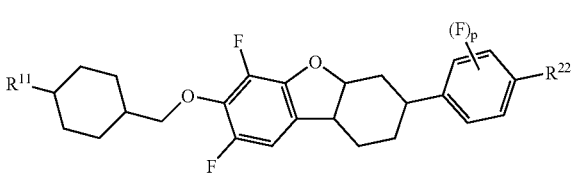
Id-53
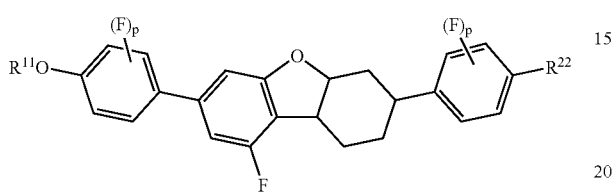
Id-61
Id-54
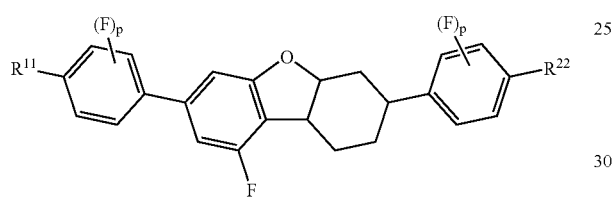
Id-62
Id-55
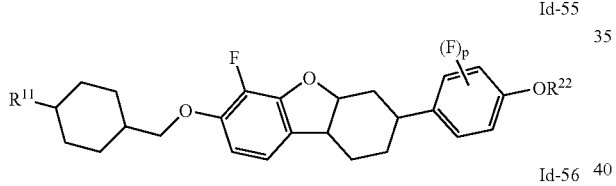
Id-63
Id-56
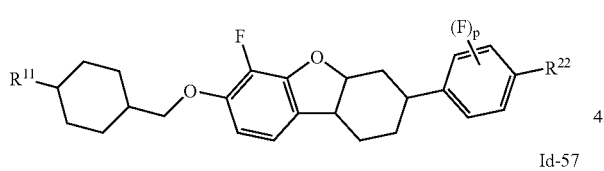
Id-64
Id-57
Id-65
Id-58
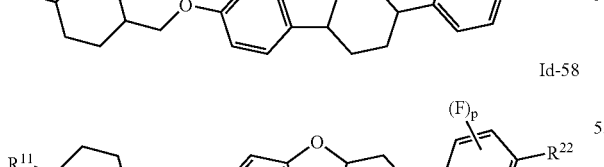
Id-66
Id-59
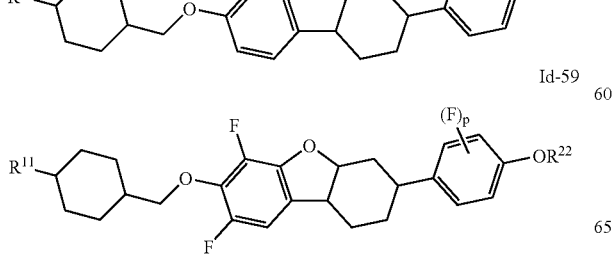

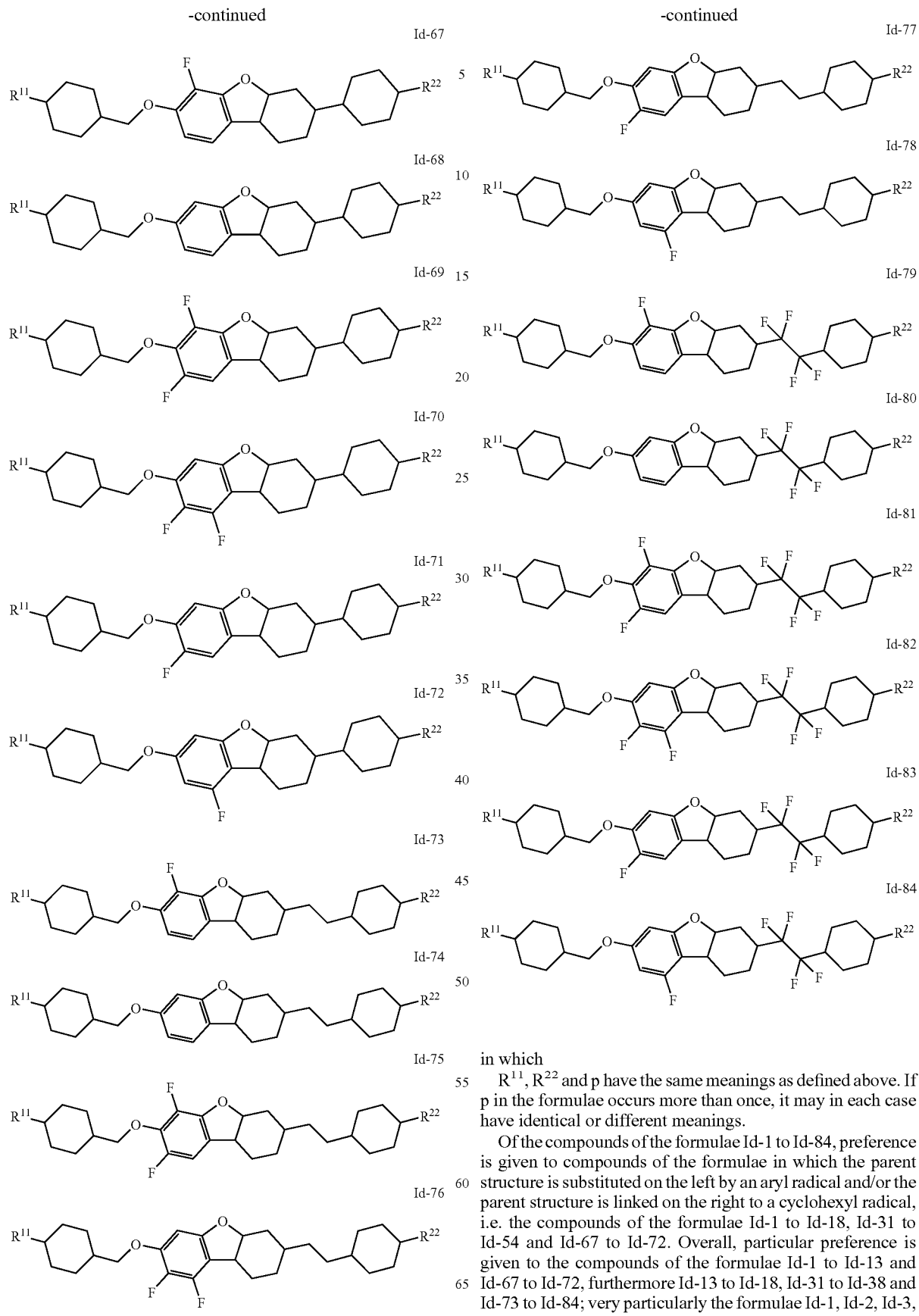

in which $R^{11}$, $R^{22}$ and p have the same meanings as defined above. If p in the formulae occurs more than once, it may in each case have identical or different meanings.

Of the compounds of the formulae Id-1 to Id-84, preference is given to compounds of the formulae in which the parent structure is substituted on the left by an aryl radical and/or the parent structure is linked on the right to a cyclohexyl radical, i.e. the compounds of the formulae Id-1 to Id-18, Id-31 to Id-54 and Id-67 to Id-72. Overall, particular preference is given to the compounds of the formulae Id-1 to Id-13 and Id-67 to Id-72, furthermore Id-13 to Id-18, Id-31 to Id-38 and Id-73 to Id-84; very particularly the formulae Id-1, Id-2, Id-3, Id-4, Id-67 and Id-68.

Of the preferred compounds of the formula Ie according to the invention, particular preference is given to the following:
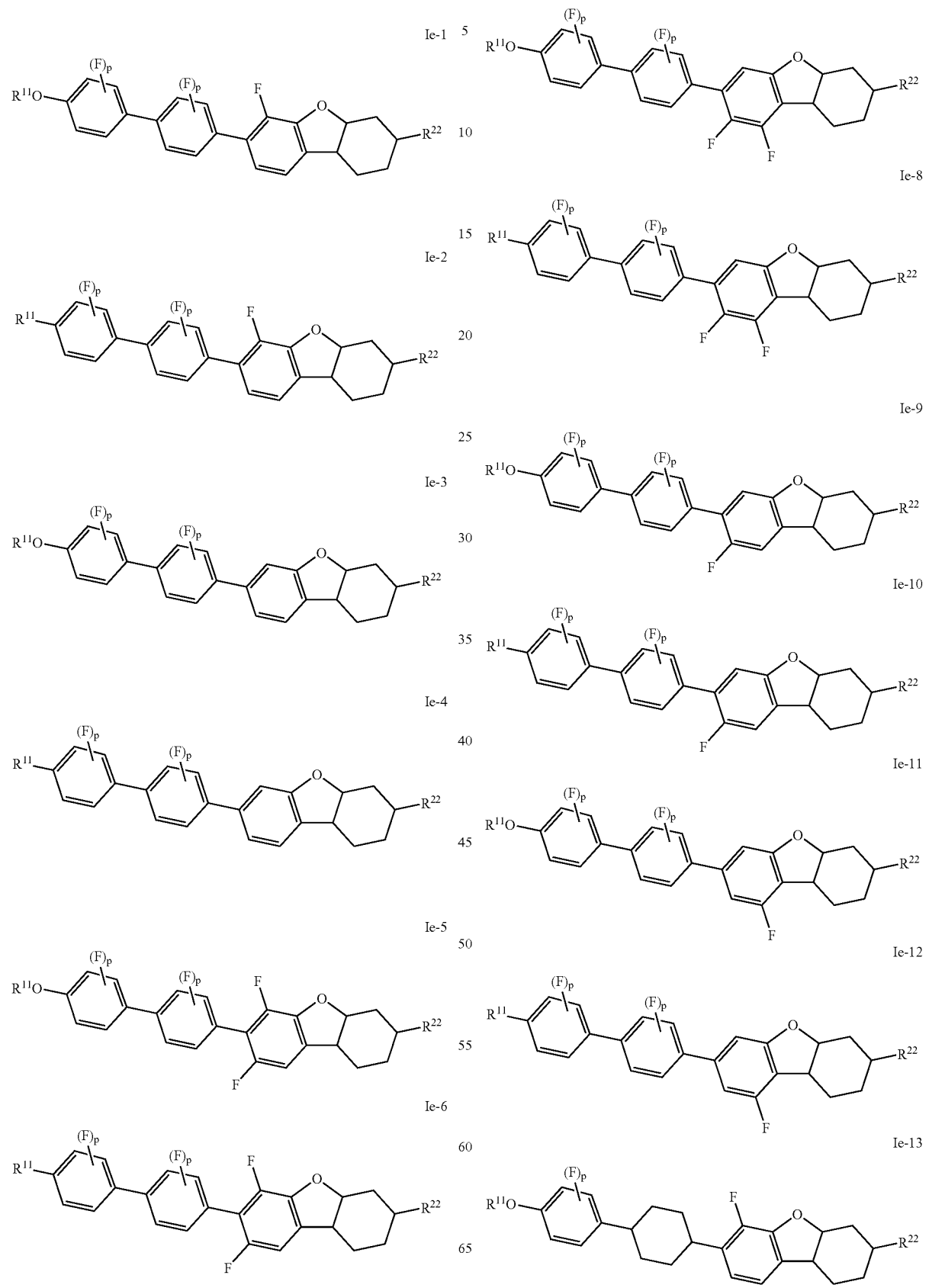

-continued
Ie-14
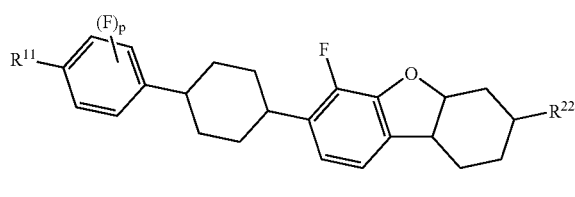
Ie-15
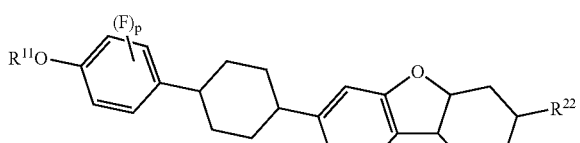
Ie-16
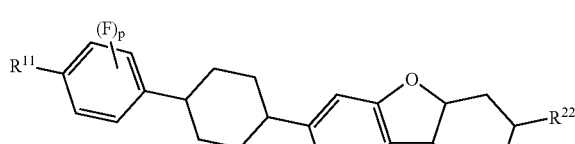
Ie-17
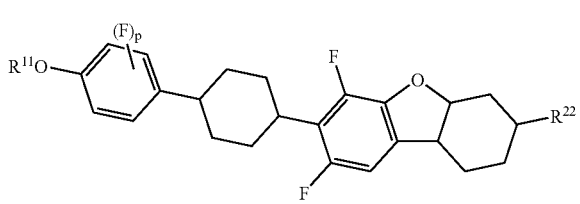
Ie-18
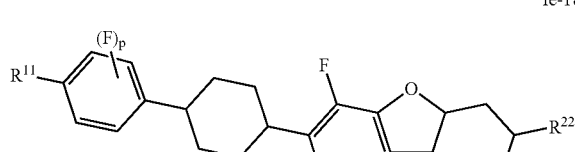
Ie-19
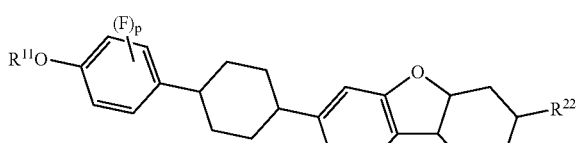
Ie-20
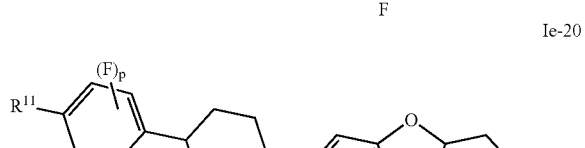
-continued
Ie-21
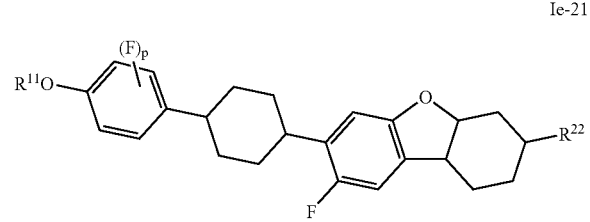
Ie-22
Ie-23
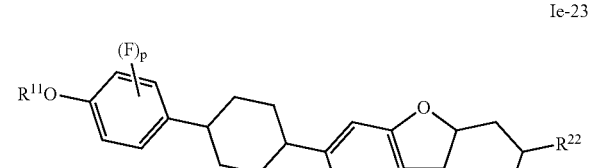
Ie-24
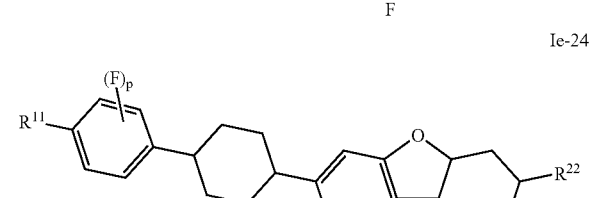
Ie-25
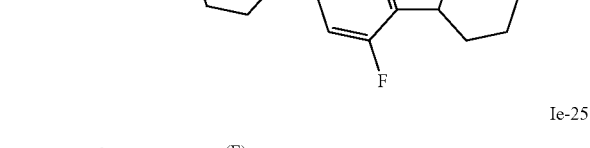
Ie-26
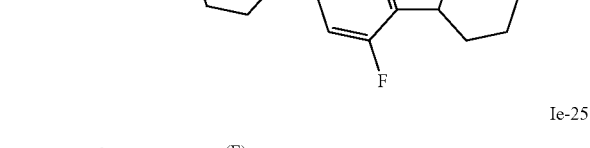
Ie-27
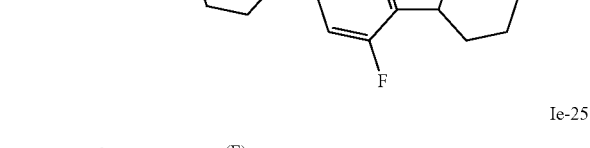

Ie-28
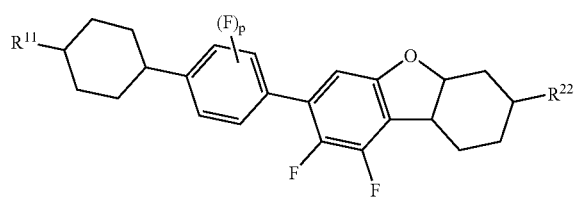

Ie-29
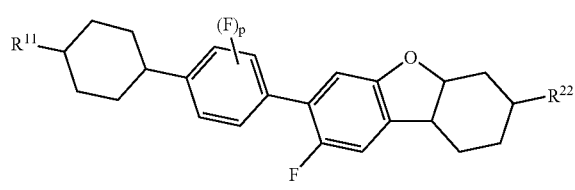

Ie-30
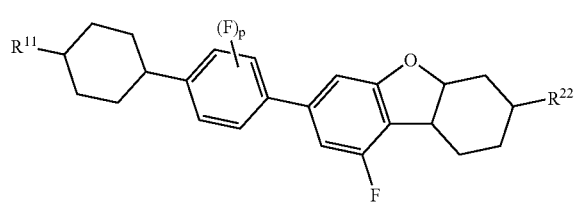

Ie-31
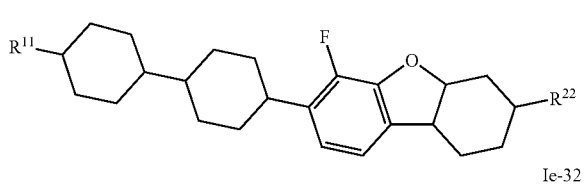

Ie-32
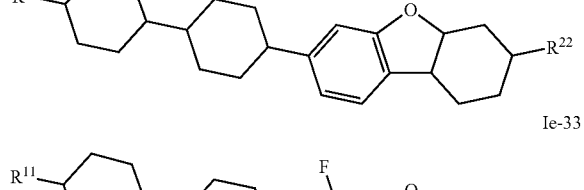

Ie-33
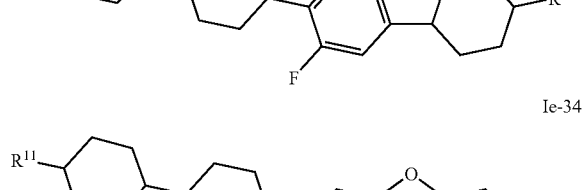

Ie-34
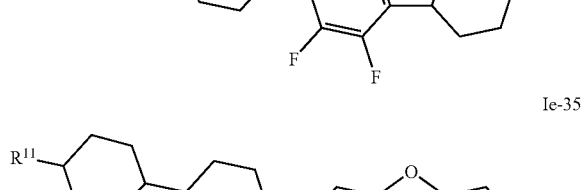

Ie-35
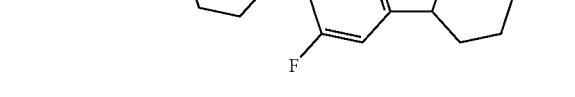

Ie-36
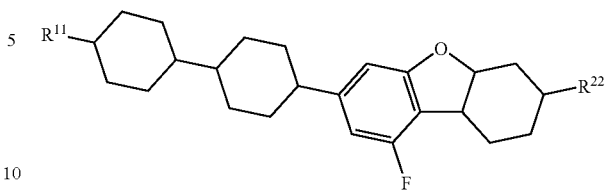

Ie-37
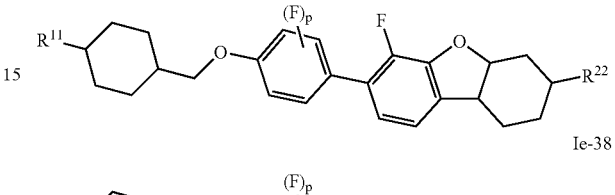

Ie-38
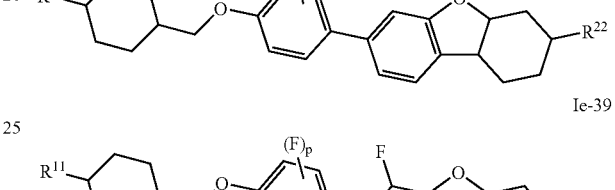

Ie-39
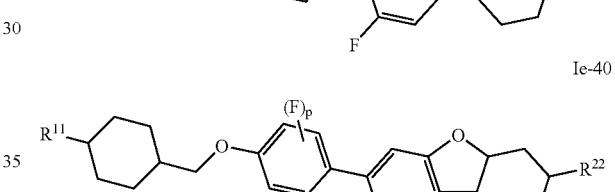

Ie-40
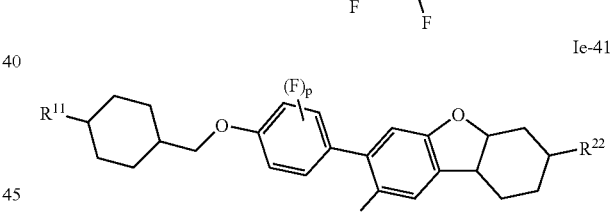

Ie-41
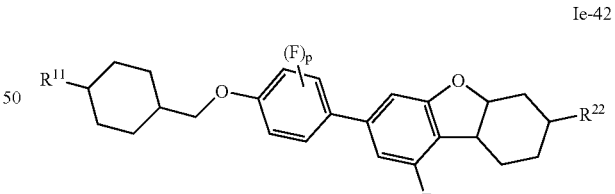

Ie-42
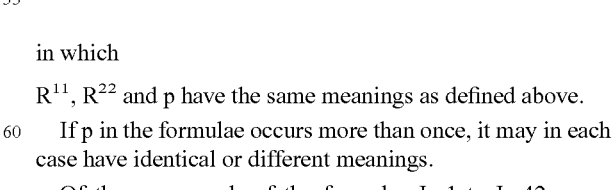

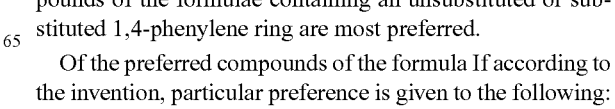

in which $R^{11}$, $R^{22}$ and p have the same meanings as defined above.

If p in the formulae occurs more than once, it may in each case have identical or different meanings.

Of the compounds of the formulae Ie-1 to Ie-42, compounds of the formulae containing an unsubstituted or substituted 1,4-phenylene ring are most preferred.

Of the preferred compounds of the formula If according to the invention, particular preference is given to the following:

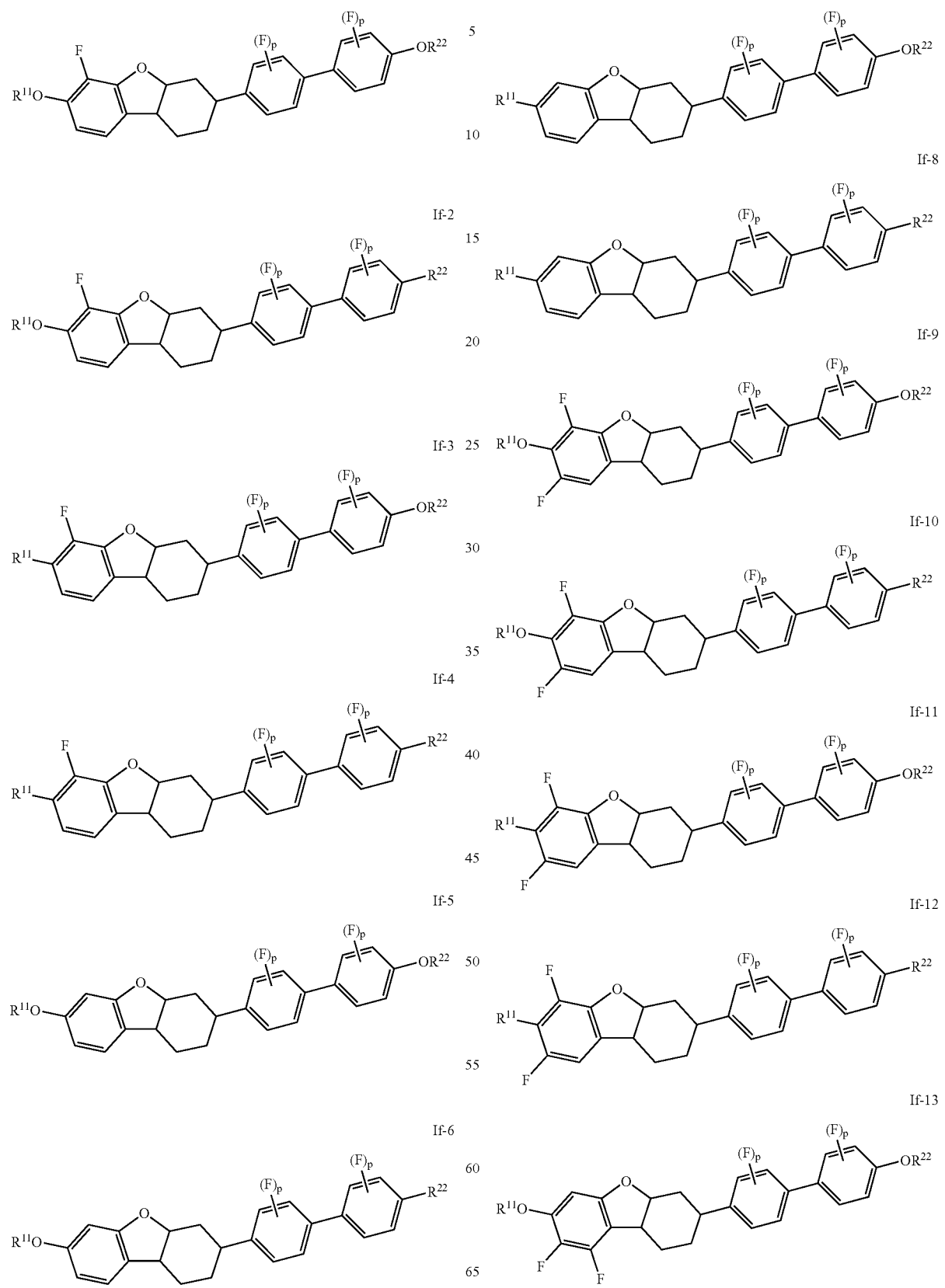

-continued
If-14
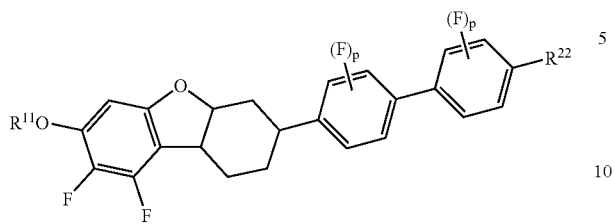
If-15
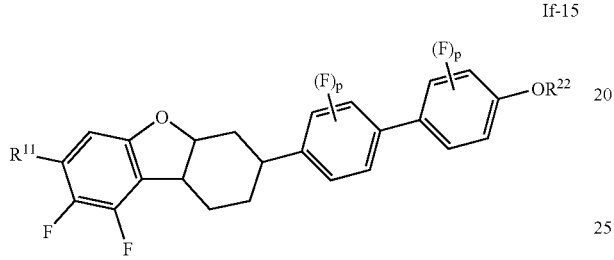
If-16
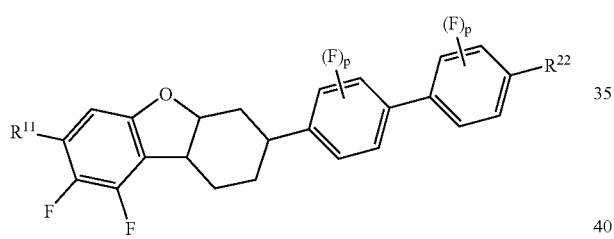
If-17
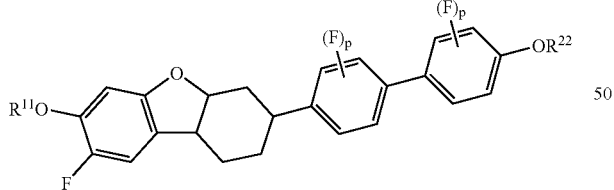
If-18
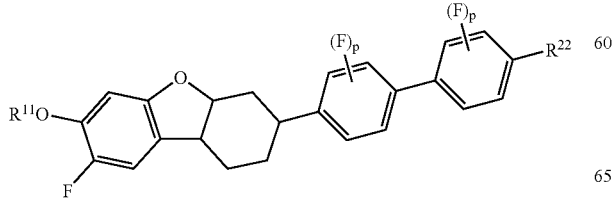
-continued
If-20
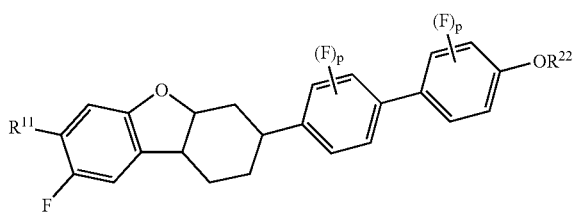
If-21
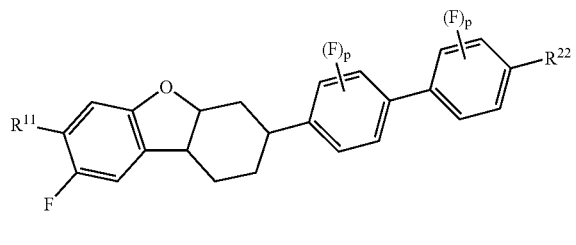
If-22
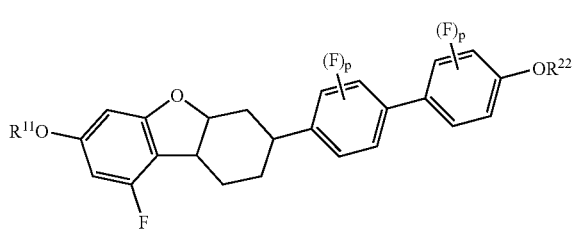
If-23
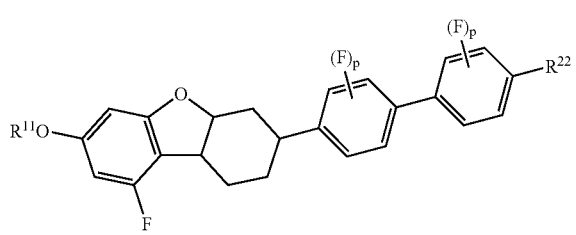
If-24
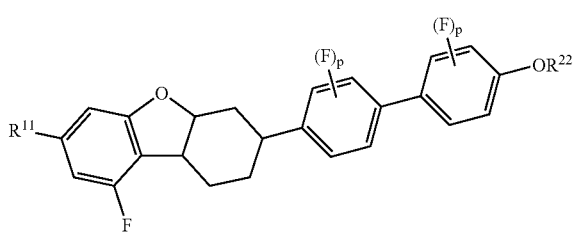

If-25
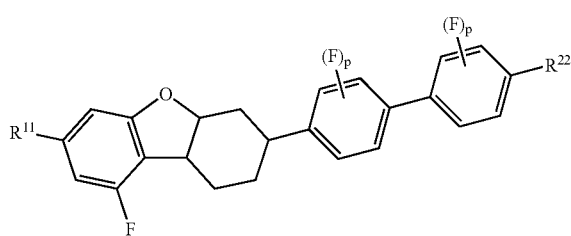
If-26
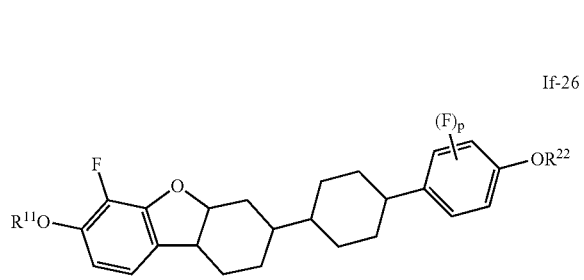
If-27
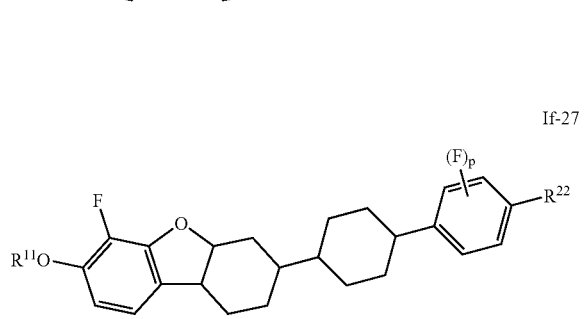
If-28
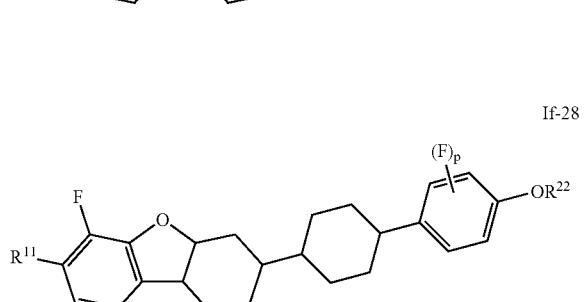
If-29
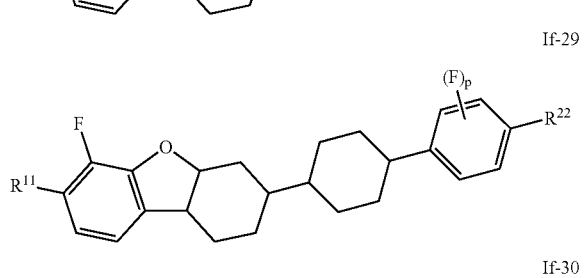
If-30
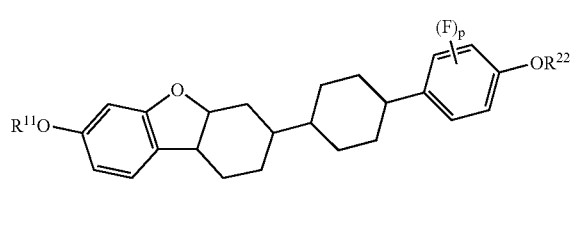
If-31
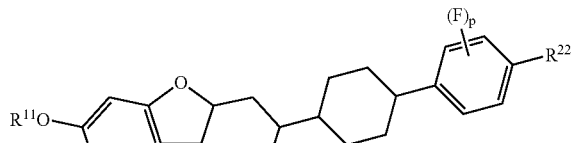
If-32
If-33
If-34
If-35
If-36
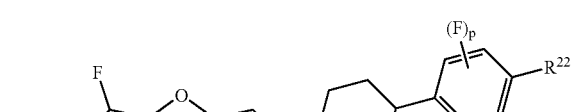
If-37

If-38
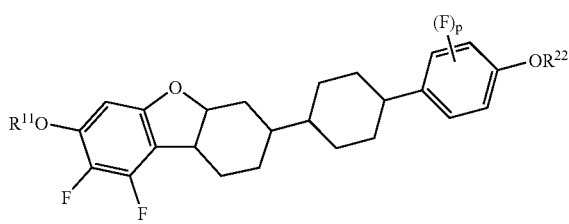
If-44
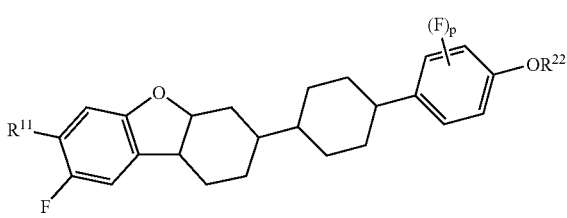
If-39
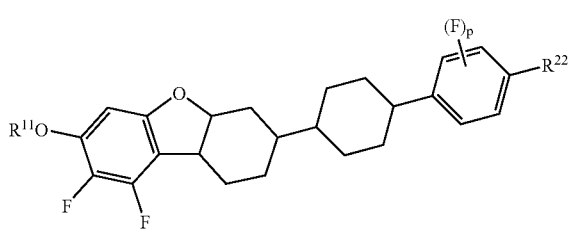
If-45
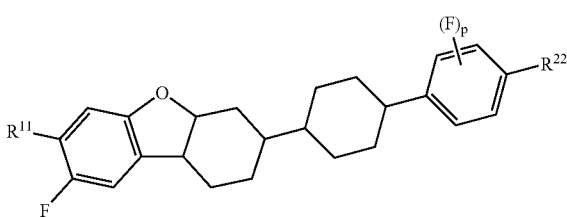
If-40
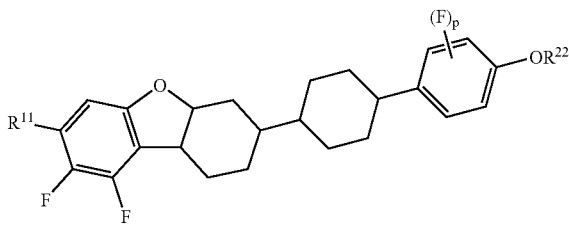
If-46
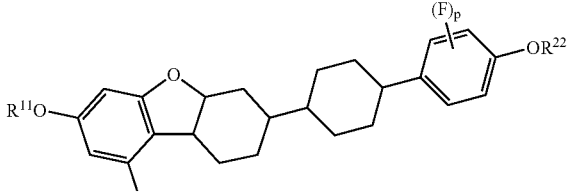
If-41
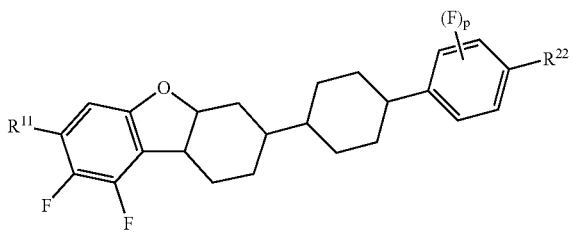
If-47
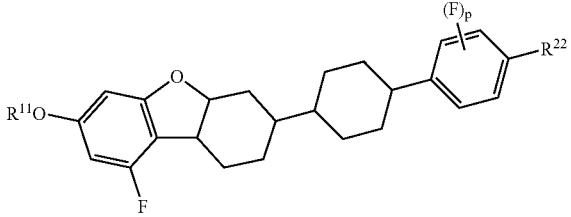
If-42
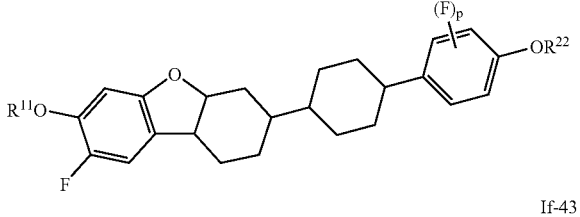
If-48
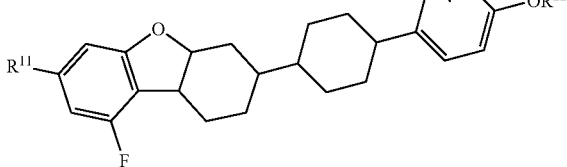
If-43
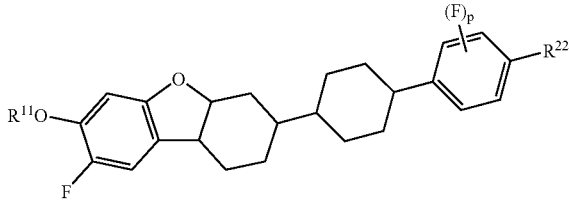
If-49
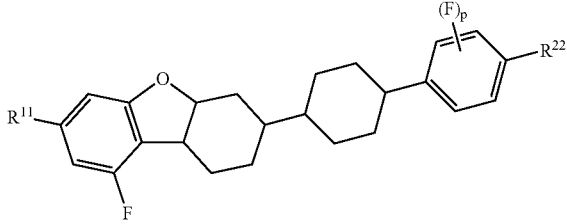

-continued
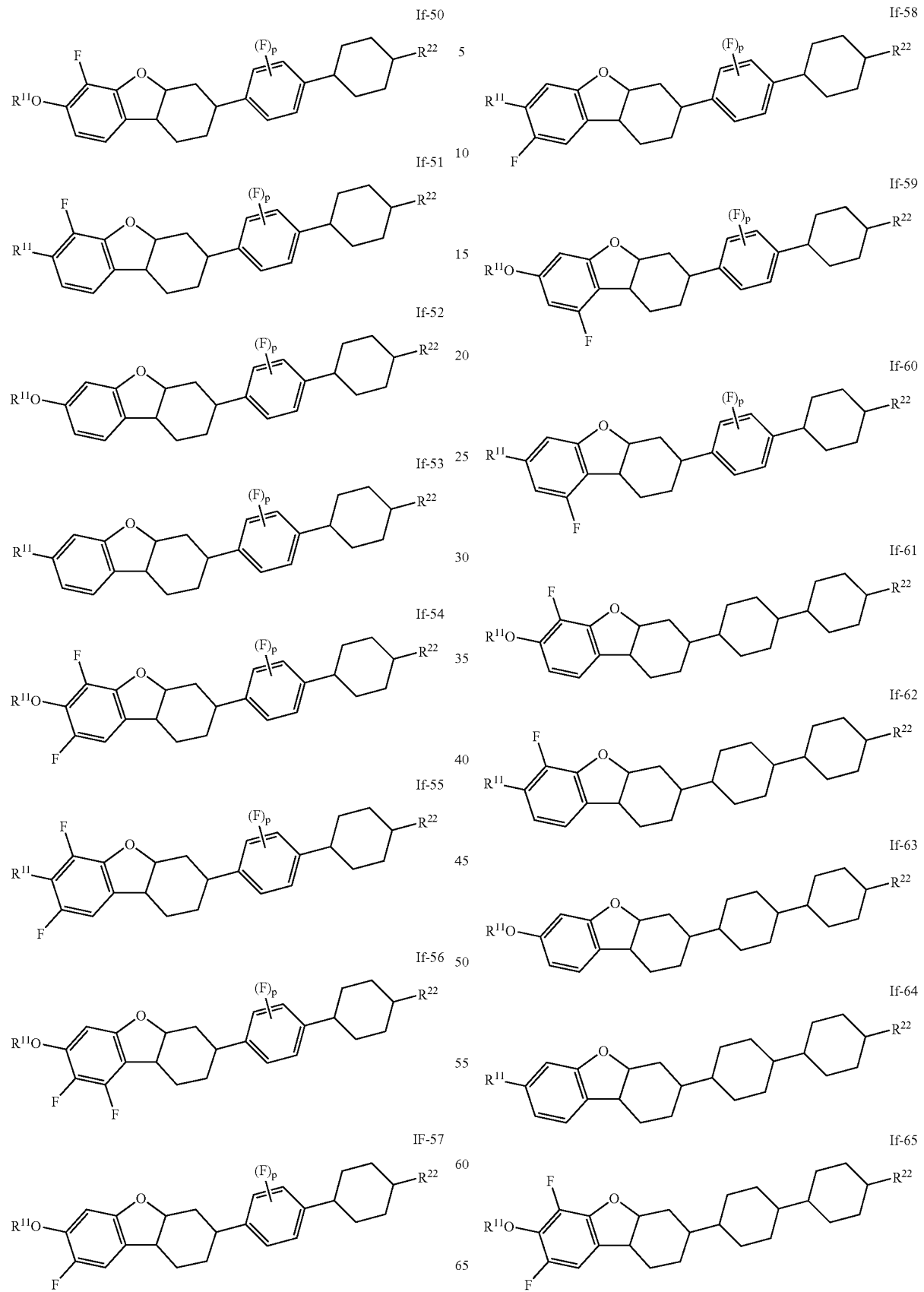

-continued
If-66
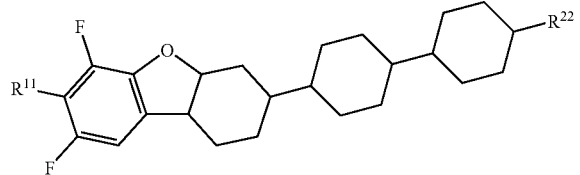
If-67
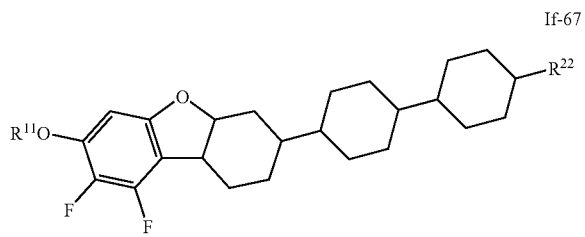
If-68
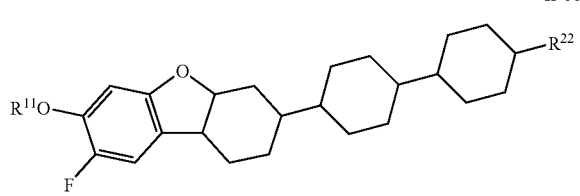
If-69
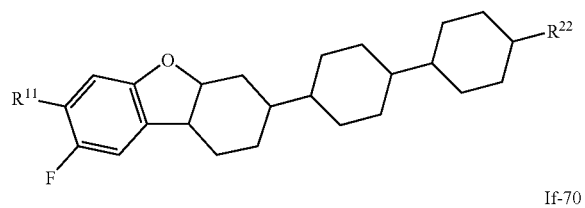
If-70
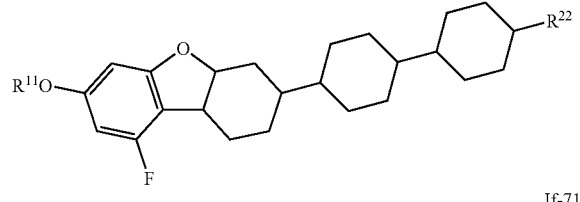
If-71
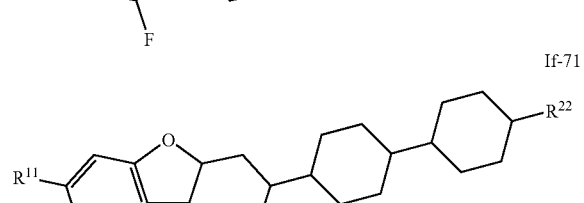
If-72
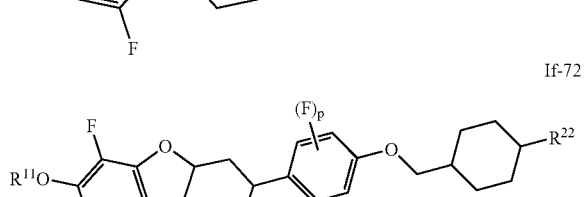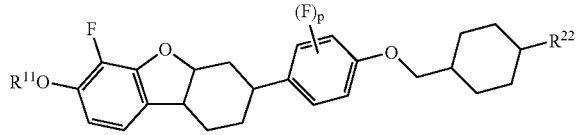
-continued
If-73
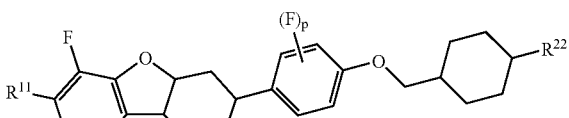
If-74
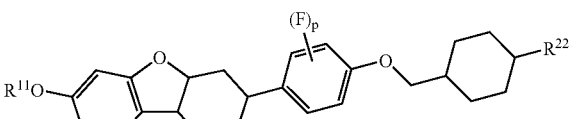
If-75
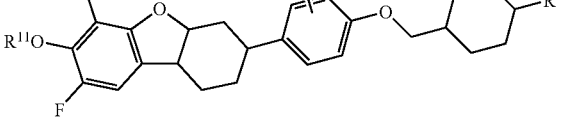
If-76
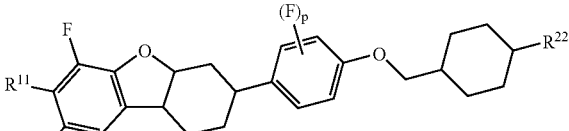
If-77
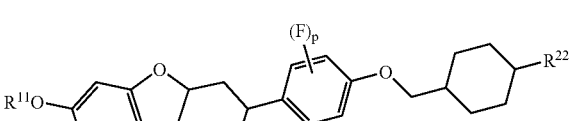
If-78
If-79
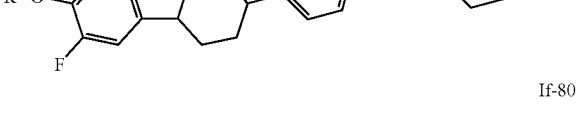
If-80
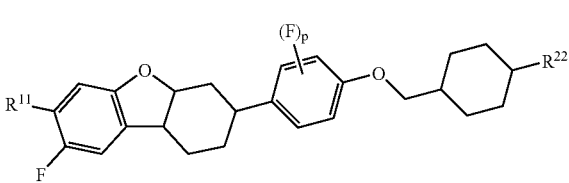

The 1,4-substituted cyclohexyl ring of the formula

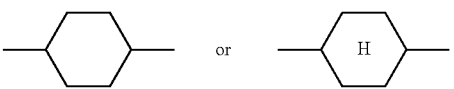

in the compounds according to the invention and in the other components of liquid-crystalline media preferably has the trans configuration, i.e. the two substituents are both in the equatorial position in the thermodynamically preferred chair conformation.

Synthesis of the Compounds:

The compounds of the general formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

If desired, the starting materials can also be formed in situ by not isolating them from the reaction mixture, but instead immediately converting them further into the compounds of the general formula I.

The syntheses of various compounds of the general formula I according to the invention are described by way of example in the examples. The starting substances can be obtained by generally accessible literature procedures or are commercially available. The reaction types described are to be regarded as known from the literature.

The compounds of the formula I encompass all eight stereoisomers which emanate from the possible configurations of the hexahydrobenzofuran ring with respect to positions 3, 4a and 9b of the ring system of the general formula:

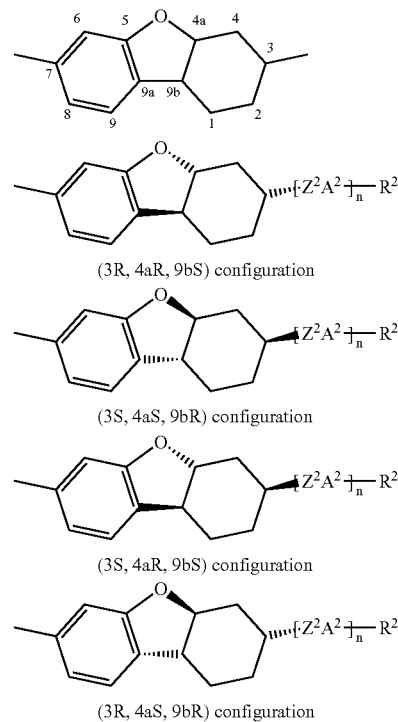

(3R, 4aR, 9bS) configuration (3S, 4aS, 9bR) configuration (3S, 4aR, 9bS) configuration (3R, 4aS, 9bR) configuration -continued If-81

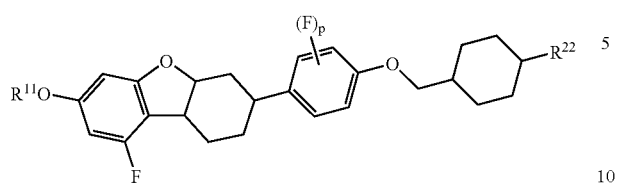

If-82

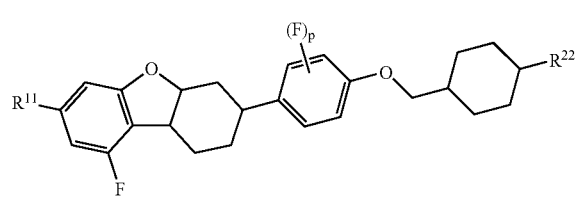

in which
$R^{11}$, $R^{22}$ and p have the same meanings as defined above. If p in the formulae occurs more than once, it may in each case have identical or different meanings.

Of the compounds of the formulae If-1 to If-82, the compounds of the formulae containing at least one 1,4-cyclohexylene ring are most preferred, in particular containing two cyclohexylene rings (If-61 to If-71) or containing one cyclohexylene ring directly on the parent structure (If-26 to If-49). Particular preference is given to compounds of the formula If-61.

In the sub-formulae of the formulae Ia to Ih, the moiety

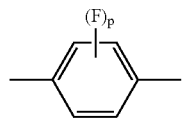

preferably denotes a moiety of the formula

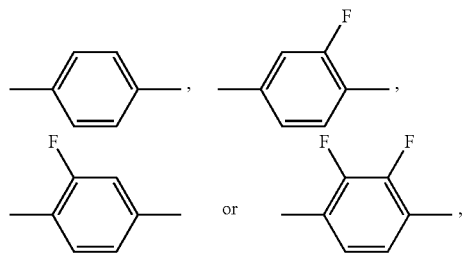

If radicals or substituents of the compounds according to the invention or the compounds according to the invention themselves are in the form of optically active or stereoisomeric radicals, substituents or compounds since they have, for example, a centre of asymmetry, these are likewise encompassed by the present invention. It goes without saying here that the compounds of the general formula I according to the invention may exist in isomerically pure form, for example as pure enantiomers, diastereomers, E or Z isomers, trans or cis isomers, or as a mixture of a plurality of isomers in any desired ratio, for example as a racemate, E/Z isomer mixture or as a cis/trans isomer mixture.

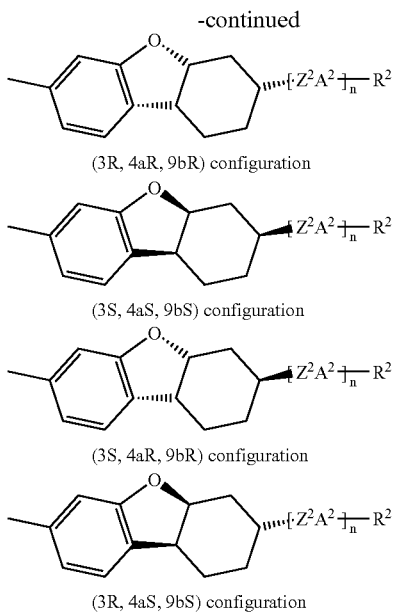

(3R, 4aR, 9bR) configuration (3S, 4aS, 9bS) configuration (3S, 4aR, 9bR) configuration (3R, 4aS, 9bS) configuration Particular preference is given to the stereoisomers in which a trans link of the O-heterocyclic ring system to the cyclohexane ring is present and at the same time the substituent on C-3 is arranged in the trans configuration to the substituent on C-9b (the furan ring here is regarded as a substituent of the cyclohexane ring). This applies to the particularly preferred stereoisomers having the relative (3R*, 4aR*, 9bS*)-configuration. The asterisk stands for the relative configuration, which has the same meaning as the two mirror-image, absolute configurations.

Due to this stereochemistry, the ring system takes on a flat geometry and the entire molecule takes on a more stretched shape.

A part-aspect of the invention relates to processes for the preparation of the compounds of the formula I according to the invention. The processes are subject to a common synthesis strategy, which is explained below.

A preferred process for the preparation of compounds of type 1, which are analogous to compounds of the formula I, is depicted in Scheme 1. The synthesis can be matched to the compounds of the formula 1 desired in each case through the choice of suitable starting materials 3 and 4. These starting materials are either commercially available or they can be synthesised following processes which have already been published.

Scheme 1: Synthesis of compounds 1.

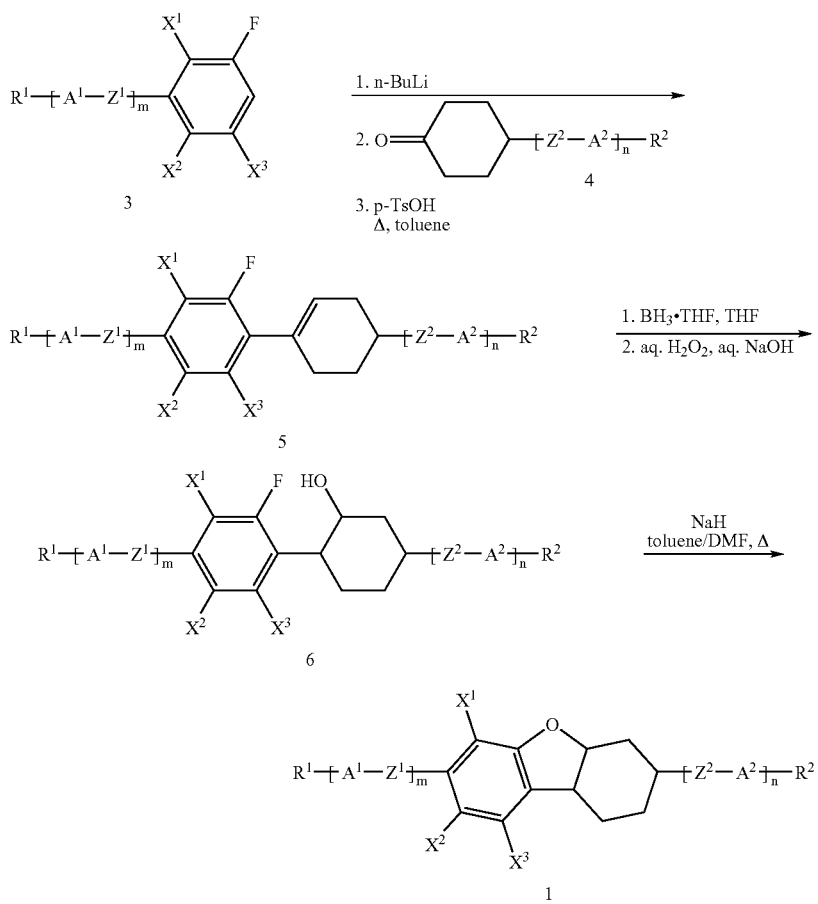

The organolithium derivative of compound 3 adds onto the cyclohexyl ketone 4. The resultant alcohol readily dehydrates on treatment with p-TsOH to give the cyclohexene 5 analogously to P. Kirsch et al., Angew. Chem. Int. Ed. (1998), 37, 484-489. Hydroboration oxidation of the double bond using BH$_3$/THF complex gives the secondary alcohol 6. The alkoxide of compound 6 cyclises under the reaction conditions indicated to give the target compound 1. Conventional laboratory separation and purification methods give the particularly preferred (3R*, 4aR*, 9bS*)-configured stereoisomers of the compounds of the formula 1.

Preference is likewise given to synthetic processes via the keto intermediate II, since compound 11 can be functionalised in different ways below. The synthesis of the ketone 11 is likewise carried out via the reaction sequence depicted in Scheme 1 using 1,4-cyclohexanedione monoethylene ketal 7 as starting material (cf. Scheme 2). After the ring-closure reaction to give 10, the ketal protecting group is cleaved off in acidic medium (cf. Kirsch et al.).

-continued

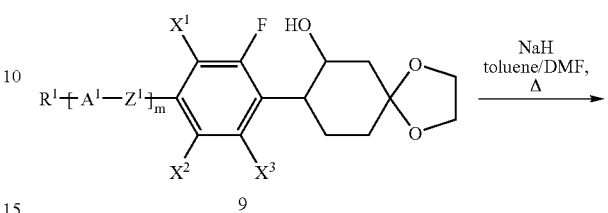

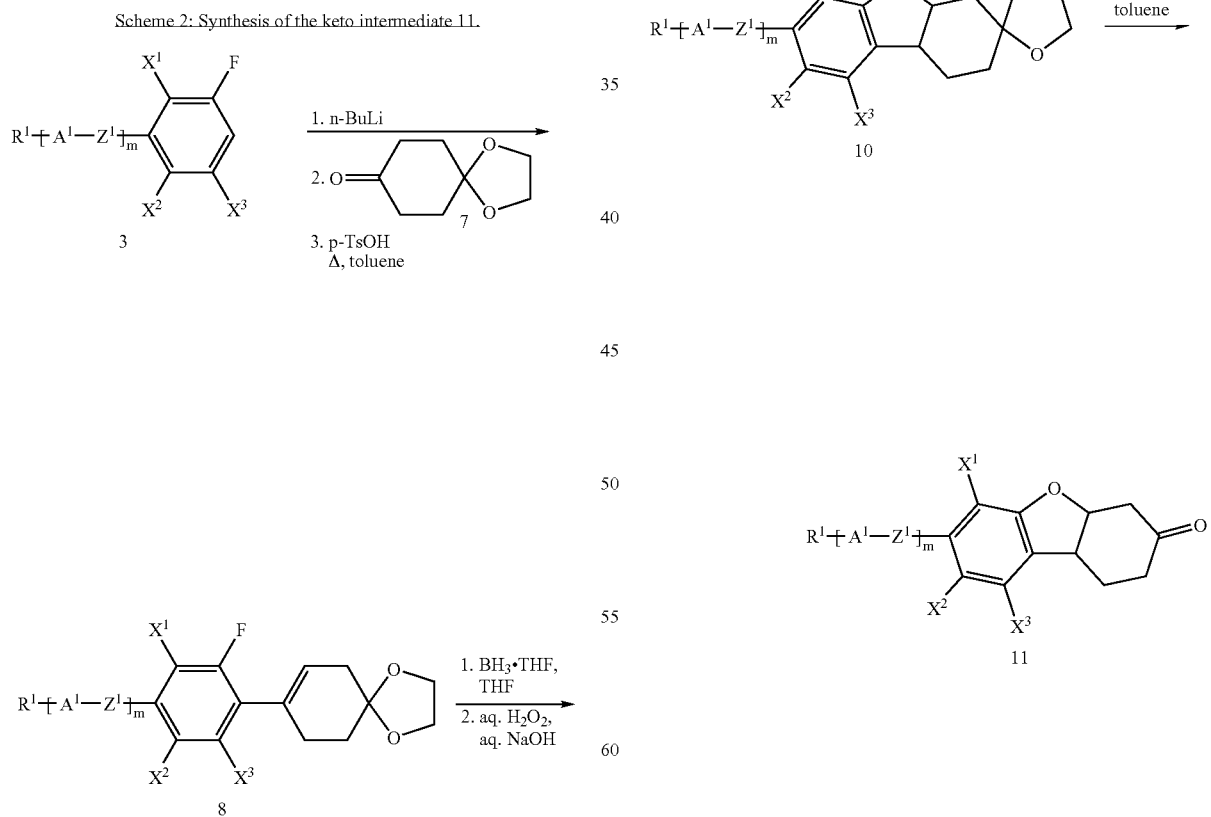

The further functionalisation of 11 can then be carried out in various ways (cf. Scheme 3 and Scheme 4).

Scheme 3: Functionalisation by reaction with Grignard reagents.

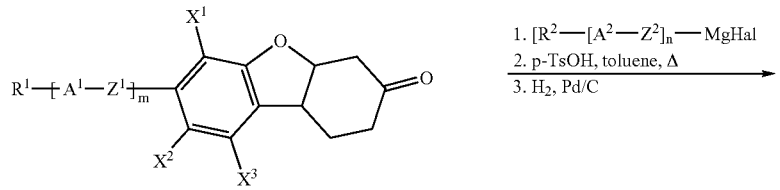

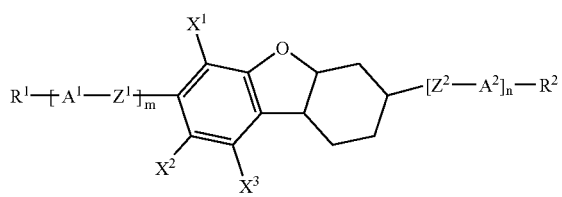

The reaction of 11 with a suitable Grignard reagent (cf. Scheme 3) or an organolithium compound and dehydration of the resultant alcohol and final catalytic hydrogenation gives the target compound 12. The preferred (3R*,4aR*, 9bS-configured stereoisomers of compound 12 are obtained via conventional laboratory separation methods.

Wittig olefin formation reactions are furthermore suitable for derivatisation (cf. Scheme 4). After reaction with Wittig reagents and subsequent hydrogenation of the double bond formed, a separable isomer mixture of the target compound 13 is again formed.

Scheme 4: Functionalisation of 11 by Wittig olefin formation.

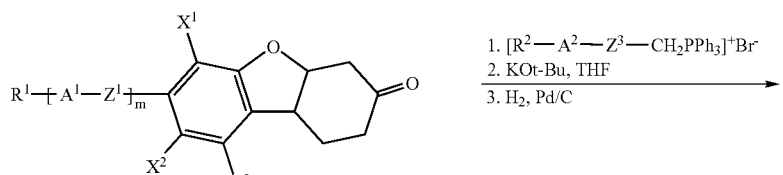

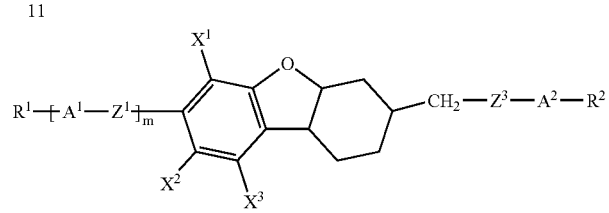

The —CH$_2$—Z$^3$— radical is analogous to Z$^2$, as defined above.

Particular preference is also given to functionalisations via the intermediate 14, which is accessible in diastereoisomerically pure form in three steps from 11 (cf. Scheme 5).

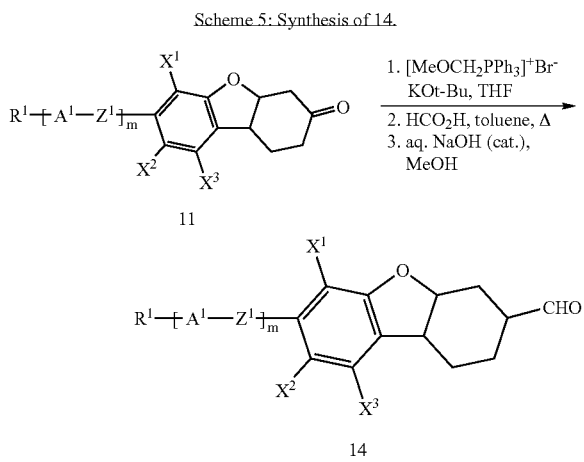

The chain lengthening starting from 14 can then in turn be initiated via the addition of a Grignard compound or by olefin formation using a Wittig reagent (cf. Scheme 6).

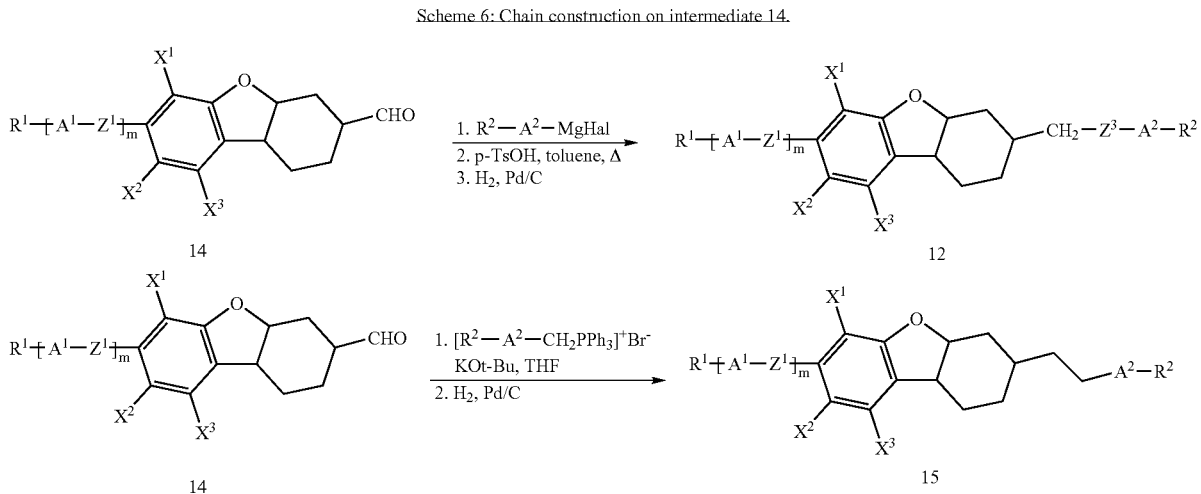

The reaction schemes depicted should only be regarded as illustrative. The person skilled in the art will be able to carry out corresponding variations of the syntheses presented and also follow other suitable synthetic routes in order to obtain compounds of the formula I. Thus, for example, the compound of the formula 7 can have a different acetal protecting group of the formula >C(O-alkyl)$_2$ or >C(cyclo-OCH$_2$CH$_2$CH$_2$O).

A common aspect of the processes for the preparation of compounds of the formula I is therefore that they include a process step in which a fluorobenzene compound is condensed in the ortho position with a cyclohexanone compound. Specifically, this is a fluorobenzene compound of the formula 3 (Schemes 1 and 2) or a cyclohexanone compound of the formula 4 or 7 in accordance with their definition generalised as above. For the process, precursors of I may likewise be the subject of the process steps described and are only derivatised on the variable substituents of the rings at a later time. The process is furthermore distinguished by the fact that it includes a process step in which a 1-(2-halophenyl)cyclohexene compound is hydroborated on the double bond of the cyclohexene. These compounds are preferably compounds of the formula 5 or 8, where the acetal group in 8 can be varied as for formula 7. The process furthermore includes a process step in which the 2-(2-halophenyl)cyclohexanol compound formed is cyclised to give a tetrahydrodibenzofuran derivative.

The cyclisation is carried out under the action of a base, preferably by means of a strong base, such as, for example, sodium hydride or potassium hydride. The reaction is carried out at between 20 and 140° C., depending on the solvent and reaction rate.

Further details on the process are revealed in the examples, the parameters of which are representative of the process according to the invention. The person skilled in the art will be able to generalise individual reaction conditions or adapt them to the individual case.

The starting materials are preferably 2-fluorobenzene derivatives, particularly preferably 2,3-difluoro derivatives. The direct process product is optionally further derivatised to give the desired liquid-crystalline or mesogenic compounds.

As already mentioned, the compounds of the general formula I can be used in liquid-crystalline media.

The present invention therefore also relates to a liquid-crystalline medium comprising at least two liquid-crystalline compounds, comprising at least one compound of the general formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexane-carboxylic acid, cyclohexylphenyl esters of benzoic acid, of cyclohexanecarboxylic acid or of cyclohexylcyclohexanecarboxylic acid, phenylcyclo-hexanes, cyclohexylbiphenyls, phenylcyclohexylcyclohexanes, cyclohexyl-cyclohexanes, cyclohexylcyclohexylcyclohexenes, 1,4-biscyclohexyl-benzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

R'-L-E-R" (II)

R'-L-COO-E-R" (III)

R'-L-COO-E-R" (IV)

R'-L-CH$_2$CH$_2$-E-R" (V)

R'-L-CF$_2$O-E-R" (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group consisting of Cyc and Phe and simultaneously one or more components selected from the compounds of the formulae (II), (III), (IV), (V) and (VI) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group consisting of -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another smaller sub-group of the compounds of the formulae (II), (III), (IV), (V) and (VI), which is known as group B, E denotes

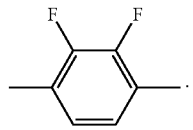

In the compounds of group B, which are referred to by the sub-formulae (IIb), (IIIb), (IVb), (Vb) and (VIb), R' and R" are as defined for the compounds of the sub-formulae (IIa) to (VIa) and are preferably alkyl, alkenyl, alkoxy or alkoxyalkyl (oxaalkyl).

In a further smaller sub-group of the compounds of the formulae (II), (III), (IV), (V) and (VI), R" denotes —CN. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' is as defined for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The proportions by weight of the compounds from these groups in the media according to the invention are:

group A:

from 0 to 90%, preferably from 20 to 90%, in particular from 30 to 90%.

group B:

from 0 to 80%, preferably from 10 to 80%, in particular from 10 to 70%.

group C:

from 0 to 80%, preferably from 5 to 80%, in particular from 5 to 50%.

The media according to the invention preferably comprise from 1 to 40%, particularly preferably from 5 to 30%, of the compounds of the formula I according to the invention. Preference is furthermore given to media comprising more than 40%, in particular from 45 to 90%, of compounds of the formula I according to the invention. The media preferably comprise one, two, three, four or five compounds of the formula I according to the invention.

Examples of the compounds of the formulae (II), (III), (IV), (V) and (VI) are the compounds shown below:

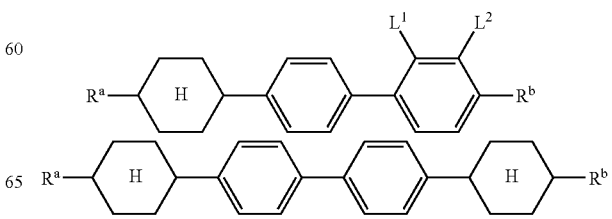

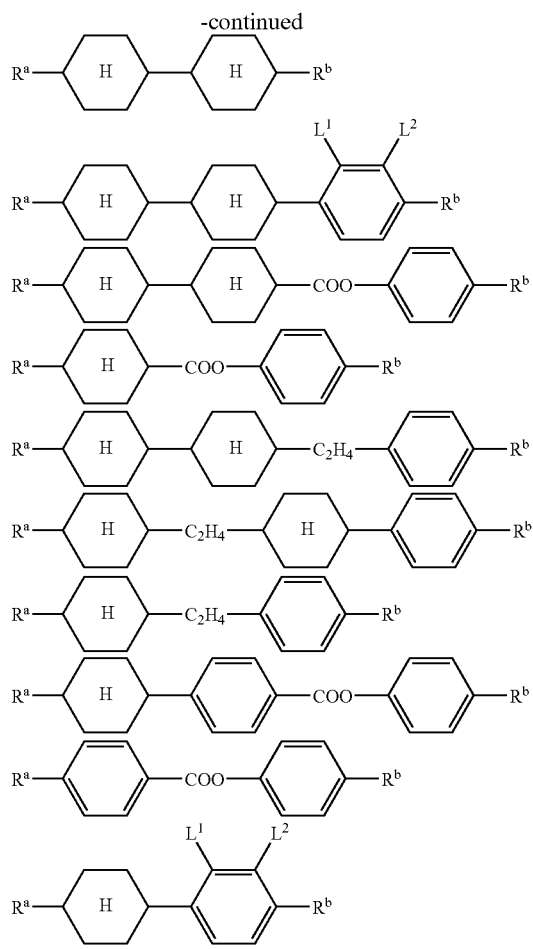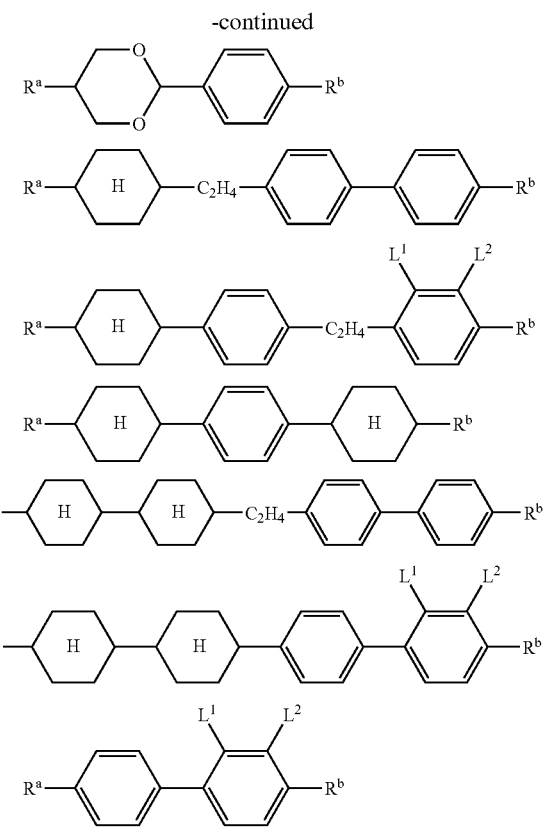
where $R^a$ and $R^b$ independently of one another, denote $-C_pH_{2p+1}$ or $-OC_pH_{2p+1}$, and p=1, 2, 3, 4, 5, 6, 7 or 8, and $L^1$ and $L^2$, independently of one another, denote —H or —F,
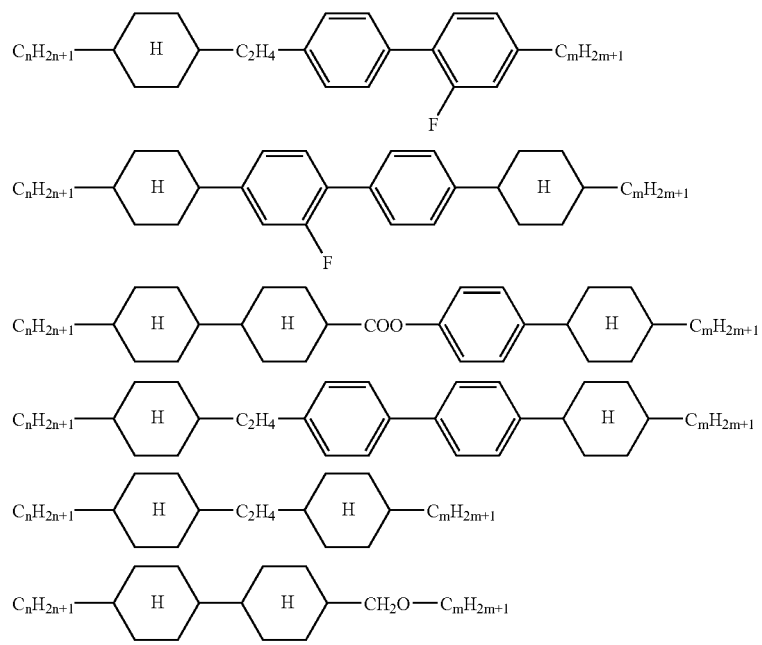

-continued

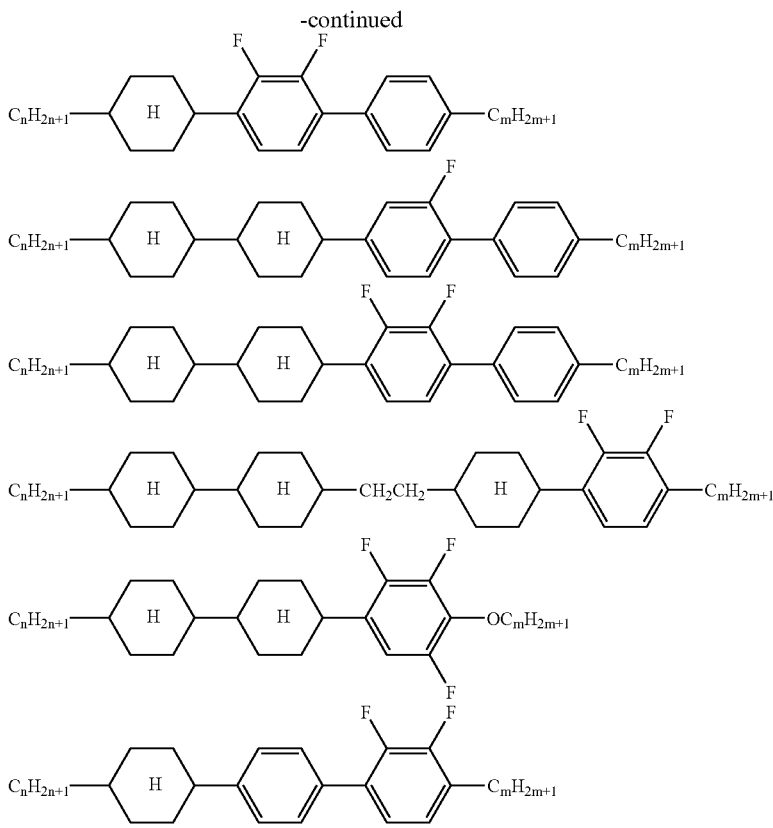

where m and n, independently of one another, denote 1, 2, 3, 4, 5, 6, 7 or 8.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be used for the production of coloured guest-host systems or substances can be added in order to modify the dielectric anisotropy, the viscosity and/or the alignment of the nematic phases.

Owing to their negative $\Delta\epsilon$, the compounds of the formula I are particularly suitable for use in VA-TFT displays.

The present invention therefore also relates to electro-optical liquid-crystal display elements containing a liquid-crystalline medium according to the invention.

The invention is explained in greater detail below with reference to working examples, but without intending to be restricted thereby.

Besides the usual and well-known abbreviations, the following abbreviations are used:

C: crystalline phase; N: nematic phase; Sm: smectic phase; I: isotropic phase. The numbers between these symbols show the transition temperatures of the substance concerned.

Temperature data are in ° C., unless indicated otherwise.

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

Above and below, $\Delta n$ denotes the optical anisotropy (589 nm, 20° C.) and $\Delta\epsilon$ denotes the dielectric anisotropy (1 kHz, 20° C.). The dielectric anisotropy $\Delta\epsilon$ is determined at 20° C. and 1 kHz. The optical anisotropy $\Delta n$ is determined at 20° C. and a wavelength of 589.3 nm.

The $\Delta\epsilon$ and $\Delta n$ values, the clearing point (cl.p.) and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for $\Delta\epsilon$) or ZLI-4792 (for $\Delta n$, cl.p., $\gamma_1$) (mixtures, Merck KGaA, Darmstadt).

The abbreviations have the following meanings:

| | |
|---|---|
| MTBE | methyl t-butyl ether |
| THF | tetrahydrofuran |
| DMF | dimethylformamide |
| i. vac. | in vacuo (about $10^{-2}$ bar) |
| sat. | saturated |
| n-BuLi | n-butyllithium, solution in hexane |

EXAMPLES

The starting substances can be obtained in accordance with generally accessible literature procedures or are commercially available. The reactions described are known from the literature.

1. (±)-(3R*, 4aR*, 9bS*)-7-ethoxy-6-fluoro-3-propyl-1,2,3,4,4a,9b-hexahydrodibenzofuran

1.1 8-(4-Ethoxy-2,3-difluorophenyl)-1,4-dioxaspiro[4.5]decan-7-ol

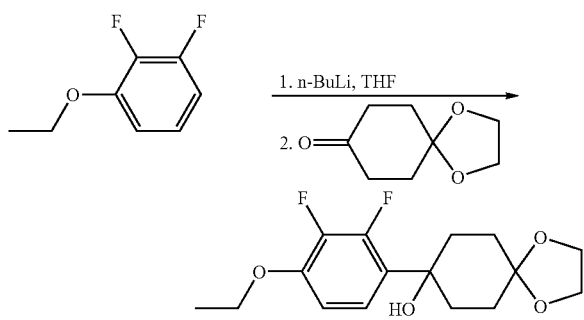

270.2 g (1.70 mol) of 2,3-difluoroethoxybenzene are initially introduced in 1200 ml of THF, and 1100 ml (1.75 mol) of n-BuLi (15% soln. in hexane) are added at −70° C. After 1 h at this temperature, a solution of 270.2 g (1.70 mol) of 1,4-cyclohexanedione monoethylene ketal in 800 ml of THF is metered in, and the batch is stirred for 1 h. The reaction mixture is warmed to 0° C. and hydrolysed using 4 N HCl. The solution is extracted with MTBE, and the combined organic phases are washed with sat. sodium chloride solution and dried using sodium sulfate. The crude product remaining after removal of the solvents under reduced pressure (609.8 g of red-brown oil) is used directly for the next reaction.

1.2 8-(4-Ethoxy-2,3-difluorophenyl)-1,4-dioxaspiro[4.5]dec-7-ene

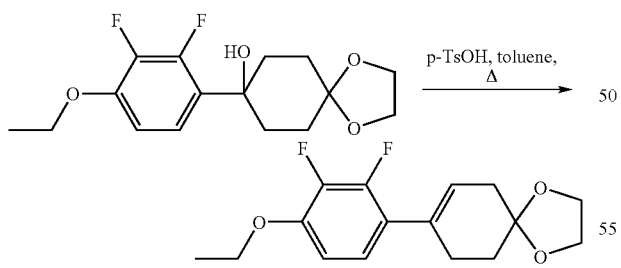

609 g (about 1.94 mol) of crude 8-(4-ethoxy-2,3-difluorophenyl)-1,4-dioxaspiro[4.5]decan-7-ol in 2000 ml of toluene are heated on a water separator for 2 h together with 220 ml (3.93 mol) of ethylene glycol with addition of 36.1 g (0.19 mol) of p-toluenesulfonic acid monohydrate. After cooling, the batch is washed successively with water, sat. sodium hydrogencarbonate solution and sat. sodium chloride solution. The solution is dried using sodium sulfate and concentrated to dryness. The crude product (507 g of orange oil) is crystallised from ethanol at −20° C., giving 8-(4-ethoxy-2,3-difluorophenyl)-1,4-dioxaspiro[4.5]dec-7-ene as yellow solid.

1.3 8-(4-Ethoxy-2,3-difluorophenyl)-1,4-dioxaspiro[4.5]decan-7-ol

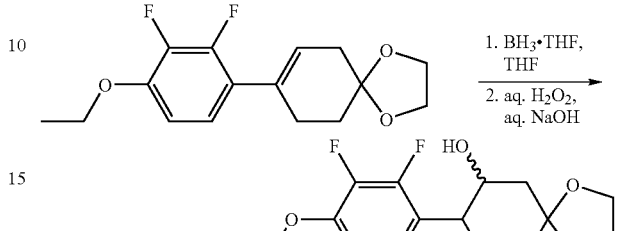

1400 ml (1.40 mol) of borane/THF complex (1 M solution) are added at −7° C. to a solution of 320.0 g (1.08 mol) of 8-(4-ethoxy-2,3-difluorophenyl)-1,4-dioxaspiro[4.5]dec-7-ene in 3000 ml of THF, and the reaction mixture is stirred at room temperature for 3 h. 262 ml (4.50 mol) of ethanol, 650 ml (2.6 mol) of aqueous sodium hydroxide solution (4 M) and 360 ml (4.11 mol) of aqueous hydrogen peroxide soln. (35%) are added successively to the batch, during which the internal temperature does not exceed 47° C. (ice bath). When the addition is complete, the mixture is refluxed for 2 h, and the solution is cooled, added to water and stirred vigorously. The organic phase is separated off, and the aqueous phase is extracted with MTBE. The combined organic phases are washed with sat. sodium chloride solution and dried using sodium sulfate. The solution is concentrated to dryness, and the crude product (336 g of yellow oil) is purified by column chromatography (SiO$_2$, dichloromethane: MTBE=8:2), giving 8-(4-ethoxy-2,3-difluorophenyl)-1,4-dioxaspiro[4.5]decan-7-ol as pale-yellow oil.

1.4 (±)-(4aR*, 9bS*)-7-Ethoxy-6-fluoro-1,4,4a,9b-tetrahydro-2H-spiro-[dibenzo[b,d]furan-3,2'-1,3-dioxolane]

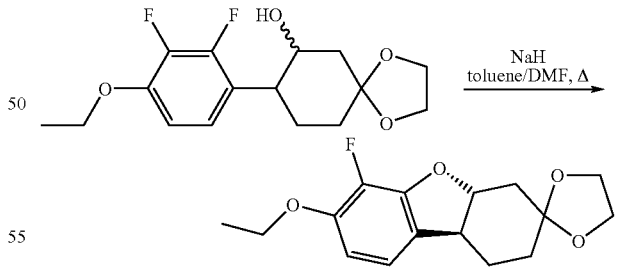

50.0 g (1.25 mol) of sodium hydride (60% suspension in mineral oil) are washed repeatedly with n-pentane and suspended in 3000 ml of toluene. The suspension is heated to 90° C., and a solution of 145.0 g (0.46 mol) of 8-(4-ethoxy-2,3-difluorophenyl)-1,4-dioxaspiro[4.5]decan-7-ol in 700 ml of DMF is slowly metered in. The batch is stirred at 90° C. for 30 h, cooled and hydrolysed using water. The mixture is neutralised by addition of 2 N hydrochloric acid, and the organic phase is separated off. The aqueous phase is extracted with toluene, and the combined organic phases are washed with sat. sodium chloride solution. The solution is dried using sodium sulfate and concentrated to dryness under reduced pressure. The crude product obtained is recrystallised from ethanol at 5° C., giving (±)-(4aR*, 9bS*)-7-ethoxy-6-fluoro-1,4,4a,9b-tetrahydro-2H-spiro-[dibenzo[b,d]-furan-3,2'-1,3-dioxolane] as colourless solid.

1.5 (±)-(4aR*, 9bS*)-7-Ethoxy-6-fluoro-1,4,4a,9b-tetrahydro-2H-dibenzofuran-3-one

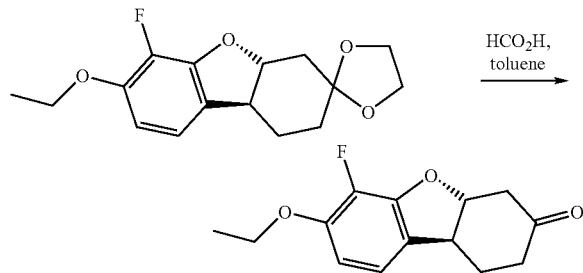

135.0 g (459 mmol) of (±)-(4aR*, 9bS*)-7-ethoxy-6-fluoro-1,4,4a,9b-tetrahydro-2H-spiro[dibenzo[b,d]furan-3,2'-1,3-dioxolane] are dissolved in 1800 ml of toluene and stirred vigorously together with 550 ml (14.6 mol) of formic acid with addition of 10.0 ml (0.56 mol) of water. After 18 h, the organic phase is separated off, and the formic acid is extracted with toluene. The combined organic phases are washed successively with water, sat. sodium hydrogencarbonate solution and sat. sodium chloride solution and dried using sodium sulfate. The crude product remaining after removal of the solvent is purified by column chromatography (SiO₂, toluene: ethyl acetate=4:1), giving (±)-(4aR*, 9bS*)-7-ethoxy-6-fluoro-1,4,4a,9b-tetrahydro-2H-dibenzofuran-3-one as colourless solid.

1.6 (±)-(4aR*, 9bS*)-7-Ethoxy-6-fluoro-3-[1-methoxymethylidene]-1,2,3,4,4a,9b-hexahydrodibenzofuran

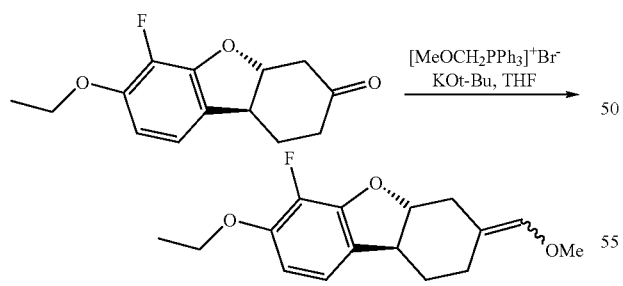

58.3 g (170 mmol) of methoxymethyltriphenylphosphonium chloride are initially introduced in 500 ml of THF, and a solution of 19.1 g (170 mmol) of potassium tert-butoxide in 200 ml of THF is added at 0° C. After 30 min at this temperature, 7-ethoxy-6-fluoro-1,4,4a,9b-tetrahydro-2H-dibenzofuran-3-one as solution in 300 ml of THF is added, and the batch is stirred at room temperature for 17 h. Water is added at 0° C., and the mixture is acidified using 2 N hydrochloric acid. The batch is extracted with MTBE, and the combined extracts are washed with sat. sodium chloride solution. The solution is dried using sodium sulfate and concentrated to dryness. Purification of the crude product by column chromatography (SiO₂, toluene) gives (±)-(4aR*, 9bS*)-7-ethoxy-6-fluoro-3-[1-methoxy-methylidene]-1,2,3,4,4a,9b-hexahydrodibenzofuran as colourless solid.

1.7 (±)-(3R*, 4aR*, 9bS*-7-Ethoxy-6-fluoro-1,2,3,4,4a,9b-hexahydrodibenzofuran-3-carbaldehyde and (±)-(3S*, 4aR*, 9bS*)-7-ethoxy-6-fluoro-1,2,3,4,4a,9b-hexahydrodibenzofuran-3-carbaldehyde

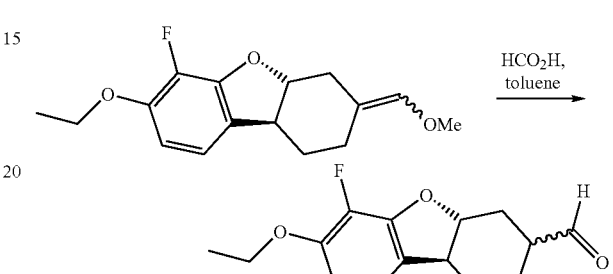

8.0 g (28.7 mmol) of (±)-(4aR*, 9bS*)-7-ethoxy-6-fluoro-3-[1-methoxy-methylidene]-1,2,3,4,4a,9b-hexahydrodibenzofuran are dissolved in 200 ml of toluene and stirred vigorously at room temperature for 18 h together with 30 ml (0.80 mol) of formic acid and 0.5 ml (27.8 mmol) of water. The organic phase is separated off and washed successively with water, sat. sodium hydrogencarbonate solution and sat. sodium chloride solution. The solution is dried using sodium sulfate and concentrated to dryness. Purification by column chromatography (SiO₂, toluene:ethyl acetate=99:1) gives a mixture (64:36) of (±)-(3R*, 4aR*, 9bS*)-7-ethoxy-6-fluoro-1,2,3,4,4a,9b-hexahydrodibenzofuran-3-carbaldehyde and (±)-(3S*, 4aR*, 9bS*)-7-ethoxy-6-fluoro-1,2,3,4,4a,9b-hexahydrodibenzofuran-3-carbaldehyde.

1.8 Isomerisation to (±)-(3R*, 4aR*, 9bS*)-7-ethoxy-6-fluoro-1,2,3,4,4a,9b-hexahydrodibenzofuran-3-carbaldehyde

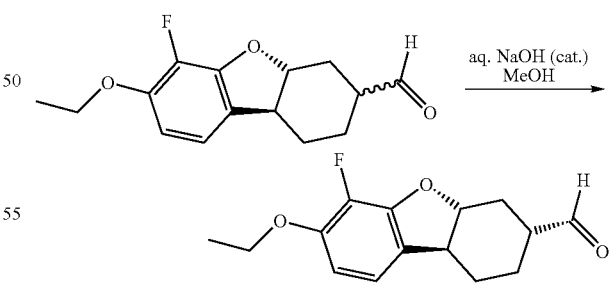

6.70 g (25.2 mmol) of a mixture (64:36) of (±)-(3R*, 4aR*, 9bS*)-7-ethoxy-6-fluoro-1,2,3,4,4a,9b-hexahydrodibenzofuran-3-carbaldehyde and (±)-(3S*, 4aR*, 9bS*)-7-ethoxy-6-fluoro-1,2,3,4,4a,9b-hexahydrodibenzofuran-3-carbaldehyde are dissolved in 170 ml of methanol/THF mixture (5:2), and 0.37 ml (2.50 mmol) of aqueous sodium hydroxide solution (20%) is added dropwise. After 1 h at room temperature, the solution is added to water and acidified using 2 N hydrochloric acid. The batch is extracted with MTBE, and the combined organic phases are washed with sat. sodium chloride solution. The solution is dried using sodium sulfate and concentrated to dryness. The crude product from the reaction is used directly for the following steps.

1.9 (±)-(3R*, 4aR*, 9bS*)-7-Ethoxy-6-fluoro-3-propenyl-1,2,3,4,4a,9b-hexahydrodibenzofuran

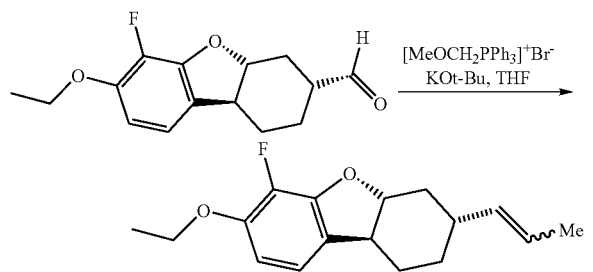

10.0 g (27.0 mmol) of ethyltriphenylphosphonium bromide are initially introduced in 100 ml of THF, and 2.98 g (26.0 mmol) of potassium tert-butoxide in 40 ml of THF are added at −5° C. After 1 h at this temperature, 6.50 g (24.6 mmol) of (±)-(3R*, 4aR*, 9bS*)-7-ethoxy-6-fluoro-1,2,3,4,4a,9b-hexahydrodibenzofuran-3-carbaldehyde as a solution in 60 ml of THF are added dropwise, and the batch is stirred at room temperature for 2 h. The reaction solution is hydrolysed using water and acidified using 2 N HCl. The mixture is extracted with MTBE, and the combined organic phases are dried using sodium sulfate. The crude product remaining after removal of the solvents is filtered adsorptively (SiO₂, toluene), and the filtrate is concentrated to dryness. Recrystallisation of the residue from methanol gives (±)-(3R*, 4aR*, 9bS*)-7-ethoxy-6-fluoro-3-propenyl)-1,2,3,4,4a,9b-hexahydrodibenzofuran as E/Z isomer mixture.

1.10 (±)-(3R*, 4aR*, 9bS*)-7-Ethoxy-6-fluoro-3-propyl-1,2,3,4,4a,9b-hexahydrodibenzofuran

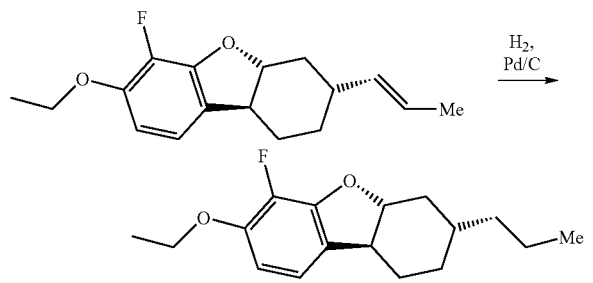

3.50 g (12.7 mmol) of (±)-(3R*, 4aR*, 9bS*)-7-ethoxy-6-fluoro-3-propenyl-1,2,3,4,4a,9b-hexahydrodibenzofuran in THF are hydrogenated for 23 h in a hydrogen atmosphere with addition of 1.8 g of Pd/C. After completion of the uptake of hydrogen, the reaction solution is filtered and concentrated to dryness. The residue is filtered adsorptively (SiO₂, toluene: n-heptane=1:1), and the beige solid obtained is recrystallised repeatedly from isopropanol at room temperature, giving (±)- (3R*, 4aR*, 9bS*)-7-ethoxy-6-fluoro-3-propyl-1,2,3,4,4a,9b-hexahydrodibenzofuran as colourless solid (melting point 128° C.).

C 128 I
Δε=−6.0
Δn=0.102
γ₁=127 mPa·s

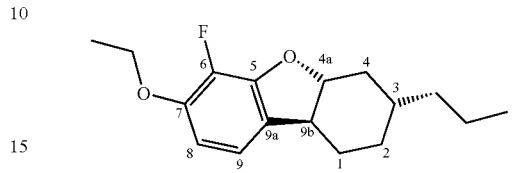

$^1$H-NMR (500 MHz, CHCl₃): δ=6.73 (d, 1H, J=8.0 Hz, 9-H), 6.45 (dd, 1H, J=8.0 Hz, J=6.8 Hz, 8-H), 4.06 (dq, 2H, J=7.0 Hz, J=1.5 Hz, OCH₂CH₃), 3.95 (ddd, 1H, J=12.6 Hz, J=11.5 Hz, J=3.5 Hz, 4a-H), 2.74 (ddd, 1H, J=12.6 Hz, J=12.6 Hz, J=2.8 Hz, 9b-H), 2.41-2.37 (m, 1H, 4-H), 2.30-2.26 (m, 1H, 1-H), 1.89 (dd, 1H, J=13.8 Hz, J=2.7 Hz, 2-H), 1.58-1.45 (m, 2H, 1-H, 3-H), 1.42 (t, 3H, J=7.0 Hz, OCH₂CH₃), 1.39-1.29 (m, 5H, 4-H, CH₂CH₂CH₃), 1.06 (ddd, 1H, J=13.8 Hz, J=12.9 Hz, J=4.0 Hz, 2-H), 0.91 (t, 3H, J=6.9 Hz, CH₂CH₂CH₃).

$^{19}$F-NMR (235 MHz, CHCl₃): δ=−157.9 (d, 1 F, $^4$J=6.8 Hz).

MS: m/e (%)=278 (100, M+), 235 ([M-Pr]⁺, 49).

2. (±)-(3R*,4aR*,9bS*)-7-Ethoxy-3-(4-ethoxy-2,3-difluorophenyl)-6-fluoro-1,2,3,4,4a,9b-hexahydrodibenzofuran

2.1 (±)-(4aR*, 9bS*)-7-Ethoxy-3-(4-ethoxy-2,3-difluorophenyl)-6-fluoro-1,2,3,4,4a,9b-hexahydrodibenzofuran-3-ol

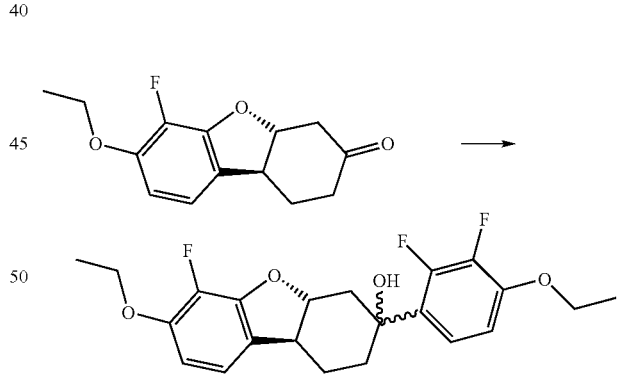

7.94 g (50.2 mmol) of 2,3-difluoroethoxybenzene are initially introduced in 50 ml of THF, and 30.5 ml (48.8 mol) of n-BuLi (15% soln. in hexane) are added at −70° C. After 1 h at this temperature, a solution of 10.0 g (40.0 mmol) of (±)-(4aR*, 9bS*)-7-ethoxy-6-fluoro-1,4,4a,9b-tetrahydro-2H-dibenzofuran-3-one in 150 ml of THF is metered in. After 4 h, the batch is hydrolysed using water and acidified using 4 N HCl. The solution is extracted with MTBE, and the combined organic phases are washed with sat. sodium chloride solution and dried using sodium sulfate. The crude product remaining after removal of the solvents under reduced pressure is digested in 500 ml of ethanol at 40° C. Filtration gives (±)-(4aR*, 9bS*)-7-ethoxy-3-(4-ethoxy-2,3-difluorophenyl)-6-fluoro-1,2,3,4,4a,9b-hexahydrodibenzofuran-3-ol as colourless solid.

2.2 (±)-(4aR*, 9bS*)-7-Ethoxy-3-(4-ethoxy-2,3-difluorophenyl)-6-fluoro-1,2,4a,9b-tetrahydrodibenzofuran and

(±)-(4aR*, 9bS*)-7-ethoxy-3-(4-ethoxy-2,3-difluorophenyl)-6-fluoro-1,4,4a,9b-tetrahydrodibenzofuran

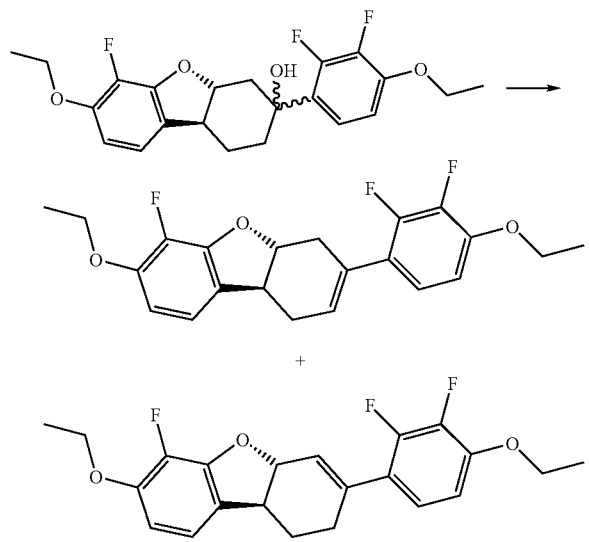

8.5 g (20.8 mmol) of (±)-(4aR*, 9bS*)-7-ethoxy-3-(4-ethoxy-2,3-difluorophenyl)-6-fluoro-1,2,3,4,4a,9b-hexahydrodibenzofuran-3-ol in 200 ml of toluene are heated on a water separator for 30 min together with 396 mg (2.08 mmol) of p-toluenesulfonic acid monohydrate. After cooling, the batch is filtered adsorptively (SiO$_2$, ethyl acetate:n-heptane=4:1), and the filtrate is concentrated to dryness. The product mixture obtained in this way can be used directly for the following reaction.

2.3 (±)-(3R*, 4aR*, 9bS*)-7-Ethoxy-3-(4-ethoxy-2,3-difluorophenyl)-6-fluoro-1,2,3,4,4a,9b-hexahydrodibenzofuran 7.4 g (about 19.0 mmol) of a mixture of (±)-(4aR*, 9bS*)-7-ethoxy-3-(4-ethoxy-2,3-difluorophenyl)-6-fluoro-1,2,4a,9b-tetrahydrodibenzofuran and (±)-(4aR*, 9bS*)-7-ethoxy-3-(4-ethoxy-2,3-difluorophenyl)-6-fluoro-1,4,4a,9b-tetrahydrodibenzofuran in 160 ml of ethyl acetate/ethanol mixture (3:1) are hydrogenated at 80° C. in the presence of 3.70 g of Raney nickel and 1.50 g of ion exchanger (weakly H-acidic) under hydrogen pressure (4.4 bar). After 18 h, the catalyst is filtered off, and the filtrate is concentrated to dryness. The crude product is recrystallised successively from isopropanol, n-heptane and ethanol, giving (±)-(3R*, 4aR*, 9bS*)-7-ethoxy-3-(4-ethoxy-2,3-difluorophenyl)-6-fluoro-1,2,3,4,4a,9b-hexahydrodibenzofuran as colourless solid (melting point 126° C.).

C 126 N (99) I

Δε=−12.0

Δn=0.138

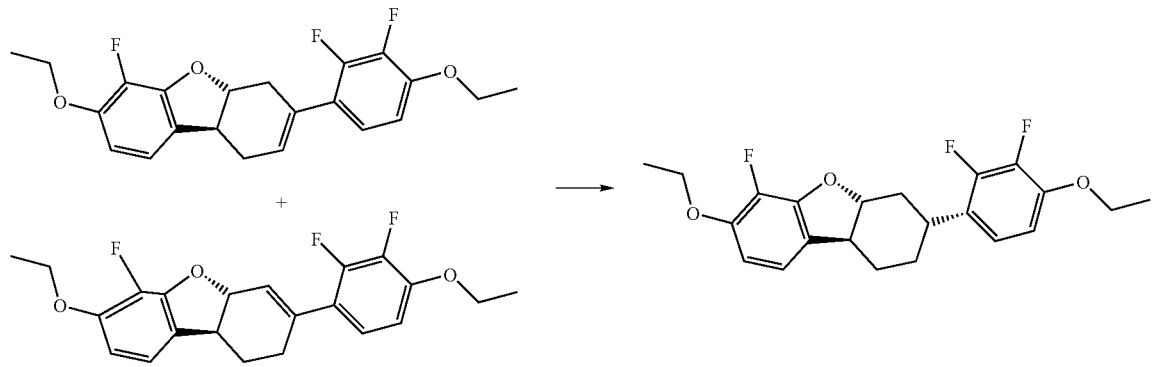

$^1$H-NMR (250 MHz, CHCl$_3$): δ=6.94-6.87 (m, 1H, H$_{arom.}$), 6.78 (dm, 1H, J=8.0 Hz, H$_{arom.}$), 6.75-6.67 (m, 1H, H$_{arom.}$), 6.49 (dd, 1H, J=8.0 Hz, J=7.0 Hz, H$_{arom.}$), 4.17-4.04 (m, 5H, OCH$_2$CH$_3$, 4a-H, OCH$_2$CH$_3$), 3.11-2.86 (m, 2H, 9b-H, 3-H), 2.54-2.37 (m, 2H, H$_{aliph.}$), 2.20-1.96 (m, 2H, H$_{aliph.}$), 1.63-1.55 (m, 2H, H$_{aliph.}$), 1.44 (t, 3H, J=7.0 Hz, OCH$_2$CH$_3$), 1.43 (t, 3H, J=7.0 Hz, OCH$_2$CH$_3$).

$^{19}$F-NMR (235 MHz, CHCl$_3$): δ=−142.9 (ddd, 1F, J=13.5 Hz, J=7.4 Hz, J=1.2 Hz), −159.2 (ddd, 1F, J=13.5 Hz, J=7.4 Hz, J=1.2 Hz), −159.8 (d, 1 F, J=6.8 Hz).

MS (EI): m/e (%)=392 (39, M$^+$), 234 (100).

3. (±)-(3R*,4aR*,9bS*)-7-Ethoxy-6-fluoro-3-vinyl-1,2,3,4,4a,9b-hexahydrodibenzofura

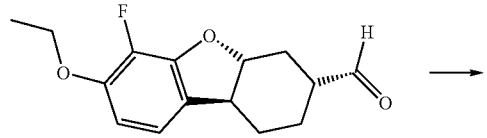

5.0 g (14.0 mmol) of methyltriphenylphosphonium bromide are initially introduced in 50 ml of THF, and 1.60 g (14.3 mmol) of potassium tert-butoxide in 20 ml of THF are added at −5° C. After 1 h at this temperature, 3.40 g (12.9 mmol) of (±)-(3R*, 4aR*, 9bS*)-7-ethoxy-6-fluoro-1,2,3,4,4a,9b-hexahydrodibenzofuran-3-carbaldehyde as a solution in 30 ml of THF are added dropwise, and the batch is stirred at room temperature for 16 h. The reaction solution is hydrolysed using water and acidified using 2 N HCl. The mixture is extracted with MTBE, and the combined organic phases are washed with sat. sodium chloride solution and dried using sodium sulfate. The crude product remaining after removal of the solvents is purified by column chromatography (SiO$_2$, toluene). Further purification was carried out by repeated recrystallisation from isopropanol, giving (±)-(3R*, 4aR*, 9bS*)-7-ethoxy-6-fluoro-3-vinyl-1,2,3,4,4a,9b-hexahydrodibenzofuran as colourless solid (melting point 141° C.).

C 141 I

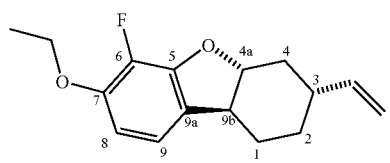

$^1$H-NMR (250 MHz, CHCl$_3$): δ=6.75 (dm, 1H, J=8.0 Hz, 9-H), 6.46 (dd, 1H, J=8.0 Hz, J=7.0 Hz, 8-H), 5.92-5.78 (m, 1H, H$_{vinyl}$) 5.11-4.97 (m, 2H, H$_{vinyl}$), 4.07 (d, 2H, J=7.0 Hz, OCH$_2$CH$_3$), 4.05-3.95 (m, 1H, 4a-H), 2.83-2.72 (m, 1H, 9b-H), 2.47-2.18 (m, 3H, H$_{aliph.}$), 1.97-1.87 (m, 1H, H$_{aliph.}$), 1.80-1.67 (m, 1H, H$_{aliph.}$), 1.53-1.18 (m, 5H, J=7.0 Hz, H$_{aliph.}$, OCH$_2$CH$_3$).

$^{19}$F-NMR (235 MHz, CHCl$_3$): δ=−157.6 (d, 1 F, $^4$J=6.8 Hz).

MS (EI): m/e (%)=262 (81, M$^+$), 206 (100, [M-Et-Vn]$^+$).

4. (±)-(3R*, 4aR*, 9bS*)-7-Ethoxy-6-fluoro-3-((E)-propenyl)-1,2,3,4,4a,9b-hexahydrodibenzofuran

4.1 Isomerisation to (±)-(3R*, 4aR*, 9bS*)-7-ethoxy-6-fluoro-3-((E)-propenyl)-1,2,3,4,4a,9b-hexahydrodibenzofuran

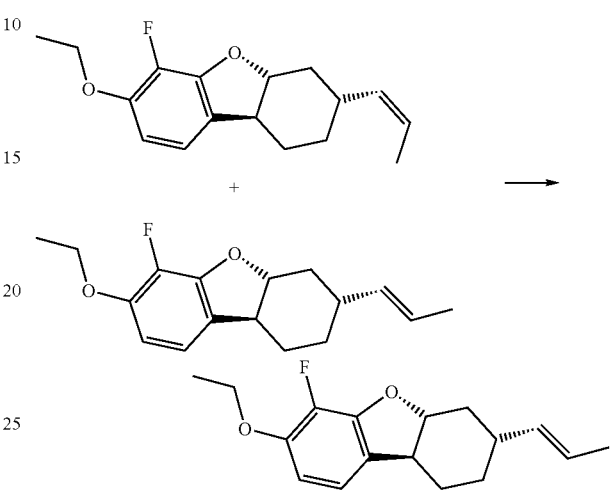

6.0 g (about 21.7 mmol) of (E/Z) isomer mixture of (±)-(3R*, 4aR*, 9bS*)-7-ethoxy-6-fluoro-3-propenyl-1,2,3,4,4a,9b-hexahydrodibenzofuran (see 1.9) are refluxed in 60 ml of toluene together with 1.15 g (7.0 mmol) of benzene-sulfinic acid sodium salt and 21.4 ml of 1 N hydrochloric acid. After 1 h, the mixture is added to water, and the organic phase is separated off. The aqueous phase is extracted with MTBE, and the combined organic phases are washed with sat. sodium chloride solution. The solution is dried using sodium sulfate and concentrated to dryness. Repeated recrystallisation from isopropanol gives (±)-(3R*, 4aR*, 9bS*)-7-ethoxy-6-fluoro-3-((E)-propenyl)-1,2,3,4,4a,9b-hexahydrodibenzofuran as colourless solid (melting point 145° C.).

C 145 I

Δε=−6.0

Δn=0.110

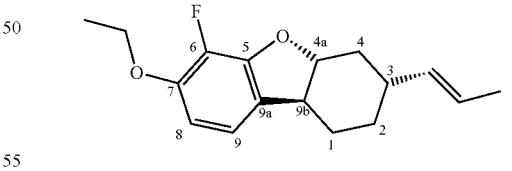

$^1$H-NMR (250 MHz, CHCl$_3$): δ=6.74 (dm, 1H, J=8.0 Hz, 9-H), 6.46 (dd, 1H, J=8.0 Hz, J=7.0 Hz, 8-H), 5.54-5.38 (m, 2H, H$_{vinyl}$), 4.07 (q, 2H, J=7.0 Hz, OCH$_2$CH$_3$), 4.04-3.92 (m, 1H, 4a-H), 2.81-2.70 (m, 1H, 9b-H), 2.42-2.11 (m, 3H, H$_{aliph.}$), 1.91-1.82 (m, 1H, H$_{aliph.}$), 1.76-1.62 (m, 4H, J=4.8 Hz, H$_{aliph.}$, CH=CHCH$_3$), 1.52-1.14 (m, 5H, J=7.0 Hz, H$_{aliph.}$, OCH$_2$CH$_3$).

$^{19}$F-NMR (235 MHz, CHCl$_3$): δ=−159.1 (d, 1F, $^4$J=6.8 Hz).

MS (EI): m/e (%)=276 (72, M$^+$), 206 (100, [M-Et-C$_3$H$_5$]$^+$).

5. (±)-(3R*, 4aR*, 9bS*)-7-Ethoxy-6-fluoro-3-pentyl-1,2,3,4,4a,9b-hexahydrodibenzofuran

5.1 (±)-(3R*,4aR*, 9bS-7-Ethoxy-6-fluoro-3-((E)-pent-1-enyl)-1,2,3,4,4a,9b-hexahydrodibenzofuran and (±)-(3R*,4aR*, 9bS-7-ethoxy-6-fluoro-3-((Z)-pent-1-enyl)-1,2,3,4,4a,9b-hexahydrodibenzofuran

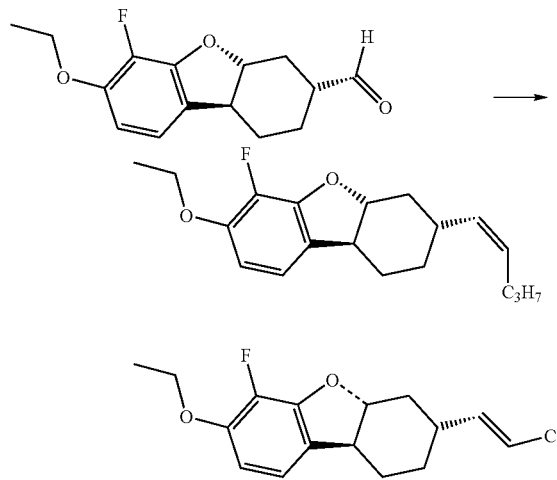

8.98 g (22.5 mmol) of butyltriphenylphosphonium bromide are initially introduced in 100 ml of THF, and 2.58 g (23.0 mmol) of potassium tert-butoxide in 40 ml of THF are added at −5° C. After 1 h at this temperature, 5.50 g (20.8 mmol) of (±)-(3R*, 4aR*, 9bS-7-ethoxy-6-fluoro-1,2,3,4,4a,9b-hexahydrodibenzofuran-3-carbaldehyde as a solution in 60 ml of THF are added dropwise, and the batch is stirred at room temperature for 2 h. The reaction solution is hydrolysed using water and acidified using 2 N HCl. The mixture is extracted with MTBE, and the combined organic phases are washed with sat. sodium chloride solution and dried using sodium sulfate. The crude product remaining after removal of the solvents is purified by column chromatography (SiO$_2$, toluene). The E/Z isomer mixture obtained in this way can be used directly for the following reaction.

5.2 (±)-(3R*, 4aR*, 9bS*)-7-Ethoxy-6-fluoro-3-pentyl-1,2,3,4,4a,9b-hexahydrodibenzofuran

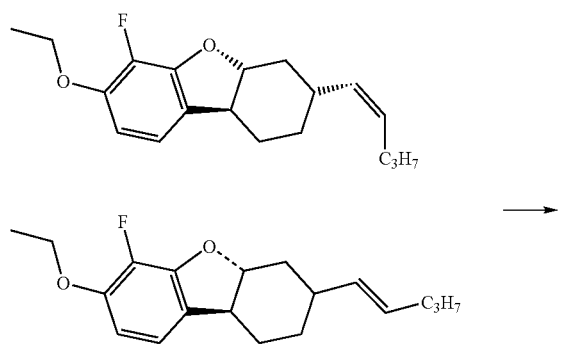

5.1 g (about 10.7 mmol) of (E/Z) isomer mixture of (±)-(3R*, 4aR*, 9bS*)-7-ethoxy-6-fluoro-3-pent-1-enyl-1,2,3,4,4a, 9b-hexahydrodibenzofuran in 50 ml of THF are hydrogenated in a hydrogen atmosphere with addition of 5.0 g of Pd/C (5% Pd). After completion of the uptake of hydrogen (37 h), the reaction solution is filtered and concentrated to dryness. The residue is filtered adsorptively (SiO$_2$, toluene), and the beige solid obtained is re-crystallised repeatedly from isopropanol at room temperature, giving (±)-(3R*, 4aR*, 9bS*)-7-ethoxy-6-fluoro-3-pentyl-1,2,3,4,4a,9b-hexahydro-dibenzofuran as colourless solid (melting point 118° C.).

C 118 I

Δε=−5.4

Δn=0.104

γ$_1$=172 mPa·s

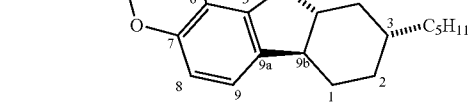

$^1$H-NMR (250 MHz, CHCl$_3$): δ=6.74 (dm, 1H, J=8.0 Hz, 9-H), 6.45 (dd, 1H, J=8.0 Hz, J=7.0 Hz, 8-H), 4.07 (q, 2H, J=7.0 Hz, OCH$_2$CH$_3$), 4.01-3.90 (m, 1H, 4a-H), 2.80-2.69 (m, 1H, 9b-H), 2.43-2.36 (m, 1H, H$_{aliph.}$), 2.29 (dm, 1H, J=12.5 Hz, H$_{aliph.}$), 1.90 (dd, 1H, J=13.1 Hz, J=2.7 Hz, H$_{aliph.}$), 1.50-1.20 (m, 14H, H$_{aliph.}$), 1.16-0.98 (m, 1H, H$_{aliph.}$), 0.90 (t, 3H, J=7.0 Hz, OCH$_2$CH$_3$).

$^{19}$F-NMR (235 MHz, CHCl$_3$): δ=−160.1 (d, 1F, $^4$J=7.1 Hz).

MS (EI): m/e (%)=306 (100, M$^+$), 235 (100, [M-C$_5$H$_{11}$]$^+$).

6. (±)-(3R*,4aR*,9bS*)-7-Butoxy-6-fluoro-3-(4-propylcyclohexyl)-1,2,3,4,4a,9b-hexahydrodibenzofuran

6.1 4-(4-Butoxy-2,3-difluorophenyl)-4'-propylbicyclohexyl-4-ol

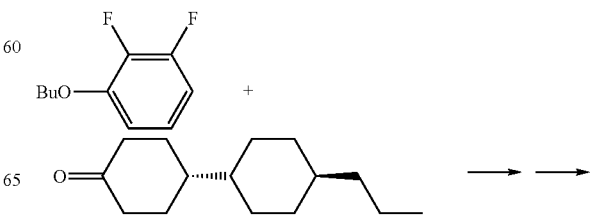

-continued

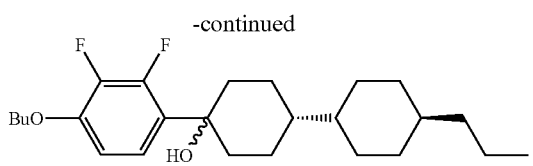

31.0 g (0.17 mol) of 1-butoxy-2,3-difluorobenzene are initially introduced in 200 ml of THF, and 100 ml (0.16 mol) of n-BuLi (15% soln. in hexane) are added at −70° C. After 2 h at this temperature, a solution of 35.6 g (0.16 mol) of 4'-propylbicyclohexyl-4-one in 200 ml of THF is metered in, and the batch is stirred for 2.5 h. The reaction mixture is hydrolysed with ice-cooling and acidified using 2 N HCl. The solution is extracted with MTBE, and the combined organic phases are washed with sat. sodium chloride solution and dried using sodium sulfate. The solution is concentrated to dryness, and the crude product (66.3 g of yellow solid) is used directly for the following reaction.

6.2 4-(4-Butoxy-2,3-difluorophenyl)-4'-propylbicyclohexyl-3-ene

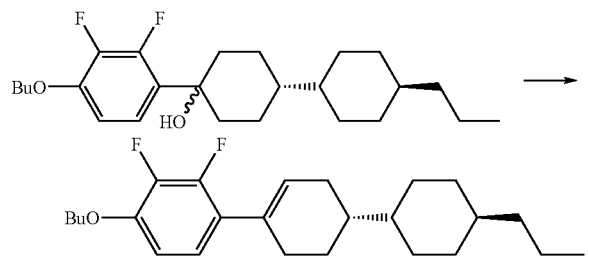

66.3 g (about 0.16 mol) of crude 4-(4-butoxy-2,3-difluorophenyl)-4'-propylbicyclohexyl-4-ol in 200 ml of toluene are heated on a water separator for 2 h together with 3.04 g (16.0 mmol) of p-toluenesulfonic acid monohydrate. After cooling, the batch is washed successively with water, sat. sodium hydrogencarbonate solution and sat. sodium chloride solution. The solution is dried using sodium sulfate and concentrated to dryness. The crude product (60.7 g of orange oil) is crystallised from ethanol, giving 4-(4-butoxy-2,3-difluorophenyl)-4'-propylbicyclohexyl-3-ene as yellow solid.

6.3 4-(4-Butoxy-2,3-difluorophenyl)-4'-propylbicyclohexyl-3-ol

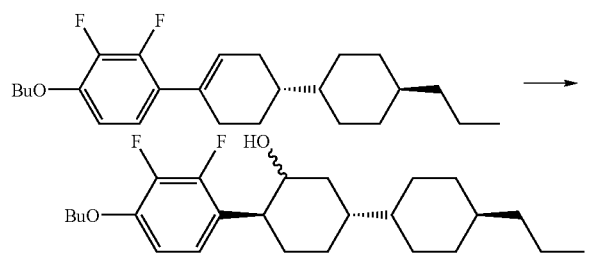

110 ml (0.11 mol) of borane/THF complex (1 M solution) are added at −5° C. to a solution of 31.4 g (80.4 mmol) of 4-(4-butoxy-2,3-difluorophenyl)-4'-propylbicyclohexyl-3-ene in 320 ml of THF, and the reaction mixture is stirred at room temperature for 3 h. 20 ml (0.35 mol) of ethanol, 50 ml (0.2 mol) of aqueous sodium hydroxide solution (4 M) and 28 ml (0.32 mol) of aqueous hydrogen peroxide soln. (35%) are added successively to the batch, during which the internal temperature does not exceed 47° C. (ice bath). When the addition is complete, the mixture is refluxed for 2 h, and the solution is cooled, added to water and stirred vigorously. The organic phase is separated off, and the aqueous phase is extracted with MTBE. The combined organic phases are washed with sat. sodium chloride solution and dried using sodium sulfate. The solution is concentrated to dryness, and the crude product (32 g) is purified by column chromatography (SiO$_2$, toluene → toluene:ethyl acetate=8:2), giving 4-(4-butoxy-2,3-difluorophenyl)-4'-propylbicyclohexyl-3-ol as colourless solid.

6.4 (±)-(3R*,4aR*,9bS*)-7-Butoxy-6-fluoro-3-(4-propylcyclohexyl)-1,2,3,4,4a,9b-hexahydrodibenzofuran

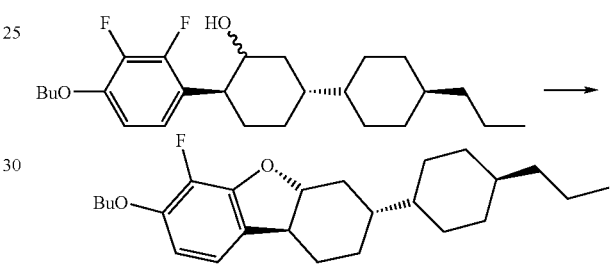

5.40 g (135 mmol) of sodium hydride (60% suspension in mineral oil) are washed repeatedly with n-pentane and suspended in 400 ml of toluene. The suspension is heated to 90° C., and a solution of 17.5 g (42.8 mmol) of 4-(4-butoxy-2,3-difluorophenyl)-4'-propylbicyclohexyl-3-ol in 100 ml of DMF is metered in slowly. The batch is stirred at 90° C. for 20 h, cooled and hydrolysed using water. The mixture is neutralised by addition of 2 N hydrochloric acid, and the organic phase is separated off. The aqueous phase is extracted with toluene, and the combined organic phases are washed with sat. sodium chloride solution. The solution is dried using sodium sulfate and concentrated to dryness under reduced pressure. The crude product obtained is recrystallised from ethanol at 5° C., giving (±)-(3R*, 4aR*, 9bS*-7-butoxy-6-fluoro-3-(4-propylcyclohexyl)-1,2,3,4,4a,9b-hexahydrodibenzofuran as colourless solid (melting point 105° C.).

C 105 Sm$_A$ 154 N 166 I

Δε=−5.6

Δn=0.114

γ$_1$=974 mPa·s

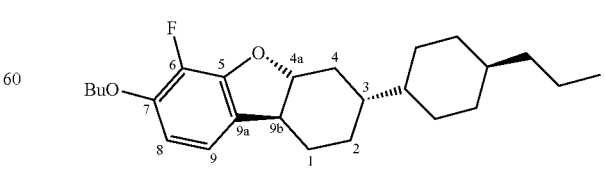

$^1$H-NMR (250 MHz, CHCl$_3$): δ=6.73 (dm, 1H, J=8.0 Hz, 9-H), 6.45 (dd, 1H, J=8.0 Hz, J=7.0 Hz, 8-H), 3.99 (t, 3H,

J=6.9 Hz, OCH$_2$CH$_2$), 3.98-3.88 (m, 1H, 4a-H), 2.77-2.66 (m, 1H, H$_{aliph.}$), 2.40-2.26 (m, 2H, H$_{aliph.}$), 1.90-1.69 (m, 9H, H$_{aliph.}$), 1.65-1.02 (m, 13H, H$_{aliph.}$), 0.96 (t, 3H, J=7.4 Hz, Me), 0.88 (t, 3H, J=7.2 Hz, Me).

$^{19}$F-NMR (235 MHz, CHCl$_3$): δ=158.2 (d, 1 F, j=6.8 Hz). MS (EI): m/e (%)=388 (100, M$^+$).

7. (±)-(3R*,4aR*,9bS*)-(±)-(3R*,4aR*,9bS*)-7-Ethoxy-6-fluoro-3-(4-vinyl-cyclohexyl)-1,2,3,4,4a,9b-hexahydrodibenzofuran

7.1 4-(1,4-Dioxaspiro[4.5]dec-8-yl)-1-(4-ethoxy-2,3-difluorophenyl)cyclo-hexanol

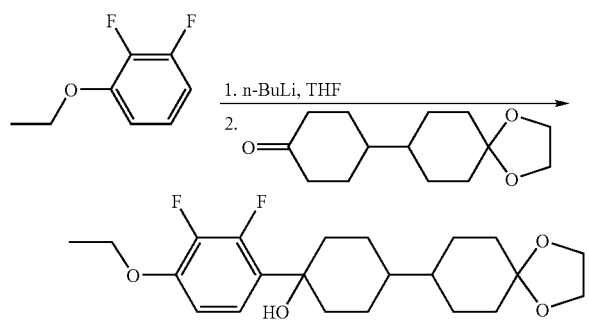

99.5 g (0.63 mol) of 2,3-difluoroethoxybenzene are initially introduced in 800 ml of THF, and 384 ml (0.63 mol) of n-BuLi (15% soln. in hexane) are added at −70° C. After 30 min at this temperature, a solution of 150 g (0.63 mol) of 4-(1,4-dioxaspiro[4.5]dec-8-yl)cyclohexanone in 700 ml of THF is metered in, and the batch is stirred for 30 min. The reaction mixture is warmed to 0° C. and hydrolysed using 2 N HCl. The solution is extracted with MTBE, and the combined organic phases are washed with sat. sodium chloride solution and dried using sodium sulfate. The crude product remaining after removal of the solvents under reduced pressure is used directly for the next reaction.

7.2 8-[4-(4-Ethoxy-2,3-difluorophenyl)cyclohex-3-enyl]-1,4-dioxaspiro[4.5]decane

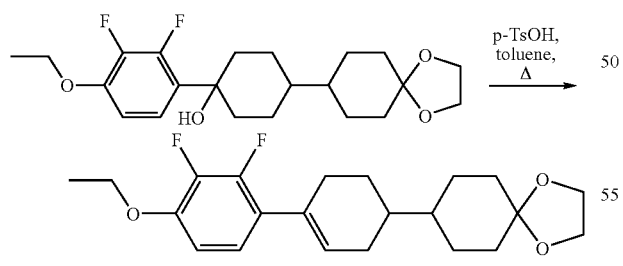

250 g of crude 4-(1,4-dioxaspiro[4.5]dec-8-yl)-1-(4-ethoxy-2,3-difluorophenyl)cyclohexan in 1000 ml of toluene are heated on a water separator for 3 h together with 80.0 ml (1.43 mol) of ethylene glycol with addition of 12.0 g (0.06 mol) of p-toluenesulfonic acid monohydrate. After cooling, the batch is washed successively with water, sat. sodium hydrogencarbonate solution and sat. sodium chloride solution. The solution is dried using sodium sulfate and concentrated to dryness. The crude product is crystallised from acetonitrile, giving 8-[4-(4-ethoxy-2,3-difluorophenyl)cyclohex-3-enyl]-1,4-dioxaspiro[4.5]decane as colourless solid.

7.3 5-(1,4-Dioxaspiro[4.5]dec-8-yl)-2-(4-ethoxy-2,3-difluorophenyl)-cyclohexanol

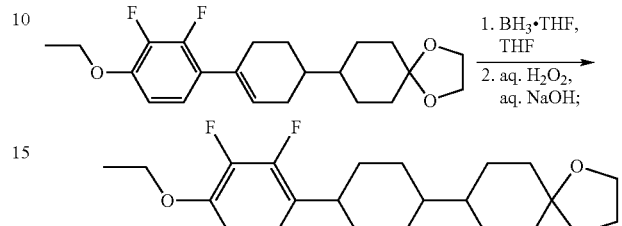

550 ml (0.55 mol) of borane/THF complex (1 M solution) are added at −5° C. to a solution of 154.0 g (0.41 mol) of 8-[4-(4-ethoxy-2,3-difluorophenyl)-cyclohex-3-enyl]-1,4-dioxaspiro[4.5]decane in 1500 ml of THF, and the reaction mixture is stirred at room temperature for 3 h. 99 ml (1.7 mol) of ethanol, 250 ml (1.0 mol) of aqueous sodium hydroxide solution (16%) and 140 ml (1.6 mol) of aqueous hydrogen peroxide soln. (35%) are added successively to the batch, during which the internal temperature does not exceed 46° C. (ice bath). When the addition is complete, the mixture is refluxed for 2 h, and the solution is cooled, added to water and stirred vigorously. The organic phase is separated off, and the aqueous phase is extracted with MTBE. The combined organic phases are washed with sat. sodium chloride solution and dried using sodium sulfate. The solution is concentrated to dryness, and the crude product is purified by column chromatography (SiO$_2$, toluene:ethyl acetate=8:2), giving 5-(1,4-dioxaspiro[4.5]dec-8-yl)-2-(4-ethoxy-2,3-difluorophenyl) cyclohexanol as colourless, viscous oil.

7.4 (±)-(3R*,4aR*,9bS*)-3-(1,4-Dioxaspiro[4.5]dec-8-yl)-7-ethoxy-6-fluoro-1,2,3,4,4a,9b-hexahydrodibenzofuran

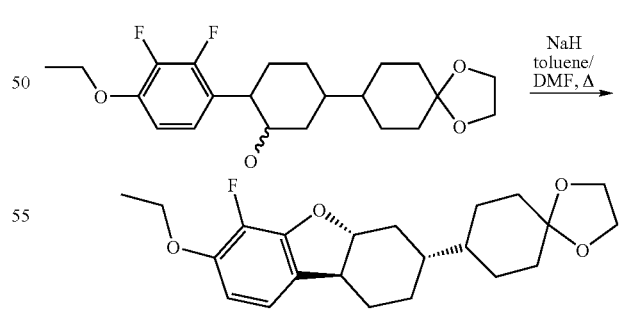

30.0 g (0.75 mol) of sodium hydride (60% suspension in mineral oil) are washed repeatedly with n-pentane and suspended in 2500 ml of toluene. The suspension is heated to 90° C., and a solution of 101.5 g (0.26 mol) of 5-(1,4-dioxaspiro [4.5]dec-8-yl)-2-(4-ethoxy-2,3-difluorophenyl)cyclohexanol in 500 ml of DMF is metered in slowly. The batch is stirred at 90° C. for 20 h, cooled and hydrolysed using water.

The mixture is neutralised by addition of 2 N hydrochloric acid, and the organic phase is separated off. The aqueous phase is extracted with toluene, and the combined organic phases are washed with sat. sodium chloride solution. The solution is dried using sodium sulfate and concentrated to dryness under reduced pressure. The crude product obtained is firstly purified by column chromatography (SiO₂, toluene: ethyl acetate=8:2) and then recrystallised successively from toluene and toluene:ethanol (3:1), giving (±)-(3R*,4aR*, 9bS*)-3-(1,4-dioxaspiro[4.5]dec-8-yl)-7-ethoxy-6-fluoro-1, 2,3,4,4a,9b-hexahydrodibenzofuran as colourless, crystalline solid.

7.5 (±)-4-((3R*,4aR*,9bS*)-7-Ethoxy-6-fluoro-1,2, 3,4,4a,9b-hexahydrodibenzofuran-3-yl)cyclohexanone

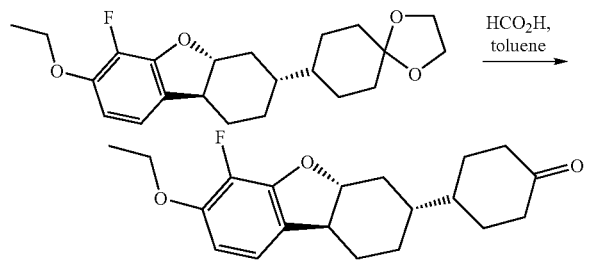

13.3 g (35.3 mmol) of (±)-(3R*,4aR*,9bS*)-3-(1,4-dioxaspiro[4.5]dec-8-yl)-7-ethoxy-6-fluoro-1,2,3,4,4a,9b-hexahydrodibenzofuran are dissolved in 200 ml of toluene and stirred vigorously together with 40 ml (1.06 mol) of formic acid with addition of 1.0 ml (55.6 mmol) of water. After 18 h, the organic phase is separated off, and the formic acid is extracted with toluene. The combined organic phases are washed successively with water, sat. sodium hydrogencarbonate solution and sat. sodium chloride solution and dried using sodium sulfate. The crude product remaining after removal of the solvent is purified by column chromatography (SiO₂, toluene:ethyl acetate=4:1), giving (±)-4-((3R*,4aR*, 9bS*)-7-ethoxy-6-fluoro-1,2,3,4,4a,9b-hexahydrodibenzofuran-3-yl)cyclohexanone as colourless solid.

7.6 (±)-(3R*,4aR*,9bS*)-7-Ethoxy-6-fluoro-3-(4-methoxymethylene-cyclohexyl)-1,2,3,4,4a,9b-hexahydrodibenzofuran

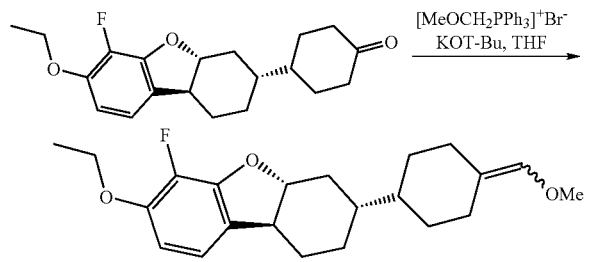

14.1 g (41.3 mmol) of methoxymethyltriphenylphosphonium chloride are initially introduced in 250 ml of THF, and a solution of 4.6 g (41.0 mmol) of potassium tert-butoxide in 100 ml of THF is added at 0° C. After 30 min at this temperature, (±)-4-((3R*,4aR*,9bS*)-7-ethoxy-6-fluoro-1,2,3,4,4a, 9b-hexahydrodibenzofuran-3-yl)cyclohexanone as a solution in 150 ml of THF is added, and the batch is stirred at room temperature for 17 h. The mixture is treated with water at 0° C. and acidified using 2 N hydrochloric acid. The batch is extracted with MTBE, and the combined extracts are washed with sat. sodium chloride solution. The solution is dried using sodium sulfate and concentrated to dryness. Purification of the crude product by column chromatography (SiO₂, toluene: ethyl acetate=95:5) gives (±)-(3R*,4aR*,9bS*)-7-ethoxy-6-fluoro-3-(4-methoxymethylene-cyclohexyl)-1,2,3,4,4a,9b-hexahydrodibenzofuran as colourless solid.

7.7 (±)-4-((3R*,4aR*,9bS*)-7-Ethoxy-6-fluoro-1,2, 3,4,4a,9b-hexahydro-dibenzofuran-3-yl)cyclohexanecarbaldehyde

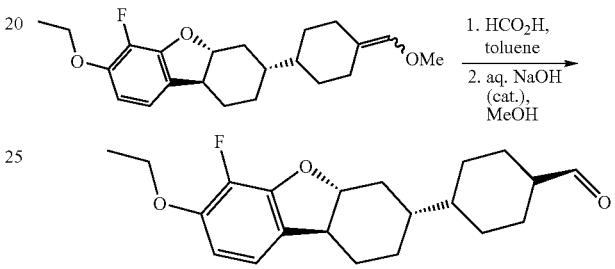

10.0 g (27.7 mmol) of (±)-(3R*,4aR*,9bS*)-7-ethoxy-6-fluoro-3-(4-methoxy-methylenecyclohexyl)-1,2,3,4,4a,9b-hexahydrodibenzofuran are dissolved in 400 ml of toluene and stirred vigorously at room temperature for 18 h together with 30 ml (0.80 mol) of formic acid and 1.0 ml (55.6 mmol) of water. The organic phase is separated off and washed successively with water, sat. sodium hydrogencarbonate solution and sat. sodium chloride solution. The solution is dried using sodium sulfate and concentrated to dryness.

The residue is dissolved in 250 ml of methanol/THF mixture (5:2), and 0.44 ml (3.0 mmol) of aqueous sodium hydroxide solution (20%) is added dropwise. After 3 h at room temperature, the solution is added to water and acidified using 2 N hydrochloric acid. The batch is extracted with MTBE, and the combined organic phases are washed with sat. sodium chloride solution. The solution is dried using sodium sulfate and concentrated to dryness. The crude product from the reaction is used directly for the following steps.

7.8 (±)-(3R*,4aR*,9bS*)-7-Ethoxy-6-fluoro-3-(4-vinylcyclohexyl)-1,2,3,4,4a,9b-hexahydrodibenzofuran

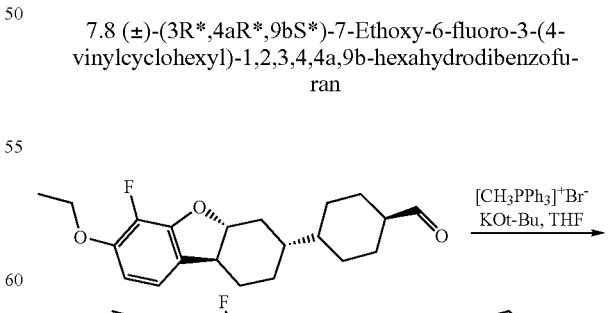

9.65 g (27.0 mmol) of methyltriphenylphosphonium bromide are initially introduced in 100 ml of THF, and 3.09 g (27.0 mmol) of potassium tert-butoxide in 60 ml of THF are added at −5° C. After 1 h at this temperature, 8.40 g (about 24 mmol) of crude (±)-4-((3R*,4aR*,9bS*)-7-ethoxy-6-fluoro-1,2,3,4,4a,9b-hexahydrodibenzofuran-3-yl)cyclohexanecarbaldehyde as a solution in 90 ml of THF are added dropwise, and the batch is stirred at room temperature for 3 h. The reaction solution is hydrolysed using water and acidified using 2 N HCl. The mixture is extracted with MTBE, and the combined organic phases are dried using sodium sulfate. The crude product remaining after removal of the solvents is filtered adsorptively (SiO$_2$, toluene), and the filtrate is concentrated to dryness. Repeated recrystallisation of the residue from ethanol gives (±)-(3R*,4aR*,9bS*)-7-ethoxy-6-fluoro-3-(4-vinylcyclohexyl)-1,2,3,4,4a,9b-hexahydrodibenzofuran as colourless solid (m.p. 132° C.).

C 132 N 157 I

Δε=−6.7

Δn=0.121

γ$_1$=911 mPa·s

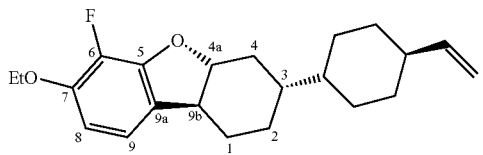

$^1$H-NMR (250 MHz, CHCl$_3$): δ=6.74 (dm, 1H, J=7.8 Hz, 9-H), 6.45 (dd, 1H, J=8.0 Hz, J=7.0 Hz, 8-H), 5.84-5.71 (m, 1H, H$_{vinyl.}$), 5.00-4.86 (m, 2H, H$_{vinyl.}$), 4.07 (q, 2H, J=7.0 Hz, OCH$_2$CH$_3$), 4.00-3.89 (m, 1H, 4a-H), 2.78-2.67 (m, 1H, H$_{aliph.}$), 2.41-2.27 (m, 2H, H$_{aliph.}$), 1.91-1.74 (m, 7H, H$_{aliph.}$), 1.67-1.63 (m, 1H, H$_{aliph.}$), 1.42 (t, 3H, J=7.0 Hz, OCH$_2$CH$_3$), 1.36-1.06 (m, 7H, H$_{aliph.}$)

MS (EI): m/e (%)=344 (100, M$^+$).

The following compounds are obtained analogously to the examples indicated using the corresponding precursors (Examples 1-1014; Tables 1 to 4, data Table 5):

Analogously to Example 1: Examples 8 to 62:

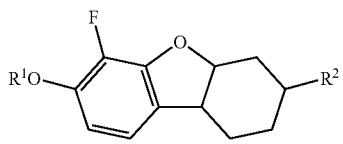

Analogously to Example 1: Examples 63 to 117:

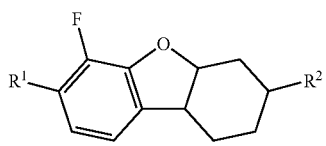

Analogously to Examples 3, 4 and 5: Examples 118 to 173:

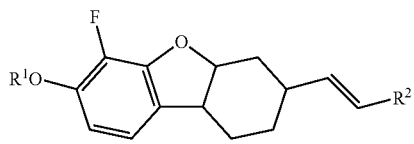

Analogously to Examples 3, 4 and 5: Examples 173 to 227:

TABLE 1

| Ex. | R$^1$ | R$^2$ |
|---|---|---|
| 8 | CH$_3$ | H |
| 9 | CH$_3$ | CH$_3$ |
| 10 | CH$_3$ | C$_2$H$_5$ |
| 11 | CH$_3$ | n-C$_3$H$_7$ |
| 12 | CH$_3$ | n-C$_4$H$_9$ |
| 13 | CH$_3$ | n-C$_5$H$_{11}$ |
| 14 | CH$_3$ | n-C$_6$H$_{13}$ |
| 15 | CH$_3$ | n-C$_7$H$_{15}$ |
| 16 | C$_2$H$_5$ | H |
| 17 | C$_2$H$_5$ | CH$_3$ |
| 18 | C$_2$H$_5$ | C$_2$H$_5$ |
| 19 | C$_2$H$_5$ | n-C$_3$H$_7$ |
| 20 | C$_2$H$_5$ | n-C$_4$H$_9$ |
| 21 | C$_2$H$_5$ | n-C$_5$H$_{11}$ |
| 22 | C$_2$H$_5$ | n-C$_6$H$_{13}$ |
| 23 | C$_2$H$_5$ | n-C$_7$H$_{15}$ |
| 24 | n-C$_3$H$_7$ | H |
| 25 | n-C$_3$H$_7$ | CH$_3$ |
| 26 | n-C$_3$H$_7$ | C$_2$H$_5$ |
| 27 | n-C$_3$H$_7$ | n-C$_4$H$_9$ |
| 28 | n-C$_3$H$_7$ | n-C$_5$H$_{11}$ |
| 29 | n-C$_3$H$_7$ | n-C$_6$H$_{13}$ |
| 30 | n-C$_3$H$_7$ | n-C$_7$H$_{15}$ |
| 31 | n-C$_4$H$_9$ | H |
| 32 | n-C$_4$H$_9$ | CH$_3$ |
| 33 | n-C$_4$H$_9$ | C$_2$H$_5$ |
| 34 | n-C$_4$H$_9$ | n-C$_3$H$_7$ |
| 35 | n-C$_4$H$_9$ | n-C$_4$H$_9$ |
| 36 | n-C$_4$H$_9$ | n-C$_5$H$_{11}$ |
| 37 | n-C$_4$H$_9$ | n-C$_6$H$_{13}$ |
| 38 | n-C$_4$H$_9$ | n-C$_7$H$_{15}$ |
| 39 | n-C$_5$H$_{11}$ | H |
| 40 | n-C$_5$H$_{11}$ | CH$_3$ |
| 41 | n-C$_5$H$_{11}$ | C$_2$H$_5$ |
| 42 | n-C$_5$H$_{11}$ | n-C$_3$H$_7$ |
| 43 | n-C$_5$H$_{11}$ | n-C$_4$H$_9$ |
| 44 | n-C$_5$H$_{11}$ | n-C$_5$H$_{11}$ |
| 45 | n-C$_5$H$_{11}$ | n-C$_6$H$_{13}$ |
| 46 | n-C$_5$H$_{11}$ | n-C$_7$H$_{15}$ |
| 47 | n-C$_6$H$_{13}$ | H |
| 48 | n-C$_6$H$_{13}$ | CH$_3$ |
| 49 | n-C$_6$H$_{13}$ | C$_2$H$_5$ |
| 50 | n-C$_6$H$_{13}$ | n-C$_3$H$_7$ |
| 51 | n-C$_6$H$_{13}$ | n-C$_4$H$_9$ |
| 52 | n-C$_6$H$_{13}$ | n-C$_5$H$_{11}$ |
| 53 | n-C$_6$H$_{13}$ | n-C$_6$H$_{13}$ |
| 54 | n-C$_6$H$_{13}$ | n-C$_7$H$_{15}$ |
| 55 | n-C$_7$H$_{15}$ | H |
| 56 | n-C$_7$H$_{15}$ | CH$_3$ |
| 57 | n-C$_7$H$_{15}$ | C$_2$H$_5$ |
| 58 | n-C$_7$H$_{15}$ | n-C$_3$H$_7$ |
| 59 | n-C$_7$H$_{15}$ | n-C$_4$H$_9$ |
| 60 | n-C$_7$H$_{15}$ | n-C$_5$H$_{11}$ |
| 61 | n-C$_7$H$_{15}$ | n-C$_6$H$_{13}$ |
| 62 | n-C$_7$H$_{15}$ | n-C$_7$H$_{15}$ |
| 63 | CH$_3$ | H |

TABLE 1-continued

[Structure: fluoro-substituted dibenzofuran with R¹ and R² groups, vinyl linker]

| Ex. | R¹ | R² |
|---|---|---|
| 64 | CH₃ | CH₃ |
| 65 | CH₃ | C₂H₅ |
| 66 | CH₃ | n-C₃H₇ |
| 67 | CH₃ | n-C₄H₉ |
| 68 | CH₃ | n-C₅H₁₁ |
| 69 | CH₃ | n-C₆H₁₃ |
| 70 | CH₃ | n-C₇H₁₅ |
| 71 | C₂H₅ | H |
| 72 | C₂H₅ | CH₃ |
| 73 | C₂H₅ | C₂H₅ |
| 74 | C₂H₅ | n-C₃H₇ |
| 75 | C₂H₅ | n-C₄H₉ |
| 76 | C₂H₅ | n-C₅H₁₁ |
| 77 | C₂H₅ | n-C₆H₁₃ |
| 78 | C₂H₅ | n-C₇H₁₅ |
| 79 | n-C₃H₇ | H |
| 80 | n-C₃H₇ | CH₃ |
| 81 | n-C₃H₇ | C₂H₅ |
| 82 | n-C₃H₇ | n-C₄H₉ |
| 83 | n-C₃H₇ | n-C₅H₁₁ |
| 84 | n-C₃H₇ | n-C₆H₁₃ |
| 85 | n-C₃H₇ | n-C₇H₁₅ |
| 86 | n-C₄H₉ | H |
| 87 | n-C₄H₉ | CH₃ |
| 88 | n-C₄H₉ | C₂H₅ |
| 89 | n-C₄H₉ | n-C₃H₇ |
| 90 | n-C₄H₉ | n-C₄H₉ |
| 91 | n-C₄H₉ | n-C₅H₁₁ |
| 92 | n-C₄H₉ | n-C₆H₁₃ |
| 93 | n-C₄H₉ | n-C₇H₁₅ |
| 94 | n-C₅H₁₁ | H |
| 95 | n-C₅H₁₁ | CH₃ |
| 96 | n-C₅H₁₁ | C₂H₅ |
| 97 | n-C₅H₁₁ | n-C₃H₇ |
| 98 | n-C₅H₁₁ | n-C₄H₉ |
| 99 | n-C₅H₁₁ | n-C₅H₁₁ |
| 100 | n-C₅H₁₁ | n-C₆H₁₃ |
| 101 | n-C₅H₁₁ | n-C₇H₁₅ |
| 102 | n-C₆H₁₃ | H |
| 103 | n-C₆H₁₃ | CH₃ |
| 104 | n-C₆H₁₃ | C₂H₅ |
| 105 | n-C₆H₁₃ | n-C₃H₇ |
| 106 | n-C₆H₁₃ | n-C₄H₉ |
| 107 | n-C₆H₁₃ | n-C₅H₁₁ |
| 108 | n-C₆H₁₃ | n-C₆H₁₃ |
| 109 | n-C₆H₁₃ | n-C₇H₁₅ |
| 110 | n-C₇H₁₅ | H |
| 111 | n-C₇H₁₅ | CH₃ |
| 112 | n-C₇H₁₅ | C₂H₅ |
| 113 | n-C₇H₁₅ | n-C₃H₇ |
| 114 | n-C₇H₁₅ | n-C₄H₉ |
| 115 | n-C₇H₁₅ | n-C₅H₁₁ |
| 116 | n-C₇H₁₅ | n-C₆H₁₃ |
| 117 | n-C₇H₁₅ | n-C₇H₁₅ |
| 118 | CH₃ | H |
| 119 | CH₃ | CH₃ |
| 120 | CH₃ | C₂H₅ |
| 121 | CH₃ | n-C₃H₇ |
| 122 | CH₃ | n-C₄H₉ |
| 123 | CH₃ | n-C₅H₁₁ |
| 124 | CH₃ | n-C₆H₁₃ |
| 125 | CH₃ | n-C₇H₁₅ |
| 126 | C₂H₅ | H |
| 127 | C₂H₅ | CH₃ |
| 128 | C₂H₅ | C₂H₅ |
| 129 | C₂H₅ | n-C₃H₇ |
| 130 | C₂H₅ | n-C₄H₉ |
| 131 | C₂H₅ | n-C₅H₁₁ |
| 132 | C₂H₅ | n-C₆H₁₃ |
| 133 | C₂H₅ | n-C₇H₁₅ |
| 134 | n-C₃H₇ | H |
| 135 | n-C₃H₇ | CH₃ |
| 136 | n-C₃H₇ | C₂H₅ |
| 137 | n-C₃H₇ | n-C₄H₉ |
| 138 | n-C₃H₇ | n-C₅H₁₁ |
| 139 | n-C₃H₇ | n-C₆H₁₃ |
| 140 | n-C₃H₇ | n-C₇H₁₅ |
| 141 | n-C₄H₉ | H |
| 142 | n-C₄H₉ | CH₃ |
| 143 | n-C₄H₉ | C₂H₅ |
| 144 | n-C₄H₉ | n-C₃H₇ |
| 145 | n-C₄H₉ | n-C₄H₉ |
| 146 | n-C₄H₉ | n-C₅H₁₁ |
| 147 | n-C₄H₉ | n-C₆H₁₃ |
| 148 | n-C₄H₉ | n-C₇H₁₅ |
| 149 | n-C₅H₁₁ | H |
| 150 | n-C₅H₁₁ | CH₃ |
| 151 | n-C₅H₁₁ | C₂H₅ |
| 152 | n-C₅H₁₁ | n-C₃H₇ |
| 153 | n-C₅H₁₁ | n-C₄H₉ |
| 154 | n-C₅H₁₁ | n-C₅H₁₁ |
| 155 | n-C₅H₁₁ | n-C₆H₁₃ |
| 156 | n-C₅H₁₁ | n-C₇H₁₅ |
| 157 | n-C₆H₁₃ | H |
| 158 | n-C₆H₁₃ | CH₃ |
| 159 | n-C₆H₁₃ | C₂H₅ |
| 160 | n-C₆H₁₃ | n-C₃H₇ |
| 161 | n-C₆H₁₃ | n-C₄H₉ |
| 162 | n-C₆H₁₃ | n-C₅H₁₁ |
| 163 | n-C₆H₁₃ | n-C₆H₁₃ |
| 164 | n-C₆H₁₃ | n-C₇H₁₅ |
| 165 | n-C₇H₁₅ | H |
| 166 | n-C₇H₁₅ | CH₃ |
| 167 | n-C₇H₁₅ | C₂H₅ |
| 168 | n-C₇H₁₅ | n-C₃H₇ |
| 169 | n-C₇H₁₅ | n-C₄H₉ |
| 170 | n-C₇H₁₅ | n-C₅H₁₁ |
| 171 | n-C₇H₁₅ | n-C₆H₁₃ |
| 172 | n-C₇H₁₅ | n-C₇H₁₅ |
| 173 | CH₃ | H |
| 174 | CH₃ | CH₃ |
| 175 | CH₃ | C₂H₅ |
| 176 | CH₃ | n-C₃H₇ |
| 177 | CH₃ | n-C₄H₉ |
| 178 | CH₃ | n-C₅H₁₁ |
| 179 | CH₃ | n-C₆H₁₃ |
| 180 | CH₃ | n-C₇H₁₅ |
| 181 | C₂H₅ | H |
| 182 | C₂H₅ | CH₃ |
| 183 | C₂H₅ | C₂H₅ |
| 184 | C₂H₅ | n-C₃H₇ |
| 185 | C₂H₅ | n-C₄H₉ |
| 186 | C₂H₅ | n-C₅H₁₁ |
| 187 | C₂H₅ | n-C₆H₁₃ |
| 188 | C₂H₅ | n-C₇H₁₅ |
| 189 | n-C₃H₇ | H |
| 190 | n-C₃H₇ | CH₃ |
| 191 | n-C₃H₇ | C₂H₅ |
| 192 | n-C₃H₇ | n-C₄H₉ |
| 193 | n-C₃H₇ | n-C₅H₁₁ |
| 194 | n-C₃H₇ | n-C₆H₁₃ |
| 195 | n-C₃H₇ | n-C₇H₁₅ |
| 196 | n-C₄H₉ | H |
| 197 | n-C₄H₉ | CH₃ |
| 198 | n-C₄H₉ | C₂H₅ |
| 199 | n-C₄H₉ | n-C₃H₇ |
| 200 | n-C₄H₉ | n-C₄H₉ |
| 201 | n-C₄H₉ | n-C₅H₁₁ |

TABLE 1-continued

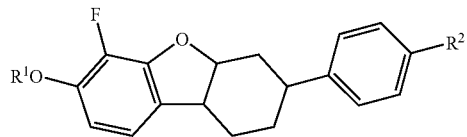

| Ex. | R¹ | R² |
|---|---|---|
| 202 | n-C₄H₉ | n-C₆H₁₃ |
| 203 | n-C₄H₉ | n-C₇H₁₅ |
| 204 | n-C₅H₁₁ | H |
| 205 | n-C₅H₁₁ | CH₃ |
| 206 | n-C₅H₁₁ | C₂H₅ |
| 207 | n-C₅H₁₁ | n-C₃H₇ |
| 208 | n-C₅H₁₁ | n-C₄H₉ |
| 209 | n-C₅H₁₁ | n-C₅H₁₁ |
| 210 | n-C₅H₁₁ | n-C₆H₁₃ |
| 211 | n-C₅H₁₁ | n-C₇H₁₅ |
| 212 | n-C₆H₁₃ | H |
| 213 | n-C₆H₁₃ | CH₃ |
| 214 | n-C₆H₁₃ | C₂H₅ |
| 215 | n-C₆H₁₃ | n-C₃H₇ |
| 216 | n-C₆H₁₃ | n-C₄H₉ |
| 217 | n-C₆H₁₃ | n-C₅H₁₁ |
| 218 | n-C₆H₁₃ | n-C₆H₁₃ |
| 219 | n-C₆H₁₃ | n-C₇H₁₅ |
| 220 | n-C₇H₁₅ | H |
| 221 | n-C₇H₁₅ | CH₃ |
| 222 | n-C₇H₁₅ | C₂H₅ |
| 223 | n-C₇H₁₅ | n-C₃H₇ |
| 224 | n-C₇H₁₅ | n-C₄H₉ |
| 225 | n-C₇H₁₅ | n-C₅H₁₁ |
| 226 | n-C₇H₁₅ | n-C₆H₁₃ |
| 227 | n-C₇H₁₅ | n-C₇H₁₅ |

Analogously to Example 2: Examples 228 to 282:

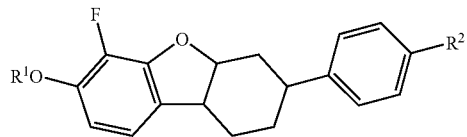

Analogously to Example 2: Examples 283 to 337:

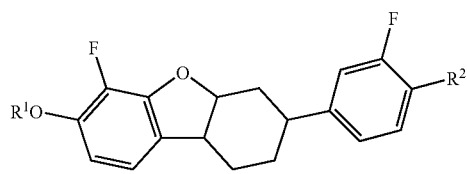

Analogously to Example 2: Examples 338 to 392:

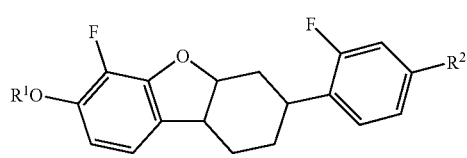

Analogously to Example 2: Examples 393 to 447:

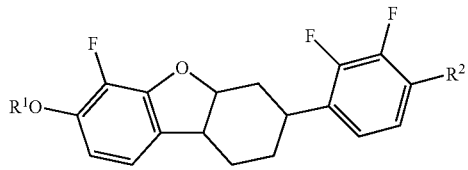

Analogously to Example 2: Examples 448 to 502:

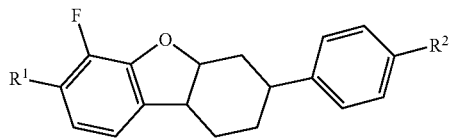

Analogously to Example 2: Examples 503 to 557:

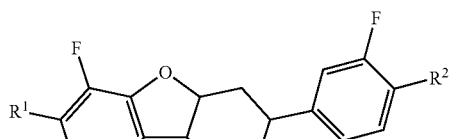

Analogously to Example 2: Examples 558 to 612:

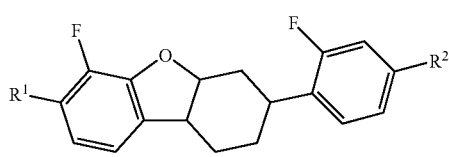

Analogously to Example 2: Examples 613 to 667:

TABLE 2

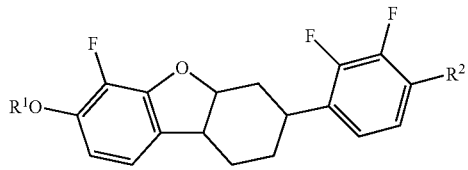

| Ex. | R¹ | R² |
|---|---|---|
| 228 | CH₃ | H |
| 229 | CH₃ | CH₃ |
| 230 | CH₃ | C₂H₅ |
| 231 | CH₃ | n-C₃H₇ |
| 232 | CH₃ | n-C₄H₉ |
| 233 | CH₃ | n-C₅H₁₁ |
| 234 | CH₃ | n-C₆H₁₃ |
| 235 | CH₃ | n-C₇H₁₅ |
| 236 | C₂H₅ | H |
| 237 | C₂H₅ | CH₃ |
| 238 | C₂H₅ | C₂H₅ |
| 239 | C₂H₅ | n-C₃H₇ |
| 240 | C₂H₅ | n-C₄H₉ |
| 241 | C₂H₅ | n-C₅H₁₁ |
| 242 | C₂H₅ | n-C₆H₁₃ |
| 243 | C₂H₅ | n-C₇H₁₅ |

TABLE 2-continued

| Ex. | R¹ | R² |
|---|---|---|
| 244 | n-C₃H₇ | H |
| 245 | n-C₃H₇ | CH₃ |
| 246 | n-C₃H₇ | C₂H₅ |
| 247 | n-C₃H₇ | n-C₄H₉ |
| 248 | n-C₃H₇ | n-C₅H₁₁ |
| 249 | n-C₃H₇ | n-C₆H₁₃ |
| 250 | n-C₃H₇ | n-C₇H₁₅ |
| 251 | n-C₄H₉ | H |
| 252 | n-C₄H₉ | CH₃ |
| 253 | n-C₄H₉ | C₂H₅ |
| 254 | n-C₄H₉ | n-C₃H₇ |
| 255 | n-C₄H₉ | n-C₄H₉ |
| 256 | n-C₄H₉ | n-C₅H₁₁ |
| 257 | n-C₄H₉ | n-C₆H₁₃ |
| 258 | n-C₄H₉ | n-C₇H₁₅ |
| 259 | n-C₅H₁₁ | H |
| 260 | n-C₅H₁₁ | CH₃ |
| 261 | n-C₅H₁₁ | C₂H₅ |
| 262 | n-C₅H₁₁ | n-C₃H₇ |
| 263 | n-C₅H₁₁ | n-C₄H₉ |
| 264 | n-C₅H₁₁ | n-C₅H₁₁ |
| 265 | n-C₅H₁₁ | n-C₆H₁₃ |
| 266 | n-C₅H₁₁ | n-C₇H₁₅ |
| 267 | n-C₆H₁₃ | H |
| 268 | n-C₆H₁₃ | CH₃ |
| 269 | n-C₆H₁₃ | C₂H₅ |
| 270 | n-C₆H₁₃ | n-C₃H₇ |
| 271 | n-C₆H₁₃ | n-C₄H₉ |
| 272 | n-C₆H₁₃ | n-C₅H₁₁ |
| 273 | n-C₆H₁₃ | n-C₆H₁₃ |
| 274 | n-C₆H₁₃ | n-C₇H₁₅ |
| 275 | n-C₇H₁₅ | H |
| 276 | n-C₇H₁₅ | CH₃ |
| 277 | n-C₇H₁₅ | C₂H₅ |
| 278 | n-C₇H₁₅ | n-C₃H₇ |
| 279 | n-C₇H₁₅ | n-C₄H₉ |
| 280 | n-C₇H₁₅ | n-C₅H₁₁ |
| 281 | n-C₇H₁₅ | n-C₆H₁₃ |
| 282 | n-C₇H₁₅ | n-C₇H₁₅ |
| 283 | CH₃ | H |
| 284 | CH₃ | CH₃ |
| 285 | CH₃ | C₂H₅ |
| 286 | CH₃ | n-C₃H₇ |
| 287 | CH₃ | n-C₄H₉ |
| 288 | CH₃ | n-C₅H₁₁ |
| 289 | CH₃ | n-C₆H₁₃ |
| 290 | CH₃ | n-C₇H₁₅ |
| 291 | C₂H₅ | H |
| 292 | C₂H₅ | CH₃ |
| 293 | C₂H₅ | C₂H₅ |
| 294 | C₂H₅ | n-C₃H₇ |
| 295 | C₂H₅ | n-C₄H₉ |
| 296 | C₂H₅ | n-C₅H₁₁ |
| 297 | C₂H₅ | n-C₆H₁₃ |
| 298 | C₂H₅ | n-C₇H₁₅ |
| 299 | n-C₃H₇ | H |
| 300 | n-C₃H₇ | CH₃ |
| 301 | n-C₃H₇ | C₂H₅ |
| 302 | n-C₃H₇ | n-C₄H₉ |
| 303 | n-C₃H₇ | n-C₅H₁₁ |
| 304 | n-C₃H₇ | n-C₆H₁₃ |
| 305 | n-C₃H₇ | n-C₇H₁₅ |
| 306 | n-C₄H₉ | H |
| 307 | n-C₄H₉ | CH₃ |
| 308 | n-C₄H₉ | C₂H₅ |
| 309 | n-C₄H₉ | n-C₃H₇ |
| 310 | n-C₄H₉ | n-C₄H₉ |
| 311 | n-C₄H₉ | n-C₅H₁₁ |
| 312 | n-C₄H₉ | n-C₆H₁₃ |
| 313 | n-C₄H₉ | n-C₇H₁₅ |
| 314 | n-C₅H₁₁ | H |
| 315 | n-C₅H₁₁ | CH₃ |
| 316 | n-C₅H₁₁ | C₂H₅ |
| 317 | n-C₅H₁₁ | C₂H₅ |
| 318 | n-C₅H₁₁ | n-C₄H₉ |
| 319 | n-C₅H₁₁ | n-C₅H₁₁ |
| 320 | n-C₅H₁₁ | n-C₆H₁₃ |
| 321 | n-C₅H₁₁ | n-C₇H₁₅ |
| 322 | n-C₆H₁₃ | H |
| 323 | n-C₆H₁₃ | CH₃ |
| 324 | n-C₆H₁₃ | C₂H₅ |
| 325 | n-C₆H₁₃ | n-C₃H₇ |
| 326 | n-C₆H₁₃ | n-C₄H₉ |
| 327 | n-C₆H₁₃ | n-C₅H₁₁ |
| 328 | n-C₆H₁₃ | n-C₆H₁₃ |
| 329 | n-C₆H₁₃ | n-C₇H₁₅ |
| 330 | n-C₇H₁₅ | H |
| 331 | n-C₇H₁₅ | CH₃ |
| 332 | n-C₇H₁₅ | C₂H₅ |
| 333 | n-C₇H₁₅ | n-C₃H₇ |
| 334 | n-C₇H₁₅ | n-C₄H₉ |
| 335 | n-C₇H₁₅ | n-C₅H₁₁ |
| 336 | n-C₇H₁₅ | n-C₆H₁₃ |
| 337 | n-C₇H₁₅ | n-C₇H₁₅ |
| 338 | CH₃ | H |
| 339 | CH₃ | CH₃ |
| 340 | CH₃ | C₂H₅ |
| 341 | CH₃ | n-C₃H₇ |
| 342 | CH₃ | n-C₄H₉ |
| 343 | CH₃ | n-C₅H₁₁ |
| 344 | CH₃ | n-C₆H₁₃ |
| 345 | CH₃ | n-C₇H₁₅ |
| 346 | C₂H₅ | H |
| 347 | C₂H₅ | CH₃ |
| 348 | C₂H₅ | C₂H₅ |
| 349 | C₂H₅ | n-C₃H₇ |
| 350 | C₂H₅ | n-C₄H₉ |
| 351 | C₂H₅ | n-C₅H₁₁ |
| 352 | C₂H₅ | n-C₆H₁₃ |
| 353 | C₂H₅ | n-C₇H₁₅ |
| 354 | n-C₃H₇ | H |
| 355 | n-C₃H₇ | CH₃ |
| 356 | n-C₃H₇ | C₂H₅ |
| 357 | n-C₃H₇ | n-C₄H₉ |
| 358 | n-C₃H₇ | n-C₅H₁₁ |
| 359 | n-C₃H₇ | n-C₆H₁₃ |
| 360 | n-C₃H₇ | n-C₇H₁₅ |
| 361 | n-C₄H₉ | H |
| 362 | n-C₄H₉ | CH₃ |
| 363 | n-C₄H₉ | C₂H₅ |
| 364 | n-C₄H₉ | n-C₃H₇ |
| 365 | n-C₄H₉ | n-C₄H₉ |
| 366 | n-C₄H₉ | n-C₅H₁₁ |
| 367 | n-C₄H₉ | n-C₆H₁₃ |
| 368 | n-C₄H₉ | n-C₇H₁₅ |
| 369 | n-C₅H₁₁ | H |
| 370 | n-C₅H₁₁ | CH₃ |
| 371 | n-C₅H₁₁ | C₂H₅ |
| 372 | n-C₅H₁₁ | n-C₃H₇ |
| 373 | n-C₅H₁₁ | n-C₄H₉ |
| 374 | n-C₅H₁₁ | n-C₅H₁₁ |
| 375 | n-C₅H₁₁ | n-C₆H₁₃ |
| 376 | n-C₅H₁₁ | n-C₇H₁₅ |
| 377 | n-C₆H₁₃ | H |
| 378 | n-C₆H₁₃ | CH₃ |
| 379 | n-C₆H₁₃ | C₂H₅ |

TABLE 2-continued

[Structure: dibenzofuran core with F substituents, R¹ and R² groups]

| Ex. | R¹ | R² |
|---|---|---|
| 380 | n-C$_6$H$_{13}$ | n-C$_3$H$_7$ |
| 381 | n-C$_6$H$_{13}$ | n-C$_4$H$_9$ |
| 382 | n-C$_6$H$_{13}$ | n-C$_5$H$_{11}$ |
| 383 | n-C$_6$H$_{13}$ | n-C$_6$H$_{13}$ |
| 384 | n-C$_6$H$_{13}$ | n-C$_7$H$_{15}$ |
| 385 | n-C$_7$H$_{15}$ | H |
| 386 | n-C$_7$H$_{15}$ | CH$_3$ |
| 387 | n-C$_7$H$_{15}$ | C$_2$H$_5$ |
| 388 | n-C$_7$H$_{15}$ | n-C$_3$H$_7$ |
| 389 | n-C$_7$H$_{15}$ | n-C$_4$H$_9$ |
| 390 | n-C$_7$H$_{15}$ | n-C$_5$H$_{11}$ |
| 391 | n-C$_7$H$_{15}$ | n-C$_6$H$_{13}$ |
| 392 | n-C$_7$H$_{15}$ | n-C$_7$H$_{15}$ |
| 393 | CH$_3$ | H |
| 394 | CH$_3$ | CH$_3$ |
| 395 | CH$_3$ | C$_2$H$_5$ |
| 396 | CH$_3$ | n-C$_3$H$_7$ |
| 397 | CH$_3$ | n-C$_4$H$_9$ |
| 398 | CH$_3$ | n-C$_5$H$_{11}$ |
| 399 | CH$_3$ | n-C$_6$H$_{13}$ |
| 400 | CH$_3$ | n-C$_7$H$_{15}$ |
| 401 | C$_2$H$_5$ | H |
| 402 | C$_2$H$_5$ | CH$_3$ |
| 403 | C$_2$H$_5$ | C$_2$H$_5$ |
| 404 | C$_2$H$_5$ | n-C$_3$H$_7$ |
| 405 | C$_2$H$_5$ | n-C$_4$H$_9$ |
| 406 | C$_2$H$_5$ | n-C$_5$H$_{11}$ |
| 407 | C$_2$H$_5$ | n-C$_6$H$_{13}$ |
| 408 | C$_2$H$_5$ | n-C$_7$H$_{15}$ |
| 409 | n-C$_3$H$_7$ | H |
| 410 | n-C$_3$H$_7$ | CH$_3$ |
| 411 | n-C$_3$H$_7$ | C$_2$H$_5$ |
| 412 | n-C$_3$H$_7$ | n-C$_4$H$_9$ |
| 413 | n-C$_3$H$_7$ | n-C$_5$H$_{11}$ |
| 414 | n-C$_3$H$_7$ | n-C$_6$H$_{13}$ |
| 415 | n-C$_3$H$_7$ | n-C$_7$H$_{15}$ |
| 416 | n-C$_4$H$_9$ | H |
| 417 | n-C$_4$H$_9$ | CH$_3$ |
| 418 | n-C$_4$H$_9$ | C$_2$H$_5$ |
| 419 | n-C$_4$H$_9$ | n-C$_3$H$_7$ |
| 420 | n-C$_4$H$_9$ | n-C$_4$H$_9$ |
| 421 | n-C$_4$H$_9$ | n-C$_5$H$_{11}$ |
| 422 | n-C$_4$H$_9$ | n-C$_6$H$_{13}$ |
| 423 | n-C$_4$H$_9$ | n-C$_7$H$_{15}$ |
| 424 | n-C$_5$H$_{11}$ | H |
| 425 | n-C$_5$H$_{11}$ | CH$_3$ |
| 426 | n-C$_5$H$_{11}$ | C$_2$H$_5$ |
| 427 | n-C$_5$H$_{11}$ | n-C$_3$H$_7$ |
| 428 | n-C$_5$H$_{11}$ | n-C$_4$H$_9$ |
| 429 | n-C$_5$H$_{11}$ | n-C$_5$H$_{11}$ |
| 430 | n-C$_5$H$_{11}$ | n-C$_6$H$_{13}$ |
| 431 | n-C$_5$H$_{11}$ | n-C$_7$H$_{15}$ |
| 432 | n-C$_6$H$_{13}$ | H |
| 433 | n-C$_6$H$_{13}$ | CH$_3$ |
| 434 | n-C$_6$H$_{13}$ | C$_2$H$_5$ |
| 435 | n-C$_6$H$_{13}$ | n-C$_3$H$_7$ |
| 436 | n-C$_6$H$_{13}$ | n-C$_4$H$_9$ |
| 437 | n-C$_6$H$_{13}$ | n-C$_5$H$_{11}$ |
| 438 | n-C$_6$H$_{13}$ | n-C$_6$H$_{13}$ |
| 439 | n-C$_6$H$_{13}$ | n-C$_7$H$_{15}$ |
| 440 | n-C$_7$H$_{15}$ | H |
| 441 | n-C$_7$H$_{15}$ | CH$_3$ |
| 442 | n-C$_7$H$_{15}$ | C$_2$H$_5$ |
| 443 | n-C$_7$H$_{15}$ | n-C$_3$H$_7$ |
| 444 | n-C$_7$H$_{15}$ | n-C$_4$H$_9$ |
| 445 | n-C$_7$H$_{15}$ | n-C$_5$H$_{11}$ |
| 446 | n-C$_7$H$_{15}$ | n-C$_6$H$_{13}$ |
| 447 | n-C$_7$H$_{15}$ | n-C$_7$H$_{15}$ |
| 448 | CH$_3$ | H |
| 449 | CH$_3$ | CH$_3$ |
| 450 | CH$_3$ | C$_2$H$_5$ |
| 451 | CH$_3$ | n-C$_3$H$_7$ |
| 452 | CH$_3$ | n-C$_4$H$_9$ |
| 453 | CH$_3$ | n-C$_5$H$_{11}$ |
| 454 | CH$_3$ | n-C$_6$H$_{13}$ |
| 455 | CH$_3$ | n-C$_7$H$_{15}$ |
| 456 | C$_2$H$_5$ | H |
| 457 | C$_2$H$_5$ | CH$_3$ |
| 458 | C$_2$H$_5$ | C$_2$H$_5$ |
| 459 | C$_2$H$_5$ | n-C$_3$H$_7$ |
| 460 | C$_2$H$_5$ | n-C$_4$H$_9$ |
| 461 | C$_2$H$_5$ | n-C$_5$H$_{11}$ |
| 462 | C$_2$H$_5$ | n-C$_6$H$_{13}$ |
| 463 | C$_2$H$_5$ | n-C$_7$H$_{15}$ |
| 464 | n-C$_3$H$_7$ | H |
| 465 | n-C$_3$H$_7$ | CH$_3$ |
| 466 | n-C$_3$H$_7$ | C$_2$H$_5$ |
| 467 | n-C$_3$H$_7$ | n-C$_4$H$_9$ |
| 468 | n-C$_3$H$_7$ | n-C$_5$H$_{11}$ |
| 469 | n-C$_3$H$_7$ | n-C$_6$H$_{13}$ |
| 470 | n-C$_3$H$_7$ | n-C$_7$H$_{15}$ |
| 471 | n-C$_4$H$_9$ | H |
| 472 | n-C$_4$H$_9$ | CH$_3$ |
| 473 | n-C$_4$H$_9$ | C$_2$H$_5$ |
| 474 | n-C$_4$H$_9$ | n-C$_3$H$_7$ |
| 475 | n-C$_4$H$_9$ | n-C$_4$H$_9$ |
| 476 | n-C$_4$H$_9$ | n-C$_5$H$_{11}$ |
| 477 | n-C$_4$H$_9$ | n-C$_6$H$_{13}$ |
| 478 | n-C$_4$H$_9$ | n-C$_7$H$_{15}$ |
| 479 | n-C$_5$H$_{11}$ | H |
| 480 | n-C$_5$H$_{11}$ | CH$_3$ |
| 481 | n-C$_5$H$_{11}$ | C$_2$H$_5$ |
| 482 | n-C$_5$H$_{11}$ | n-C$_3$H$_7$ |
| 483 | n-C$_5$H$_{11}$ | n-C$_4$H$_9$ |
| 484 | n-C$_5$H$_{11}$ | n-C$_5$H$_{11}$ |
| 485 | n-C$_5$H$_{11}$ | n-C$_6$H$_{13}$ |
| 486 | n-C$_5$H$_{11}$ | n-C$_7$H$_{15}$ |
| 487 | n-C$_6$H$_{13}$ | H |
| 488 | n-C$_6$H$_{13}$ | CH$_3$ |
| 489 | n-C$_6$H$_{13}$ | C$_2$H$_5$ |
| 490 | n-C$_6$H$_{13}$ | n-C$_3$H$_7$ |
| 491 | n-C$_6$H$_{13}$ | n-C$_4$H$_9$ |
| 492 | n-C$_6$H$_{13}$ | n-C$_5$H$_{11}$ |
| 493 | n-C$_6$H$_{13}$ | n-C$_6$H$_{13}$ |
| 494 | n-C$_6$H$_{13}$ | n-C$_7$H$_{15}$ |
| 495 | n-C$_7$H$_{15}$ | H |
| 496 | n-C$_7$H$_{15}$ | CH$_3$ |
| 497 | n-C$_7$H$_{15}$ | C$_2$H$_5$ |
| 498 | n-C$_7$H$_{15}$ | n-C$_3$H$_7$ |
| 499 | n-C$_7$H$_{15}$ | n-C$_4$H$_9$ |
| 500 | n-C$_7$H$_{15}$ | n-C$_5$H$_{11}$ |
| 501 | n-C$_7$H$_{15}$ | n-C$_6$H$_{13}$ |
| 502 | n-C$_7$H$_{15}$ | n-C$_7$H$_{15}$ |
| 503 | CH$_3$ | H |
| 504 | CH$_3$ | CH$_3$ |
| 505 | CH$_3$ | C$_2$H$_5$ |
| 506 | CH$_3$ | n-C$_3$H$_7$ |
| 507 | CH$_3$ | n-C$_4$H$_9$ |
| 508 | CH$_3$ | n-C$_5$H$_{11}$ |
| 509 | CH$_3$ | n-C$_6$H$_{13}$ |
| 510 | CH$_3$ | n-C$_7$H$_{15}$ |
| 511 | C$_2$H$_5$ | H |
| 512 | C$_2$H$_5$ | CH$_3$ |
| 513 | C$_2$H$_5$ | C$_2$H$_5$ |
| 514 | C$_2$H$_5$ | n-C$_3$H$_7$ |
| 515 | C$_2$H$_5$ | n-C$_4$H$_9$ |

TABLE 2-continued

| Ex. | R$^1$ | R$^2$ |
|---|---|---|
| 516 | C$_2$H$_5$ | n-C$_5$H$_{11}$ |
| 517 | C$_2$H$_5$ | n-C$_6$H$_{13}$ |
| 518 | C$_2$H$_5$ | n-C$_7$H$_{15}$ |
| 519 | n-C$_3$H$_7$ | H |
| 520 | n-C$_3$H$_7$ | CH$_3$ |
| 521 | n-C$_3$H$_7$ | C$_2$H$_5$ |
| 522 | n-C$_3$H$_7$ | n-C$_4$H$_9$ |
| 523 | n-C$_3$H$_7$ | n-C$_5$H$_{11}$ |
| 524 | n-C$_3$H$_7$ | n-C$_6$H$_{13}$ |
| 525 | n-C$_3$H$_7$ | n-C$_7$H$_{15}$ |
| 526 | n-C$_4$H$_9$ | H |
| 527 | n-C$_4$H$_9$ | CH$_3$ |
| 528 | n-C$_4$H$_9$ | C$_2$H$_5$ |
| 529 | n-C$_4$H$_9$ | n-C$_3$H$_7$ |
| 530 | n-C$_4$H$_9$ | n-C$_4$H$_9$ |
| 531 | n-C$_4$H$_9$ | n-C$_5$H$_{11}$ |
| 532 | n-C$_4$H$_9$ | n-C$_6$H$_{13}$ |
| 533 | n-C$_4$H$_9$ | n-C$_7$H$_{15}$ |
| 534 | n-C$_5$H$_{11}$ | H |
| 535 | n-C$_5$H$_{11}$ | CH$_3$ |
| 536 | n-C$_5$H$_{11}$ | C$_2$H$_5$ |
| 537 | n-C$_5$H$_{11}$ | n-C$_3$H$_7$ |
| 538 | n-C$_5$H$_{11}$ | n-C$_4$H$_9$ |
| 539 | n-C$_5$H$_{11}$ | n-C$_5$H$_{11}$ |
| 540 | n-C$_5$H$_{11}$ | n-C$_6$H$_{13}$ |
| 541 | n-C$_5$H$_{11}$ | n-C$_7$H$_{15}$ |
| 542 | n-C$_6$H$_{13}$ | H |
| 543 | n-C$_6$H$_{13}$ | CH$_3$ |
| 544 | n-C$_6$H$_{13}$ | C$_2$H$_5$ |
| 545 | n-C$_6$H$_{13}$ | n-C$_3$H$_7$ |
| 546 | n-C$_6$H$_{13}$ | n-C$_4$H$_9$ |
| 547 | n-C$_6$H$_{13}$ | n-C$_5$H$_{11}$ |
| 548 | n-C$_6$H$_{13}$ | n-C$_6$H$_{13}$ |
| 549 | n-C$_6$H$_{13}$ | n-C$_7$H$_{15}$ |
| 550 | n-C$_7$H$_{15}$ | H |
| 551 | n-C$_7$H$_{15}$ | CH$_3$ |
| 552 | n-C$_7$H$_{15}$ | C$_2$H$_5$ |
| 553 | n-C$_7$H$_{15}$ | n-C$_3$H$_7$ |
| 554 | n-C$_7$H$_{15}$ | n-C$_4$H$_9$ |
| 555 | n-C$_7$H$_{15}$ | n-C$_5$H$_{11}$ |
| 556 | n-C$_7$H$_{15}$ | n-C$_6$H$_{13}$ |
| 557 | n-C$_7$H$_{15}$ | n-C$_7$H$_{15}$ |
| 558 | CH$_3$ | H |
| 559 | CH$_3$ | CH$_3$ |
| 560 | CH$_3$ | C$_2$H$_5$ |
| 561 | CH$_3$ | n-C$_3$H$_7$ |
| 562 | CH$_3$ | n-C$_4$H$_9$ |
| 563 | CH$_3$ | n-C$_5$H$_{11}$ |
| 564 | CH$_3$ | n-C$_6$H$_{13}$ |
| 565 | CH$_3$ | n-C$_7$H$_{15}$ |
| 566 | C$_2$H$_5$ | H |
| 567 | C$_2$H$_5$ | CH$_3$ |
| 568 | C$_2$H$_5$ | C$_2$H$_5$ |
| 569 | C$_2$H$_5$ | n-C$_3$H$_7$ |
| 570 | C$_2$H$_5$ | n-C$_4$H$_9$ |
| 571 | C$_2$H$_5$ | n-C$_5$H$_{11}$ |
| 572 | C$_2$H$_5$ | n-C$_6$H$_{13}$ |
| 573 | C$_2$H$_5$ | n-C$_7$H$_{15}$ |
| 574 | n-C$_3$H$_7$ | H |
| 575 | n-C$_3$H$_7$ | CH$_3$ |
| 576 | n-C$_3$H$_7$ | C$_2$H$_5$ |
| 577 | n-C$_3$H$_7$ | n-C$_4$H$_9$ |
| 578 | n-C$_3$H$_7$ | n-C$_5$H$_{11}$ |
| 579 | n-C$_3$H$_7$ | n-C$_6$H$_{13}$ |
| 580 | n-C$_3$H$_7$ | n-C$_7$H$_{15}$ |
| 581 | n-C$_4$H$_9$ | H |
| 582 | n-C$_4$H$_9$ | CH$_3$ |
| 583 | n-C$_4$H$_9$ | C$_2$H$_5$ |
| 584 | n-C$_4$H$_9$ | n-C$_3$H$_7$ |
| 585 | n-C$_4$H$_9$ | n-C$_4$H$_9$ |
| 586 | n-C$_4$H$_9$ | n-C$_5$H$_{11}$ |
| 587 | n-C$_4$H$_9$ | n-C$_6$H$_{13}$ |
| 588 | n-C$_4$H$_9$ | n-C$_7$H$_{15}$ |
| 589 | n-C$_5$H$_{11}$ | H |
| 590 | n-C$_5$H$_{11}$ | CH$_3$ |
| 591 | n-C$_5$H$_{11}$ | C$_2$H$_5$ |
| 592 | n-C$_5$H$_{11}$ | n-C$_3$H$_7$ |
| 593 | n-C$_5$H$_{11}$ | n-C$_4$H$_9$ |
| 594 | n-C$_5$H$_{11}$ | n-C$_5$H$_{11}$ |
| 595 | n-C$_5$H$_{11}$ | n-C$_6$H$_{13}$ |
| 596 | n-C$_5$H$_{11}$ | n-C$_7$H$_{15}$ |
| 597 | n-C$_6$H$_{13}$ | H |
| 598 | n-C$_6$H$_{13}$ | CH$_3$ |
| 599 | n-C$_6$H$_{13}$ | C$_2$H$_5$ |
| 600 | n-C$_6$H$_{13}$ | n-C$_3$H$_7$ |
| 601 | n-C$_6$H$_{13}$ | n-C$_4$H$_9$ |
| 602 | n-C$_6$H$_{13}$ | n-C$_5$H$_{11}$ |
| 603 | n-C$_6$H$_{13}$ | n-C$_6$H$_{13}$ |
| 604 | n-C$_6$H$_{13}$ | n-C$_7$H$_{15}$ |
| 605 | n-C$_7$H$_{15}$ | H |
| 606 | n-C$_7$H$_{15}$ | CH$_3$ |
| 607 | n-C$_7$H$_{15}$ | C$_2$H$_5$ |
| 608 | n-C$_7$H$_{15}$ | n-C$_3$H$_7$ |
| 609 | n-C$_7$H$_{15}$ | n-C$_4$H$_9$ |
| 610 | n-C$_7$H$_{15}$ | n-C$_5$H$_{11}$ |
| 611 | n-C$_7$H$_{15}$ | n-C$_6$H$_{13}$ |
| 612 | n-C$_7$H$_{15}$ | n-C$_7$H$_{15}$ |
| 613 | CH$_3$ | H |
| 614 | CH$_3$ | CH$_3$ |
| 615 | CH$_3$ | C$_2$H$_5$ |
| 616 | CH$_3$ | n-C$_3$H$_7$ |
| 617 | CH$_3$ | n-C$_4$H$_9$ |
| 618 | CH$_3$ | n-C$_5$H$_{11}$ |
| 619 | CH$_3$ | n-C$_6$H$_{13}$ |
| 620 | CH$_3$ | n-C$_7$H$_{15}$ |
| 621 | C$_2$H$_5$ | H |
| 622 | C$_2$H$_5$ | CH$_3$ |
| 623 | C$_2$H$_5$ | C$_2$H$_5$ |
| 624 | C$_2$H$_5$ | n-C$_3$H$_7$ |
| 625 | C$_2$H$_5$ | n-C$_4$H$_9$ |
| 626 | C$_2$H$_5$ | n-C$_5$H$_{11}$ |
| 627 | C$_2$H$_5$ | n-C$_6$H$_{13}$ |
| 628 | C$_2$H$_5$ | n-C$_7$H$_{15}$ |
| 629 | n-C$_3$H$_7$ | H |
| 630 | n-C$_3$H$_7$ | CH$_3$ |
| 631 | n-C$_3$H$_7$ | C$_2$H$_5$ |
| 632 | n-C$_3$H$_7$ | n-C$_4$H$_9$ |
| 633 | n-C$_3$H$_7$ | n-C$_5$H$_{11}$ |
| 634 | n-C$_3$H$_7$ | n-C$_6$H$_{13}$ |
| 635 | n-C$_3$H$_7$ | n-C$_7$H$_{15}$ |
| 636 | n-C$_4$H$_9$ | H |
| 637 | n-C$_4$H$_9$ | CH$_3$ |
| 638 | n-C$_4$H$_9$ | C$_2$H$_5$ |
| 639 | n-C$_4$H$_9$ | n-C$_3$H$_7$ |
| 640 | n-C$_4$H$_9$ | n-C$_4$H$_9$ |
| 641 | n-C$_4$H$_9$ | n-C$_5$H$_{11}$ |
| 642 | n-C$_4$H$_9$ | n-C$_6$H$_{13}$ |
| 643 | n-C$_4$H$_9$ | n-C$_7$H$_{15}$ |
| 644 | n-C$_5$H$_{11}$ | H |
| 645 | n-C$_5$H$_{11}$ | CH$_3$ |
| 646 | n-C$_5$H$_{11}$ | C$_2$H$_5$ |
| 647 | n-C$_5$H$_{11}$ | n-C$_3$H$_7$ |
| 648 | n-C$_5$H$_{11}$ | n-C$_4$H$_9$ |
| 649 | n-C$_5$H$_{11}$ | n-C$_5$H$_{11}$ |
| 650 | n-C$_5$H$_{11}$ | n-C$_6$H$_{13}$ |
| 651 | n-C$_5$H$_{11}$ | n-C$_7$H$_{15}$ |

TABLE 2-continued

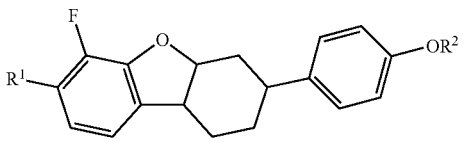

| Ex. | R¹ | R² |
|---|---|---|
| 652 | n-C$_6$H$_{13}$ | H |
| 653 | n-C$_6$H$_{13}$ | CH$_3$ |
| 654 | n-C$_6$H$_{13}$ | C$_2$H$_5$ |
| 655 | n-C$_6$H$_{13}$ | n-C$_3$H$_7$ |
| 656 | n-C$_6$H$_{13}$ | n-C$_4$H$_9$ |
| 657 | n-C$_6$H$_{13}$ | n-C$_5$H$_{11}$ |
| 658 | n-C$_6$H$_{13}$ | n-C$_6$H$_{13}$ |
| 659 | n-C$_6$H$_{13}$ | n-C$_7$H$_{15}$ |
| 660 | n-C$_7$H$_{15}$ | H |
| 661 | n-C$_7$H$_{15}$ | CH$_3$ |
| 662 | n-C$_7$H$_{15}$ | C$_2$H$_5$ |
| 663 | n-C$_7$H$_{15}$ | n-C$_3$H$_7$ |
| 664 | n-C$_7$H$_{15}$ | n-C$_4$H$_9$ |
| 665 | n-C$_7$H$_{15}$ | n-C$_5$H$_{11}$ |
| 666 | n-C$_7$H$_{15}$ | n-C$_6$H$_{13}$ |
| 667 | n-C$_7$H$_{15}$ | n-C$_7$H$_{15}$ |

Analogously to Example 2: Examples 668 to 715:

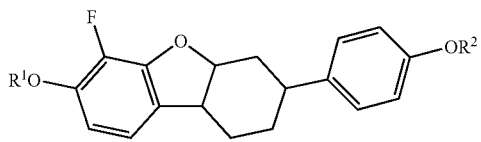

Analogously to Example 2: Examples 716 to 767:

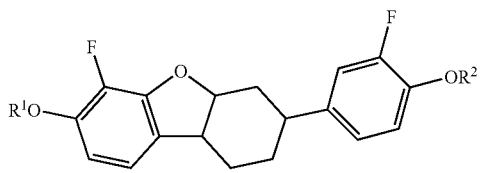

Analogously to Example 2: Examples 768 to 815:

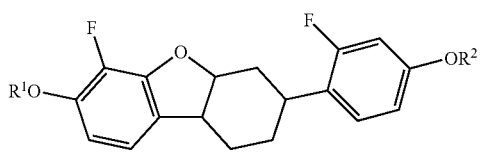

Analogously to Example 2: Examples 816 to 863:

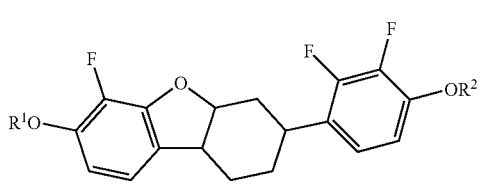

Analogously to Example 2: Examples 864 to 911:

![structure]

Analogously to Example 2: Examples 912 to 959:

TABLE 3

![structure]

| Ex. | R¹ | R² |
|---|---|---|
| 668 | CH$_3$ | CH$_3$ |
| 669 | CH$_3$ | C$_2$H$_5$ |
| 670 | CH$_3$ | n-C$_3$H$_7$ |
| 671 | CH$_3$ | n-C$_4$H$_9$ |
| 672 | CH$_3$ | n-C$_5$H$_{11}$ |
| 673 | CH$_3$ | n-C$_6$H$_{13}$ |
| 674 | CH$_3$ | n-C$_7$H$_{15}$ |
| 675 | C$_2$H$_5$ | CH$_3$ |
| 676 | C$_2$H$_5$ | C$_2$H$_5$ |
| 677 | C$_2$H$_5$ | n-C$_3$H$_7$ |
| 678 | C$_2$H$_5$ | n-C$_4$H$_9$ |
| 679 | C$_2$H$_5$ | n-C$_5$H$_{11}$ |
| 680 | C$_2$H$_5$ | n-C$_6$H$_{13}$ |
| 681 | C$_2$H$_5$ | n-C$_7$H$_{15}$ |
| 682 | n-C$_3$H$_7$ | CH$_3$ |
| 683 | n-C$_3$H$_7$ | C$_2$H$_5$ |
| 684 | n-C$_3$H$_7$ | n-C$_4$H$_9$ |
| 685 | n-C$_3$H$_7$ | n-C$_5$H$_{11}$ |
| 686 | n-C$_3$H$_7$ | n-C$_6$H$_{13}$ |
| 687 | n-C$_3$H$_7$ | n-C$_7$H$_{15}$ |
| 688 | n-C$_4$H$_9$ | CH$_3$ |
| 689 | n-C$_4$H$_9$ | C$_2$H$_5$ |
| 690 | n-C$_4$H$_9$ | n-C$_3$H$_7$ |
| 691 | n-C$_4$H$_9$ | n-C$_4$H$_9$ |
| 692 | n-C$_4$H$_9$ | n-C$_5$H$_{11}$ |
| 693 | n-C$_4$H$_9$ | n-C$_6$H$_{13}$ |
| 694 | n-C$_4$H$_9$ | n-C$_7$H$_{15}$ |
| 695 | n-C$_5$H$_{11}$ | CH$_3$ |
| 696 | n-C$_5$H$_{11}$ | C$_2$H$_5$ |
| 697 | n-C$_5$H$_{11}$ | n-C$_3$H$_7$ |
| 698 | n-C$_5$H$_{11}$ | n-C$_4$H$_9$ |
| 699 | n-C$_5$H$_{11}$ | n-C$_5$H$_{11}$ |
| 700 | n-C$_5$H$_{11}$ | n-C$_6$H$_{13}$ |
| 701 | n-C$_5$H$_{11}$ | n-C$_7$H$_{15}$ |
| 702 | n-C$_6$H$_{13}$ | CH$_3$ |
| 703 | n-C$_6$H$_{13}$ | C$_2$H$_5$ |
| 704 | n-C$_6$H$_{13}$ | n-C$_3$H$_7$ |
| 705 | n-C$_6$H$_{13}$ | n-C$_4$H$_9$ |
| 706 | n-C$_6$H$_{13}$ | n-C$_5$H$_{11}$ |
| 707 | n-C$_6$H$_{13}$ | n-C$_6$H$_{13}$ |
| 708 | n-C$_6$H$_{13}$ | n-C$_7$H$_{15}$ |
| 709 | n-C$_7$H$_{15}$ | CH$_3$ |
| 710 | n-C$_7$H$_{15}$ | C$_2$H$_5$ |
| 711 | n-C$_7$H$_{15}$ | n-C$_3$H$_7$ |
| 712 | n-C$_7$H$_{15}$ | n-C$_4$H$_9$ |
| 713 | n-C$_7$H$_{15}$ | n-C$_5$H$_{11}$ |
| 714 | n-C$_7$H$_{15}$ | n-C$_6$H$_{13}$ |
| 715 | n-C$_7$H$_{15}$ | n-C$_7$H$_{15}$ |
| 716 | CH$_3$ | CH$_3$ |
| 717 | CH$_3$ | C$_2$H$_5$ |
| 718 | CH$_3$ | n-C$_3$H$_7$ |
| 719 | CH$_3$ | n-C$_4$H$_9$ |
| 720 | CH$_3$ | n-C$_5$H$_{11}$ |
| 721 | CH$_3$ | n-C$_6$H$_{13}$ |
| 722 | CH$_3$ | n-C$_7$H$_{15}$ |

TABLE 3-continued

![Structure with R¹ and OR² substituents on fluorinated dibenzofuran]

| Ex. | R¹ | R² |
|---|---|---|
| 723 | C₂H₅ | CH₃ |
| 724 | C₂H₅ | C₂H₅ |
| 725 | C₂H₅ | n-C₃H₇ |
| 726 | C₂H₅ | n-C₄H₉ |
| 727 | C₂H₅ | n-C₅H₁₁ |
| 728 | C₂H₅ | n-C₆H₁₃ |
| 729 | C₂H₅ | n-C₇H₁₅ |
| 730 | n-C₃H₇ | CH₃ |
| 731 | n-C₃H₇ | C₂H₅ |
| 732 | n-C₃H₇ | n-C₄H₉ |
| 733 | n-C₃H₇ | n-C₅H₁₁ |
| 734 | n-C₃H₇ | n-C₆H₁₃ |
| 735 | n-C₃H₇ | n-C₇H₁₅ |
| 736 | n-C₄H₉ | CH₃ |
| 737 | n-C₄H₉ | C₂H₅ |
| 738 | n-C₄H₉ | n-C₃H₇ |
| 739 | n-C₄H₉ | n-C₄H₉ |
| 740 | n-C₄H₉ | n-C₅H₁₁ |
| 741 | n-C₄H₉ | n-C₆H₁₃ |
| 742 | n-C₄H₉ | n-C₇H₁₅ |
| 743 | n-C₅H₁₁ | CH₃ |
| 744 | n-C₅H₁₁ | C₂H₅ |
| 745 | n-C₅H₁₁ | n-C₃H₇ |
| 746 | n-C₅H₁₁ | n-C₄H₉ |
| 747 | n-C₅H₁₁ | n-C₅H₁₁ |
| 748 | n-C₅H₁₁ | n-C₆H₁₃ |
| 749 | n-C₅H₁₁ | n-C₇H₁₅ |
| 750 | n-C₆H₁₃ | CH₃ |
| 751 | n-C₆H₁₃ | C₂H₅ |
| 752 | n-C₆H₁₃ | n-C₃H₇ |
| 753 | n-C₆H₁₃ | n-C₄H₉ |
| 754 | n-C₆H₁₃ | n-C₅H₁₁ |
| 755 | n-C₆H₁₃ | n-C₆H₁₃ |
| 756 | n-C₆H₁₃ | n-C₇H₁₅ |
| 757 | n-C₇H₁₅ | CH₃ |
| 758 | n-C₇H₁₅ | C₂H₅ |
| 759 | n-C₇H₁₅ | n-C₃H₇ |
| 760 | n-C₇H₁₅ | n-C₄H₉ |
| 761 | n-C₇H₁₅ | n-C₅H₁₁ |
| 762 | n-C₇H₁₅ | n-C₆H₁₃ |
| 763 | n-C₇H₁₅ | n-C₇H₁₅ |
| 768 | CH₃ | CH₃ |
| 769 | CH₃ | C₂H₅ |
| 770 | CH₃ | n-C₃H₇ |
| 771 | CH₃ | n-C₄H₉ |
| 772 | CH₃ | n-C₅H₁₁ |
| 773 | CH₃ | n-C₆H₁₃ |
| 774 | CH₃ | n-C₇H₁₅ |
| 775 | C₂H₅ | CH₃ |
| 776 | C₂H₅ | C₂H₅ |
| 777 | C₂H₅ | n-C₃H₇ |
| 778 | C₂H₅ | n-C₄H₉ |
| 779 | C₂H₅ | n-C₅H₁₁ |
| 780 | C₂H₅ | n-C₆H₁₃ |
| 781 | C₂H₅ | n-C₇H₁₅ |
| 782 | n-C₃H₇ | CH₃ |
| 783 | n-C₃H₇ | C₂H₅ |
| 784 | n-C₃H₇ | n-C₄H₉ |
| 785 | n-C₃H₇ | n-C₅H₁₁ |
| 786 | n-C₃H₇ | n-C₆H₁₃ |
| 787 | n-C₃H₇ | n-C₇H₁₅ |
| 788 | n-C₄H₉ | CH₃ |
| 789 | n-C₄H₉ | C₂H₅ |
| 790 | n-C₄H₉ | n-C₃H₇ |
| 791 | n-C₄H₉ | n-C₄H₉ |
| 792 | n-C₄H₉ | n-C₅H₁₁ |
| 793 | n-C₄H₉ | n-C₆H₁₃ |
| 794 | n-C₄H₉ | n-C₇H₁₅ |
| 795 | n-C₅H₁₁ | CH₃ |
| 796 | n-C₅H₁₁ | C₂H₅ |
| 797 | n-C₅H₁₁ | n-C₃H₇ |
| 798 | n-C₅H₁₁ | n-C₄H₉ |
| 799 | n-C₅H₁₁ | n-C₅H₁₁ |
| 800 | n-C₅H₁₁ | n-C₆H₁₃ |
| 801 | n-C₅H₁₁ | n-C₇H₁₅ |
| 802 | n-C₆H₁₃ | CH₃ |
| 803 | n-C₆H₁₃ | C₂H₅ |
| 804 | n-C₆H₁₃ | n-C₃H₇ |
| 805 | n-C₆H₁₃ | n-C₄H₉ |
| 806 | n-C₆H₁₃ | n-C₅H₁₁ |
| 807 | n-C₆H₁₃ | n-C₆H₁₃ |
| 808 | n-C₆H₁₃ | n-C₇H₁₅ |
| 809 | n-C₇H₁₅ | CH₃ |
| 810 | n-C₇H₁₅ | C₂H₅ |
| 811 | n-C₇H₁₅ | n-C₃H₇ |
| 812 | n-C₇H₁₅ | n-C₄H₉ |
| 813 | n-C₇H₁₅ | n-C₅H₁₁ |
| 814 | n-C₇H₁₅ | n-C₆H₁₃ |
| 815 | n-C₇H₁₅ | n-C₇H₁₅ |
| 816 | CH₃ | CH₃ |
| 817 | CH₃ | C₂H₅ |
| 818 | CH₃ | n-C₃H₇ |
| 819 | CH₃ | n-C₄H₉ |
| 820 | CH₃ | n-C₅H₁₁ |
| 821 | CH₃ | n-C₆H₁₃ |
| 822 | CH₃ | n-C₇H₁₅ |
| 823 | C₂H₅ | CH₃ |
| 824 | C₂H₅ | C₂H₅ |
| 825 | C₂H₅ | n-C₃H₇ |
| 826 | C₂H₅ | n-C₄H₉ |
| 827 | C₂H₅ | n-C₅H₁₁ |
| 828 | C₂H₅ | n-C₆H₁₃ |
| 829 | C₂H₄ | n-C₇H₁₅ |
| 830 | n-C₃H₇ | CH₃ |
| 831 | n-C₃H₇ | C₂H₅ |
| 832 | n-C₃H₇ | n-C₄H₉ |
| 833 | n-C₃H₇ | n-C₅H₁₁ |
| 834 | n-C₃H₇ | n-C₆H₁₃ |
| 835 | n-C₃H₇ | n-C₇H₁₅ |
| 836 | n-C₄H₉ | CH₃ |
| 837 | n-C₄H₉ | C₂H₅ |
| 838 | n-C₄H₉ | n-C₃H₇ |
| 839 | n-C₄H₉ | n-C₄H₉ |
| 840 | n-C₄H₉ | n-C₅H₁₁ |
| 841 | n-C₄H₉ | n-C₆H₁₃ |
| 842 | n-C₄H₉ | n-C₇H₁₅ |
| 843 | n-C₅H₁₁ | CH₃ |
| 844 | n-C₅H₁₁ | C₂H₅ |
| 845 | n-C₅H₁₁ | n-C₃H₇ |
| 846 | n-C₅H₁₁ | n-C₄H₉ |
| 847 | n-C₅H₁₁ | n-C₅H₁₁ |
| 848 | n-C₅H₁₁ | n-C₆H₁₃ |
| 849 | n-C₅H₁₁ | n-C₇H₁₅ |
| 850 | n-C₆H₁₃ | CH₃ |
| 851 | n-C₆H₁₃ | C₂H₅ |
| 852 | n-C₆H₁₃ | n-C₃H₇ |
| 853 | n-C₆H₁₃ | n-C₄H₉ |
| 854 | n-C₆H₁₃ | n-C₅H₁₁ |
| 855 | n-C₆H₁₃ | n-C₆H₁₃ |
| 856 | n-C₆H₁₃ | n-C₇H₁₅ |
| 857 | n-C₇H₁₅ | CH₃ |
| 858 | n-C₇H₁₅ | C₂H₅ |
| 859 | n-C₇H₁₅ | n-C₃H₇ |
| 860 | n-C₇H₁₅ | n-C₄H₉ |
| 861 | n-C₇H₁₅ | n-C₅H₁₁ |
| 862 | n-C₇H₁₅ | n-C₆H₁₃ |

TABLE 3-continued

![structure with R1, OR2, F groups on dibenzofuran]

| Ex. | R¹ | R² |
|---|---|---|
| 863 | n-C₇H₁₅ | n-C₇H₁₅ |
| 864 | CH₃ | CH₃ |
| 865 | CH₃ | C₂H₅ |
| 866 | CH₃ | n-C₃H₇ |
| 867 | CH₃ | n-C₄H₉ |
| 868 | CH₃ | n-C₅H₁₁ |
| 869 | CH₃ | n-C₆H₁₃ |
| 870 | CH₃ | n-C₇H₁₅ |
| 871 | C₂H₅ | CH₃ |
| 872 | C₂H₅ | C₂H₅ |
| 873 | C₂H₅ | n-C₃H₇ |
| 874 | C₂H₅ | n-C₄H₉ |
| 875 | C₂H₅ | n-C₅H₁₁ |
| 876 | C₂H₅ | n-C₆H₁₃ |
| 877 | C₂H₅ | n-C₇H₁₅ |
| 878 | n-C₃H₇ | CH₃ |
| 879 | n-C₃H₇ | C₂H₅ |
| 880 | n-C₃H₇ | n-C₄H₉ |
| 881 | n-C₃H₇ | n-C₅H₁₁ |
| 882 | n-C₃H₇ | n-C₆H₁₃ |
| 883 | n-C₃H₇ | n-C₇H₁₅ |
| 884 | n-C₄H₉ | CH₃ |
| 885 | n-C₄H₉ | C₂H₅ |
| 886 | n-C₄H₉ | n-C₃H₇ |
| 887 | n-C₄H₉ | n-C₄H₉ |
| 888 | n-C₄H₉ | n-C₅H₁₁ |
| 889 | n-C₄H₉ | n-C₆H₁₃ |
| 890 | n-C₄H₉ | n-C₇H₁₅ |
| 891 | n-C₅H₁₁ | CH₃ |
| 892 | n-C₅H₁₁ | C₂H₅ |
| 893 | n-C₅H₁₁ | n-C₃H₇ |
| 894 | n-C₅H₁₁ | n-C₄H₉ |
| 895 | n-C₅H₁₁ | n-C₅H₁₁ |
| 896 | n-C₅H₁₁ | n-C₆H₁₃ |
| 897 | n-C₅H₁₁ | n-C₇H₁₅ |
| 898 | n-C₆H₁₃ | CH₃ |
| 899 | n-C₆H₁₃ | C₂H₅ |
| 900 | n-C₆H₁₃ | n-C₃H₇ |
| 901 | n-C₆H₁₃ | n-C₄H₉ |
| 902 | n-C₆H₁₃ | n-C₅H₁₁ |
| 903 | n-C₆H₁₃ | n-C₆H₁₃ |
| 904 | n-C₆H₁₃ | n-C₇H₁₅ |
| 905 | n-C₇H₁₅ | CH₃ |
| 906 | n-C₇H₁₅ | C₂H₅ |
| 907 | n-C₇H₁₅ | n-C₃H₇ |
| 908 | n-C₇H₁₅ | n-C₄H₉ |
| 909 | n-C₇H₁₅ | n-C₅H₁₁ |
| 910 | n-C₇H₁₅ | n-C₆H₁₃ |
| 911 | n-C₇H₁₅ | n-C₇H₁₅ |
| 912 | CH₃ | CH₃ |
| 913 | CH₃ | C₂H₅ |
| 914 | CH₃ | n-C₃H₇ |
| 915 | CH₃ | n-C₄H₉ |
| 916 | CH₃ | n-C₅H₁₁ |
| 917 | CH₃ | n-C₆H₁₃ |
| 918 | CH₃ | n-C₇H₁₅ |
| 919 | C₂H₅ | CH₃ |
| 920 | C₂H₅ | C₂H₅ |
| 921 | C₂H₅ | n-C₃H₇ |
| 922 | C₂H₅ | n-C₄H₉ |
| 923 | C₂H₅ | n-C₅H₁₁ |
| 924 | C₂H₅ | n-C₆H₁₃ |
| 925 | C₂H₅ | n-C₇H₁₅ |
| 926 | n-C₃H₇ | CH₃ |
| 927 | n-C₃H₇ | C₂H₅ |
| 928 | n-C₃H₇ | n-C₄H₉ |
| 929 | n-C₃H₇ | n-C₅H₁₁ |
| 930 | n-C₃H₇ | n-C₆H₁₃ |

TABLE 3-continued

![structure with R1, OR2, F groups on dibenzofuran]

| Ex. | R¹ | R² |
|---|---|---|
| 931 | n-C₃H₇ | n-C₇H₁₅ |
| 932 | n-C₄H₉ | CH₃ |
| 933 | n-C₄H₉ | C₂H₅ |
| 934 | n-C₄H₉ | n-C₃H₇ |
| 935 | n-C₄H₉ | n-C₄H₉ |
| 936 | n-C₄H₉ | n-C₅H₁₁ |
| 937 | n-C₄H₉ | n-C₆H₁₃ |
| 938 | n-C₄H₉ | n-C₇H₁₅ |
| 939 | n-C₅H₁₁ | CH₃ |
| 940 | n-C₅H₁₁ | C₂H₅ |
| 941 | n-C₅H₁₁ | n-C₃H₇ |
| 942 | n-C₅H₁₁ | n-C₄H₉ |
| 943 | n-C₅H₁₁ | n-C₅H₁₁ |
| 944 | n-C₅H₁₁ | n-C₆H₁₃ |
| 945 | n-C₅H₁₁ | n-C₇H₁₅ |
| 946 | n-C₆H₁₃ | CH₃ |
| 947 | n-C₆H₁₃ | C₂H₅ |
| 948 | n-C₆H₁₃ | n-C₃H₇ |
| 949 | n-C₆H₁₃ | n-C₄H₉ |
| 950 | n-C₆H₁₃ | n-C₅H₁₁ |
| 951 | n-C₆H₁₃ | n-C₆H₁₃ |
| 952 | n-C₆H₁₃ | n-C₇H₁₅ |
| 953 | n-C₇H₁₅ | CH₃ |
| 954 | n-C₇H₁₅ | C₂H₅ |
| 955 | n-C₇H₁₅ | n-C₃H₇ |
| 956 | n-C₇H₁₅ | n-C₄H₉ |
| 957 | n-C₇H₁₅ | n-C₅H₁₁ |
| 958 | n-C₇H₁₅ | n-C₆H₁₃ |
| 959 | n-C₇H₁₅ | n-C₇H₁₅ |

Analogously to Example 6: Examples 960 to 1014:

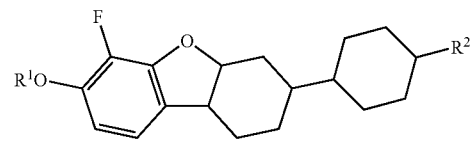

Analogously to Example 6: Examples 1015 to 1069:

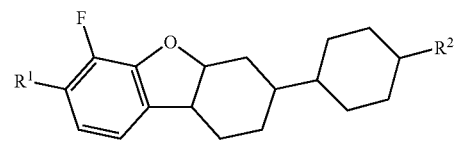

Analogously to Example 7: Examples 1070 to 1124:

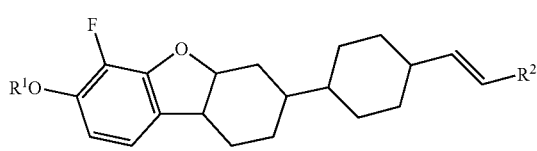

Analogously to Example 7: Examples 1125 to 1179:

TABLE 4

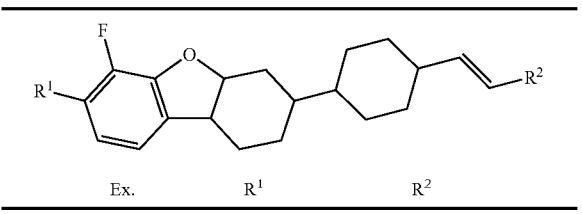

| Ex. | $R^1$ | $R^2$ |
|---|---|---|
| 960 | $CH_3$ | H |
| 961 | $CH_3$ | $CH_3$ |
| 962 | $CH_3$ | $C_2H_5$ |
| 963 | $CH_3$ | $n-C_3H_7$ |
| 964 | $CH_3$ | $n-C_4H_9$ |
| 965 | $CH_3$ | $n-C_5H_{11}$ |
| 966 | $CH_3$ | $n-C_6H_{13}$ |
| 967 | $CH_3$ | $n-C_7H_{15}$ |
| 968 | $C_2H_5$ | H |
| 969 | $C_2H_5$ | $CH_3$ |
| 970 | $C_2H_5$ | $C_2H_5$ |
| 971 | $C_2H_5$ | $n-C_3H_7$ |
| 972 | $C_2H_5$ | $n-C_4H_9$ |
| 973 | $C_2H_5$ | $n-C_5H_{11}$ |
| 974 | $C_2H_5$ | $n-C_6H_{13}$ |
| 975 | $C_2H_5$ | $n-C_7H_{15}$ |
| 976 | $n-C_3H_7$ | H |
| 977 | $n-C_3H_7$ | $CH_3$ |
| 978 | $n-C_3H_7$ | $C_2H_5$ |
| 979 | $n-C_3H_7$ | $n-C_4H_9$ |
| 980 | $n-C_3H_7$ | $n-C_5H_{11}$ |
| 981 | $n-C_3H_7$ | $n-C_6H_{13}$ |
| 982 | $n-C_3H_7$ | $n-C_7H_{15}$ |
| 983 | $n-C_4H_9$ | H |
| 984 | $n-C_4H_9$ | $CH_3$ |
| 985 | $n-C_4H_9$ | $C_2H_5$ |
| 986 | $n-C_4H_9$ | $n-C_3H_7$ |
| 987 | $n-C_4H_9$ | $n-C_4H_9$ |
| 988 | $n-C_4H_9$ | $n-C_5H_{11}$ |
| 989 | $n-C_4H_9$ | $n-C_6H_{13}$ |
| 990 | $n-C_4H_9$ | $n-C_7H_{15}$ |
| 991 | $n-C_5H_{11}$ | H |
| 992 | $n-C_5H_{11}$ | $CH_3$ |
| 993 | $n-C_5H_{11}$ | $C_2H_5$ |
| 994 | $n-C_5H_{11}$ | $n-C_3H_7$ |
| 995 | $n-C_5H_{11}$ | $n-C_4H_9$ |
| 996 | $n-C_5H_{11}$ | $n-C_5H_{11}$ |
| 997 | $n-C_5H_{11}$ | $n-C_6H_{13}$ |
| 998 | $n-C_5H_{11}$ | $n-C_7H_{15}$ |
| 999 | $n-C_6H_{13}$ | H |
| 1000 | $n-C_6H_{13}$ | $CH_3$ |
| 1001 | $n-C_6H_{13}$ | $C_2H_5$ |
| 1002 | $n-C_6H_{13}$ | $n-C_3H_7$ |
| 1003 | $n-C_6H_{13}$ | $n-C_4H_9$ |
| 1004 | $n-C_6H_{13}$ | $n-C_5H_{11}$ |
| 1005 | $n-C_6H_{13}$ | $n-C_6H_{13}$ |
| 1006 | $n-C_6H_{13}$ | $n-C_7H_{15}$ |
| 1007 | $n-C_7H_{15}$ | H |
| 1008 | $n-C_7H_{15}$ | $CH_3$ |
| 1009 | $n-C_7H_{15}$ | $C_2H_5$ |
| 1010 | $n-C_7H_{15}$ | $n-C_3H_7$ |
| 1011 | $n-C_7H_{15}$ | $n-C_4H_9$ |
| 1012 | $n-C_7H_{15}$ | $n-C_5H_{11}$ |
| 1013 | $n-C_7H_{15}$ | $n-C_6H_{13}$ |
| 1014 | $n-C_7H_{15}$ | $n-C_7H_{15}$ |
| 1015 | $CH_3$ | H |
| 1016 | $CH_3$ | $CH_3$ |
| 1017 | $CH_3$ | $C_2H_5$ |
| 1018 | $CH_3$ | $n-C_3H_7$ |
| 1019 | $CH_3$ | $n-C_4H_9$ |
| 1020 | $CH_3$ | $n-C_5H_{11}$ |
| 1021 | $CH_3$ | $n-C_6H_{13}$ |
| 1022 | $CH_3$ | $n-C_7H_{15}$ |
| 1023 | $C_2H_5$ | H |
| 1024 | $C_2H_5$ | $CH_3$ |
| 1025 | $C_2H_5$ | $C_2H_5$ |
| 1026 | $C_2H_5$ | $n-C_3H_7$ |
| 1027 | $C_2H_5$ | $n-C_4H_9$ |
| 1028 | $C_2H_5$ | $n-C_5H_{11}$ |
| 1029 | $C_2H_5$ | $n-C_6H_{13}$ |
| 1030 | $C_2H_5$ | $n-C_7H_{15}$ |
| 1031 | $n-C_3H_7$ | H |
| 1032 | $n-C_3H_7$ | $CH_3$ |
| 1033 | $n-C_3H_7$ | $C_2H_5$ |
| 1034 | $n-C_3H_7$ | $n-C_4H_9$ |
| 1035 | $n-C_3H_7$ | $n-C_5H_{11}$ |
| 1036 | $n-C_3H_7$ | $n-C_6H_{13}$ |
| 1037 | $n-C_3H_7$ | $n-C_7H_{15}$ |
| 1038 | $n-C_4H_9$ | H |
| 1039 | $n-C_4H_9$ | $CH_3$ |
| 1040 | $n-C_4H_9$ | $C_2H_5$ |
| 1041 | $n-C_4H_9$ | $n-C_3H_7$ |
| 1042 | $n-C_4H_9$ | $n-C_4H_9$ |
| 1043 | $n-C_4H_9$ | $n-C_5H_{11}$ |
| 1044 | $n-C_4H_9$ | $n-C_6H_{13}$ |
| 1045 | $n-C_4H_9$ | $n-C_7H_{15}$ |
| 1046 | $n-C_5H_{11}$ | H |
| 1047 | $n-C_5H_{11}$ | $CH_3$ |
| 1048 | $n-C_5H_{11}$ | $C_2H_5$ |
| 1049 | $n-C_5H_{11}$ | $n-C_3H_7$ |
| 1050 | $n-C_5H_{11}$ | $n-C_4H_9$ |
| 1051 | $n-C_5H_{11}$ | $n-C_5H_{11}$ |
| 1052 | $n-C_5H_{11}$ | $n-C_6H_{13}$ |
| 1053 | $n-C_5H_{11}$ | $n-C_7H_{15}$ |
| 1054 | $n-C_6H_{13}$ | H |
| 1055 | $n-C_6H_{13}$ | $CH_3$ |
| 1056 | $n-C_6H_{13}$ | $C_2H_5$ |
| 1057 | $n-C_6H_{13}$ | $n-C_3H_7$ |
| 1058 | $n-C_6H_{13}$ | $n-C_4H_9$ |
| 1059 | $n-C_6H_{13}$ | $n-C_5H_{11}$ |
| 1060 | $n-C_6H_{13}$ | $n-C_6H_{13}$ |
| 1061 | $n-C_6H_{13}$ | $n-C_7H_{15}$ |
| 1062 | $n-C_7H_{15}$ | H |
| 1063 | $n-C_7H_{15}$ | $CH_3$ |
| 1064 | $n-C_7H_{15}$ | $C_2H_5$ |
| 1065 | $n-C_7H_{15}$ | $n-C_3H_7$ |
| 1066 | $n-C_7H_{15}$ | $n-C_4H_9$ |
| 1067 | $n-C_7H_{15}$ | $n-C_5H_{11}$ |
| 1068 | $n-C_7H_{15}$ | $n-C_6H_{13}$ |
| 1069 | $n-C_7H_{15}$ | $n-C_7H_{15}$ |
| 1070 | $CH_3$ | H |
| 1071 | $CH_3$ | $CH_3$ |
| 1072 | $CH_3$ | $C_2H_5$ |
| 1073 | $CH_3$ | $n-C_3H_7$ |
| 1074 | $CH_3$ | $n-C_4H_9$ |
| 1075 | $CH_3$ | $n-C_5H_{11}$ |
| 1076 | $CH_3$ | $n-C_6H_{13}$ |
| 1077 | $CH_3$ | $n-C_7H_{15}$ |
| 1078 | $C_2H_5$ | H |
| 1079 | $C_2H_5$ | $CH_3$ |
| 1080 | $C_2H_5$ | $C_2H_5$ |
| 1081 | $C_2H_5$ | $n-C_3H_7$ |
| 1082 | $C_2H_5$ | $n-C_4H_9$ |
| 1083 | $C_2H_5$ | $n-C_5H_{11}$ |
| 1084 | $C_2H_5$ | $n-C_6H_{13}$ |
| 1085 | $C_2H_5$ | $n-C_7H_{15}$ |
| 1086 | $n-C_3H_7$ | H |
| 1087 | $n-C_3H_7$ | $CH_3$ |
| 1088 | $n-C_3H_7$ | $C_2H_5$ |
| 1089 | $n-C_3H_7$ | $n-C_4H_9$ |
| 1090 | $n-C_3H_7$ | $n-C_5H_{11}$ |
| 1091 | $n-C_3H_7$ | $n-C_6H_{13}$ |
| 1092 | $n-C_3H_7$ | $n-C_7H_{15}$ |
| 1093 | $n-C_4H_9$ | H |
| 1094 | $n-C_4H_9$ | $CH_3$ |
| 1095 | $n-C_4H_9$ | $C_2H_5$ |
| 1096 | $n-C_4H_9$ | $n-C_3H_7$ |

TABLE 4-continued

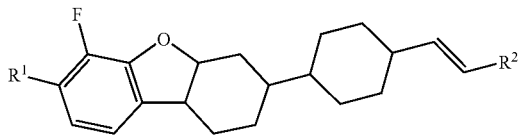

| Ex. | R¹ | R² |
|---|---|---|
| 1097 | n-C₄H₉ | n-C₄H₉ |
| 1098 | n-C₄H₉ | n-C₅H₁₁ |
| 1099 | n-C₄H₉ | n-C₆H₁₃ |
| 1100 | n-C₄H₉ | n-C₇H₁₅ |
| 1101 | n-C₅H₁₁ | H |
| 1102 | n-C₅H₁₁ | CH₃ |
| 1103 | n-C₅H₁₁ | C₂H₅ |
| 1104 | n-C₅H₁₁ | n-C₃H₇ |
| 1105 | n-C₅H₁₁ | n-C₄H₉ |
| 1106 | n-C₅H₁₁ | n-C₅H₁₁ |
| 1107 | n-C₅H₁₁ | n-C₆H₁₃ |
| 1108 | n-C₅H₁₁ | n-C₇H₁₅ |
| 1109 | n-C₆H₁₃ | H |
| 1110 | n-C₆H₁₃ | CH₃ |
| 1111 | n-C₆H₁₃ | C₂H₅ |
| 1112 | n-C₆H₁₃ | n-C₃H₇ |
| 1113 | n-C₆H₁₃ | n-C₄H₉ |
| 1114 | n-C₆H₁₃ | n-C₅H₁₁ |
| 1115 | n-C₆H₁₃ | n-C₆H₁₃ |
| 1116 | n-C₆H₁₃ | n-C₇H₁₅ |
| 1117 | n-C₇H₁₅ | H |
| 1118 | n-C₇H₁₅ | CH₃ |
| 1119 | n-C₇H₁₅ | C₂H₅ |
| 1120 | n-C₇H₁₅ | n-C₃H₇ |
| 1121 | n-C₇H₁₅ | n-C₄H₉ |
| 1122 | n-C₇H₁₅ | n-C₅H₁₁ |
| 1123 | n-C₇H₁₅ | n-C₆H₁₃ |
| 1124 | n-C₇H₁₅ | n-C₇H₁₅ |
| 1125 | CH₃ | H |
| 1126 | CH₃ | CH₃ |
| 1127 | CH₃ | C₂H₅ |
| 1128 | CH₃ | n-C₃H₇ |
| 1129 | CH₃ | n-C₄H₉ |
| 1130 | CH₃ | n-C₅H₁₁ |
| 1131 | CH₃ | n-C₆H₁₃ |
| 1132 | CH₃ | n-C₇H₁₅ |
| 1133 | C₂H₅ | H |
| 1134 | C₂H₅ | CH₃ |
| 1135 | C₂H₅ | C₂H₅ |
| 1136 | C₂H₅ | n-C₃H₇ |
| 1137 | C₂H₅ | n-C₄H₉ |
| 1138 | C₂H₅ | n-C₅H₁₁ |
| 1139 | C₂H₅ | n-C₆H₁₃ |
| 1140 | C₂H₅ | n-C₇H₁₅ |
| 1141 | n-C₃H₇ | H |
| 1142 | n-C₃H₇ | CH₃ |
| 1143 | n-C₃H₇ | C₂H₅ |
| 1144 | n-C₃H₇ | n-C₄H₉ |
| 1145 | n-C₃H₇ | n-C₅H₁₁ |
| 1146 | n-C₃H₇ | n-C₆H₁₃ |
| 1147 | n-C₃H₇ | n-C₇H₁₅ |
| 1148 | n-C₄H₉ | H |
| 1149 | n-C₄H₉ | CH₃ |
| 1150 | n-C₄H₉ | C₂H₅ |
| 1151 | n-C₄H₉ | n-C₃H₇ |
| 1152 | n-C₄H₉ | n-C₄H₉ |
| 1153 | n-C₄H₉ | n-C₅H₁₁ |
| 1154 | n-C₄H₉ | n-C₆H₁₃ |
| 1155 | n-C₄H₉ | n-C₇H₁₅ |
| 1156 | n-C₅H₁₁ | H |
| 1157 | n-C₅H₁₁ | CH₃ |
| 1158 | n-C₅H₁₁ | C₂H₅ |
| 1159 | n-C₅H₁₁ | n-C₃H₇ |
| 1160 | n-C₅H₁₁ | n-C₄H₉ |
| 1161 | n-C₅H₁₁ | n-C₅H₁₁ |
| 1162 | n-C₅H₁₁ | n-C₆H₁₃ |
| 1163 | n-C₅H₁₁ | n-C₇H₁₅ |
| 1164 | n-C₆H₁₃ | H |
| 1165 | n-C₆H₁₃ | CH₃ |

TABLE 4-continued

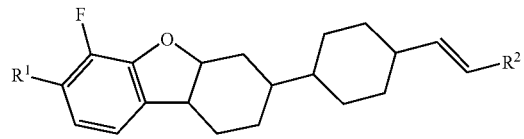

| Ex. | R¹ | R² |
|---|---|---|
| 1166 | n-C₆H₁₃ | C₂H₅ |
| 1167 | n-C₆H₁₃ | n-C₃H₇ |
| 1168 | n-C₆H₁₃ | n-C₄H₉ |
| 1169 | n-C₆H₁₃ | n-C₅H₁₁ |
| 1170 | n-C₆H₁₃ | n-C₆H₁₃ |
| 1171 | n-C₆H₁₃ | n-C₇H₁₅ |
| 1172 | n-C₇H₁₅ | H |
| 1173 | n-C₇H₁₅ | CH₃ |
| 1174 | n-C₇H₁₅ | C₂H₅ |
| 1175 | n-C₇H₁₅ | n-C₃H₇ |
| 1176 | n-C₇H₁₅ | n-C₄H₉ |
| 1177 | n-C₇H₁₅ | n-C₅H₁₁ |
| 1178 | n-C₇H₁₅ | n-C₆H₁₃ |
| 1179 | n-C₇H₁₅ | n-C₇H₁₅ |

Values for individual compounds from all of Tables 1-4:

TABLE 5

| Example No. | Δε | Δn | γ1 | Phase sequence |
|---|---|---|---|---|
| 34 | −5.1 | 0.088 | 132 | C 114 I |
| 36 | −5.0 | 0.090 | 171 | C 116 I |
| 99 | −1.4 | 0.060 | 130 | C 97 I |
| 141 | −5.4 | 0.098 | 102 | C 120 I |
| 142 | −5.4 | 0.094 | 149 | C 124 I |
| 144 | −4.8 | 0.100 | 164 | C 125 I |
| 204 | −1.9 | 0.062 | 59 | C 78 I |

The entire disclosure[s] of all applications, patents and publications, cited herein and of corresponding DE 10 2006 019 045.9, filed Apr. 25, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I:

I

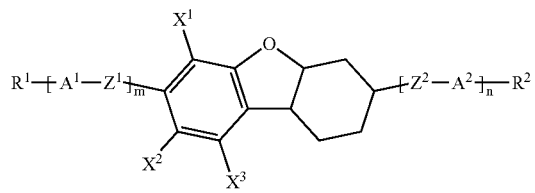

in which m and n each, independently of one another, are 0, 1 or 2, $X^1$, $X^2$ and $X^3$ each, independently of one another, denote H, halogen, CN or $CF_3$, $A^1$ and $A^2$ each, independently of one another, denote 1,4-phenylene, in which =CH— may be replaced once or twice by =N— and which may be unsubstituted or mono-to tetrasubstituted, independently of one another, by —CN, —F, —Cl, —Br, —I, unsubstituted or mono- or polyfluorine- and/or -chlorine-substituted $C_1$-$C_6$-alkanyl, unsubstituted or mono- or polyfluorine- and/or -chlorine-substituted $C_1$-$C_6$-alkoxy, 1,4-cyclohexylene, 1,4-cyclohexenylene or 1,4-cyclohexadienylene, in which —$CH_2$— may be replaced once or twice, independently of one another, by —O— or —S— in such a way that heteroatoms are not linked directly, and which may be unsubstituted or mono- or poly-substituted by —F and/or —Cl, bicyclo[1.1.1]pentane-1,3-diyl, bicyclo[2.2.2]octane-1, 4-diyl, spiro[3.3]heptane-2,6-diyl, tetrahydropyran-2,5-diyl or 1,3-dioxane-2,5-diyl;

$Z^1$ and $Z^2$ each, independently of one another, denote a single bond, —$CF_2O$—, —$OCF_2$—, —$CH_2CH_2$—, —$CF_2CF_2$—, —$CF_2CH_2$—, —$CH_2CF_2$—, —CHF—CHF—, —(CO)O—, —O(CO)—, —$CH_2O$—, —$OCH_2$—, —CF=CH—, —CH=CF—, —CF=CF—, —CH=CH— or —C≡C—;

$R^1$ and $R^2$, independently of one another, denote hydrogen, an alkanyl, alkoxy, alkenyl or alkynyl radical having up to 15 C atoms, which is unsubstituted, monosubstituted by —CN or —$CF_3$ or mono- or polysubstituted by —F, —Cl, —Br and/or —I, in which one or more $CH_2$ groups are optionally each, independently of one another, replaced by —O—, —S—, —$SO_2$—, —CO—, —(CO)O—, —O(CO)— or —O—CO—O— in such a way that heteroatoms are not linked directly, —F, —Cl, —Br, —I, —CN, —SCN, —NCS or —$SF_5$;

where $A^1$, $A^2$, $Z^1$, $Z^2$ may each have identical or different meanings if m or n respectively is greater than 1, and where in the case where simultaneously n=0, m=0 and $X^1$, $X^2$ and $X^3$ are not equal to F, $R^1$ and $R^2$ then do not simultaneously denote H.

2. A compound according to claim 1, wherein one or more of the radicals $X^1$, $X^2$ and $X^3$ denote F.

3. A compound according to claim 1, wherein $X^1$ denotes F, Cl, CN or $CF_3$ and $X^2$ and $X^3$ denote hydrogen.

4. A compound according to claim 1, wherein $X^1$ denotes F.

5. A compound according to claim 1, wherein $Z^1$ and $Z^2$, independently of one another, denote a single bond, —$CF_2O$—, —$OCF_2$—, —$CF_2CF_2$—, —CH=CH—, —CF=CH—, —CH=CF— or —CF=CF—.

6. A compound according to claim 1, wherein $A^1$ and $A^2$, independently of one another, denote a ring of formula

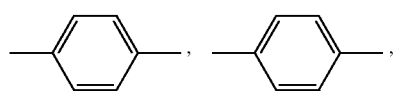

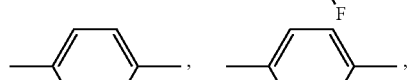

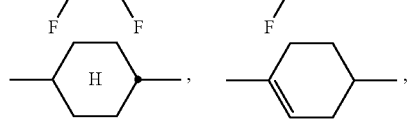

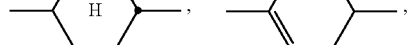

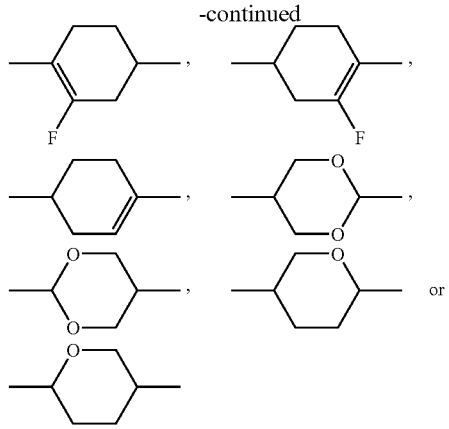

7. A compound according to claim 1, wherein
$R^1$ and $R^2$ each, independently of one another, denote an alkanyl radical, alkoxy radical or alkenyl radical having up to 7 carbon atoms, where each of these radicals is unsubstituted or mono- or polysubstituted by halogen, or denotes fluorine or hydrogen.

8. A compound according to claim 1, wherein
m and n are both zero, and
$R^1$ and $R^2$ each, independently of one another, are an unbranched alkanyl radical, alkoxy radical or alkenyl radical having up to 7 carbon atoms.

9. A compound according to claim 1, wherein m+n=1, and $A^1$ and $A^2$, independently of one another, denote

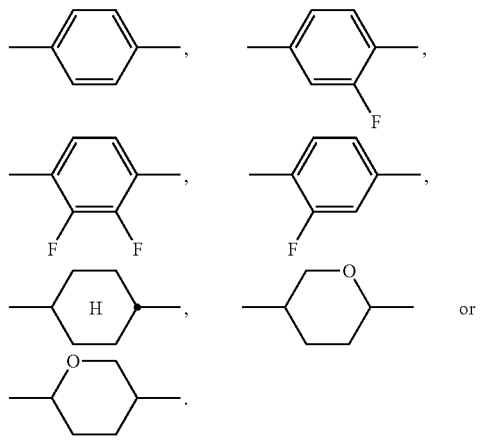

10. A compound according to claim 1, wherein m=0, and $R^1$ is an alkoxy radical or alkenyloxy radical having 2 to 7 carbon atoms.

11. A liquid-crystalline media comprising a compound according to claim 1.

12. A liquid-crystalline medium comprising at least two compounds, which comprises at least one compound according to claim 1.

13. An electro-optical display element containing a liquid-crystalline medium according to claim 12.

14. A process for preparing a compound according to claim 1, comprising cyclizing an appropriately substituted 2-(2-halophenyl)cyclohexanol compound to give a tetrahydrodibenzofuran compound.

* * * * *